United States Patent
Partridge et al.

(10) Patent No.: US 10,035,813 B2
(45) Date of Patent: *Jul. 31, 2018

(54) PRODRUG DERIVATIVES OF (E)-N-METHYL-N-((3-METHYLBENZOFURAN-2-YL)METHYL)-3-(7-OXO-5,6,7,8-TETRAHYDRO-1,8-NAPHTHYRIDIN-3-YL) ACRYLAMIDE

(71) Applicant: Debiopharm International SA, Lausanne (CH)

(72) Inventors: John J. Partridge, Chapel Hill, NC (US); John Colucci, Kirkland (CA); Yves Gareau, Notre-Dame de L'ile-Perrot (CA); Michel Therien, Toronto (CA); Robert Zamboni, Toronto (CA); Barry Hafkin, Austin, TX (US); Anthony Marfat, Mystic, CT (US); Helmi Zaghdane, Pincourt (CA)

(73) Assignee: Debiopharm International SA, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/534,573

(22) Filed: Nov. 6, 2014

(65) Prior Publication Data

US 2015/0065415 A1    Mar. 5, 2015

Related U.S. Application Data

(63) Continuation of application No. 14/010,166, filed on Aug. 26, 2013, now Pat. No. 8,901,105, which is a continuation of application No. PCT/IB2013/001780, filed on Jun. 19, 2013.

(60) Provisional application No. 61/661,559, filed on Jun. 19, 2012.

(51) Int. Cl.
| | | |
|---|---|---|
| *A61K 31/675* | (2006.01) | |
| *A61K 45/06* | (2006.01) | |
| *C07F 9/58* | (2006.01) | |
| *C07F 9/60* | (2006.01) | |
| *C07F 9/6561* | (2006.01) | |
| *A61K 31/662* | (2006.01) | |

(52) U.S. Cl.
CPC .......... *C07F 9/6561* (2013.01); *A61K 31/675* (2013.01); *A61K 45/06* (2013.01); *C07F 9/582* (2013.01); *C07F 9/60* (2013.01); *A61K 31/662* (2013.01)

(58) Field of Classification Search
CPC .... A61K 31/661; A61K 31/675; A61K 45/06; A61K 31/662; C07F 9/582; C07F 9/60; C07F 9/6561
See application file for complete search history.

(56) References Cited

U.S. PATENT DOCUMENTS

| | | |
|---|---|---|
| 3,828,068 A | 8/1974 | Minieri |
| 4,154,943 A | 5/1979 | Kuehne |
| 4,977,159 A | 12/1990 | Sevrin et al. |
| 5,416,193 A | 5/1995 | Desai |
| 5,614,551 A | 3/1997 | Dick et al. |
| 5,624,941 A | 4/1997 | Barth et al. |
| 5,932,743 A | 8/1999 | Collini et al. |
| 5,985,867 A | 11/1999 | Rodgers et al. |
| 5,989,832 A | 11/1999 | Trias et al. |
| 6,133,260 A | 10/2000 | Matzke et al. |
| 6,174,878 B1 | 1/2001 | Gamache et al. |
| 6,184,380 B1 | 2/2001 | Chiu et al. |
| 6,187,341 B1 | 2/2001 | Johnson et al. |
| 6,194,429 B1 | 2/2001 | Guinn et al. |
| 6,194,441 B1 | 2/2001 | Roberts et al. |
| 6,198,000 B1 | 3/2001 | Hawkins |
| 6,221,859 B1 | 4/2001 | Dorso et al. |
| 6,221,864 B1 | 4/2001 | Hirayama et al. |
| 6,235,908 B1 | 5/2001 | Fey |
| 6,239,113 B1 | 5/2001 | Dawson et al. |
| 6,239,141 B1 | 5/2001 | Allen et al. |
| 6,248,363 B1 | 6/2001 | Patel et al. |
| 6,267,985 B1 | 7/2001 | Chen et al. |
| 6,277,836 B1 | 8/2001 | Borody |
| 6,288,239 B1 | 9/2001 | Hollingsworth et al. |
| 6,291,462 B1 | 9/2001 | Bartholomaeus et al. |
| 6,294,192 B1 | 9/2001 | Patel et al. |
| 6,303,572 B1 | 10/2001 | Rowe |
| 6,309,663 B1 | 10/2001 | Patel et al. |
| 6,333,045 B1 | 12/2001 | Yasueda et al. |
| 6,340,689 B1 | 1/2002 | Dubois et al. |
| 6,346,391 B1 | 2/2002 | Oethinger et al. |
| 6,367,985 B1 | 4/2002 | Lee et al. |
| 6,372,752 B1 | 4/2002 | Staveski et al. |
| 6,388,070 B1 | 5/2002 | Deshpande et al. |
| 6,395,746 B1 | 5/2002 | Cagle et al. |
| 6,399,629 B1 | 6/2002 | Chamberland et al. |

(Continued)

FOREIGN PATENT DOCUMENTS

| | | |
|---|---|---|
| CA | 2444597 A1 | 10/2002 |
| CA | 2568914 A1 | 12/2005 |

(Continued)

OTHER PUBLICATIONS

Dykhuizen, "Santa Rosalia revisited: Why are there so many species of bacteria?", Antonie van Leeuwenhoek, 1998, Kluwer Academic Publishers, vol. 73, pp. 25-33.*

(Continued)

*Primary Examiner* — Sarah Pihonak
(74) *Attorney, Agent, or Firm* — Goodwin Procter LLP

(57) ABSTRACT

In part, the present disclosure is directed to prodrug derivatives of (E)-N-methyl-N-((3-methylbenzofuran-2-yl) methyl)-3-(7-oxo-5,6,7,8-tetrahydro-1,8-naphthyridin-3-yl) acrylamide compounds with significant solubility and bioavailability profiles.

27 Claims, 10 Drawing Sheets

(56) References Cited

U.S. PATENT DOCUMENTS

| | | |
|---|---|---|
| 6,406,880 B1 | 6/2002 | Thornton |
| 6,423,341 B1 | 7/2002 | Yamaguchi |
| 6,423,741 B1 | 7/2002 | Khanuja et al. |
| 6,428,579 B1 | 8/2002 | Valentini |
| 6,432,444 B1 | 8/2002 | Fischetti et al. |
| 6,432,670 B1 | 8/2002 | Payne et al. |
| 6,436,980 B1 | 8/2002 | Leger et al. |
| 6,441,162 B2 | 8/2002 | Yasui et al. |
| 6,448,054 B1 | 9/2002 | Poznansky et al. |
| 6,448,238 B1 | 9/2002 | Shoichet et al. |
| 6,448,449 B2 | 9/2002 | Larrow |
| 6,451,339 B2 | 9/2002 | Patel et al. |
| 6,451,816 B1 | 9/2002 | Biedermann et al. |
| 6,461,607 B1 | 10/2002 | Farmer |
| 6,461,829 B1 | 10/2002 | Kahne |
| 6,465,429 B1 | 10/2002 | Hancock et al. |
| 6,468,964 B1 | 10/2002 | Rowe |
| 6,469,046 B1 | 10/2002 | Daines et al. |
| 6,486,148 B2 | 11/2002 | Savage et al. |
| 6,486,149 B2 | 11/2002 | Onodera et al. |
| 6,486,165 B2 | 11/2002 | Zhang et al. |
| 6,489,318 B1 | 12/2002 | Copar et al. |
| 6,492,351 B1 | 12/2002 | Zhang et al. |
| 6,495,158 B1 | 12/2002 | Buseman et al. |
| 6,495,161 B1 | 12/2002 | Soon-Shiong et al. |
| 6,495,551 B1 | 12/2002 | Betts et al. |
| 6,497,886 B1 | 12/2002 | Breitenbach et al. |
| 6,500,459 B1 | 12/2002 | Chhabra et al. |
| 6,500,463 B1 | 12/2002 | van Lengerich |
| 6,503,539 B2 | 1/2003 | Gestrelius et al. |
| 6,503,881 B2 | 1/2003 | Krieger et al. |
| 6,503,903 B1 | 1/2003 | Miller et al. |
| 6,503,906 B1 | 1/2003 | Lee |
| 6,503,908 B1 | 1/2003 | Maw |
| 6,503,953 B2 | 1/2003 | Vyden |
| 6,503,955 B1 | 1/2003 | Dobrozsi et al. |
| 6,509,327 B1 | 1/2003 | Cagle et al. |
| 6,514,535 B2 | 2/2003 | Marchant |
| 6,514,541 B2 | 2/2003 | Khanuja et al. |
| 6,514,953 B1 | 2/2003 | Armitage et al. |
| 6,514,962 B1 | 2/2003 | Shibatani et al. |
| 6,514,986 B2 | 2/2003 | de Souza et al. |
| 6,515,113 B2 | 2/2003 | Raymond et al. |
| 6,517,827 B1 | 2/2003 | Bacon Kurtz et al. |
| 6,518,239 B1 | 2/2003 | Kuo et al. |
| 6,518,263 B1 | 2/2003 | Nishitani et al. |
| 6,518,270 B1 | 2/2003 | Amin et al. |
| 6,518,487 B1 | 2/2003 | Lowe et al. |
| 6,521,408 B1 | 2/2003 | Kawasaki |
| 6,525,066 B2 | 2/2003 | Fukumoto et al. |
| 6,527,759 B1 | 3/2003 | Tachibana et al. |
| 6,528,089 B1 | 3/2003 | Kothrade et al. |
| 6,531,126 B2 | 3/2003 | Farmer |
| 6,531,291 B1 | 3/2003 | Kabbash et al. |
| 6,531,465 B1 | 3/2003 | Ascher et al. |
| 6,531,508 B1 | 3/2003 | Nomura et al. |
| 6,531,649 B1 | 3/2003 | Mannerloef et al. |
| 6,559,172 B1 | 5/2003 | Heerding et al. |
| 6,573,272 B1 | 6/2003 | Miller et al. |
| 6,673,941 B2 | 1/2004 | Heerding et al. |
| 6,703,684 B2 | 3/2004 | Udrea et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,821,746 B2 | 11/2004 | DeWolf et al. |
| 6,846,819 B1 | 1/2005 | Miller et al. |
| 6,951,729 B1 | 10/2005 | DeWolf et al. |
| 6,964,970 B2 | 11/2005 | Miller et al. |
| 6,995,254 B1 | 2/2006 | Payne et al. |
| 7,048,926 B2 | 5/2006 | Brandt et al. |
| 7,049,310 B2 | 5/2006 | Burgess et al. |
| 7,250,424 B2 | 7/2007 | Burgess et al. |
| 7,449,458 B2 | 11/2008 | Bhamidipati et al. |
| 7,524,843 B2 | 4/2009 | Miller et al. |
| 7,538,108 B2 | 5/2009 | Singh et al. |
| 7,557,125 B2 | 7/2009 | Miller et al. |
| 7,563,892 B1 | 7/2009 | Singh et al. |
| 7,741,339 B2 | 6/2010 | Burgess et al. |
| 7,790,709 B2 | 9/2010 | Berman et al. |
| 7,790,716 B2 | 9/2010 | Miller et al. |
| 7,879,872 B2 | 2/2011 | Berman et al. |
| 7,989,448 B2 | 8/2011 | Singh et al. |
| 8,153,652 B2 | 4/2012 | Burgess et al. |
| 8,163,902 B2 | 4/2012 | Bhamidipati et al. |
| 8,173,646 B2 | 5/2012 | Miller et al. |
| 8,211,888 B2 | 7/2012 | Singh et al. |
| 8,211,889 B2 | 7/2012 | Singh et al. |
| 8,263,613 B2 | 9/2012 | Pauls et al. |
| 8,318,720 B2 | 11/2012 | Pauls et al. |
| 8,450,307 B2 | 5/2013 | Sargent et al. |
| 8,901,105 B2 | 12/2014 | Partridge et al. |
| 2001/0016662 A1 | 8/2001 | Golik et al. |
| 2003/0232850 A1 | 12/2003 | Miller et al. |
| 2004/0053814 A1 | 3/2004 | Brandt et al. |
| 2005/0250810 A1 | 11/2005 | Miller et al. |
| 2006/0142265 A1 | 6/2006 | Berman et al. |
| 2006/0183908 A1 | 8/2006 | Berman et al. |
| 2006/0211657 A1 | 9/2006 | Singh et al. |
| 2006/0234983 A1 | 10/2006 | Singh et al. |
| 2008/0125423 A1 | 5/2008 | Miller et al. |
| 2009/0042927 A1 | 2/2009 | Pauls et al. |
| 2009/0156578 A1 | 6/2009 | Pauls et al. |
| 2009/0221699 A1 | 9/2009 | Burgess et al. |
| 2010/0130470 A1 | 5/2010 | Pauls et al. |
| 2011/0124633 A1 | 5/2011 | Berman et al. |
| 2012/0010127 A1 | 1/2012 | Berman et al. |
| 2013/0237523 A1 | 9/2013 | Pauls et al. |
| 2013/0281442 A1 | 10/2013 | Hafkin |
| 2014/0107106 A1 | 4/2014 | Sargent et al. |

FOREIGN PATENT DOCUMENTS

| | | |
|---|---|---|
| CA | 2776849 A1 | 5/2011 |
| CN | 102675311 A | 9/2012 |
| EP | 0407200 A1 | 1/1991 |
| EP | 0953570 A1 | 11/1999 |
| EP | 1000935 A1 | 5/2000 |
| HU | 0203122 B | 5/1991 |
| HU | 210679 B | 6/1995 |
| WO | WO-1993/04035 A1 | 3/1993 |
| WO | WO-1995/18619 A1 | 7/1995 |
| WO | WO-1996/00730 A1 | 1/1996 |
| WO | WO-1997/48696 A1 | 12/1997 |
| WO | WO-1998/57952 A1 | 12/1998 |
| WO | WO-1999/24406 A1 | 5/1999 |
| WO | WO-2000/27628 A1 | 5/2000 |
| WO | WO-2000/57933 A1 | 10/2000 |
| WO | WO-2001/26652 | 4/2001 |
| WO | WO-2001/26654 A1 | 4/2001 |
| WO | WO-2001/27103 A1 | 4/2001 |
| WO | WO-2001/41573 A1 | 6/2001 |
| WO | WO-2001/48248 A2 | 7/2001 |
| WO | WO-2001/70172 A2 | 9/2001 |
| WO | WO-2002/10332 A1 | 2/2002 |
| WO | WO-2002/42273 A2 | 5/2002 |
| WO | WO-2002/48097 A1 | 6/2002 |
| WO | WO-2002/064572 A1 | 8/2002 |
| WO | WO-2003/086396 A1 | 10/2003 |
| WO | WO-2003/088897 A1 | 10/2003 |
| WO | WO-2004/014869 A2 | 2/2004 |
| WO | WO-2004/52890 A1 | 6/2004 |
| WO | WO-2004/82586 A2 | 9/2004 |
| WO | WO-2005/090367 A1 | 9/2005 |
| WO | WO-2007/053131 A2 | 5/2007 |
| WO | WO-2007/067416 A2 | 6/2007 |
| WO | WO-2008/009122 A1 | 1/2008 |
| WO | WO-2008/064274 A1 | 5/2008 |
| WO | WO-2008/098374 A1 | 8/2008 |
| WO | WO-2009/003136 A1 | 12/2008 |
| WO | WO-2010/0151689 | 12/2010 |
| WO | WO-2010/0151711 | 12/2010 |
| WO | WO-2011/002999 A1 | 1/2011 |
| WO | WO-2011/061214 A1 | 5/2011 |

(56) References Cited

FOREIGN PATENT DOCUMENTS

| WO | WO-2011/156811 A2 | 12/2011 |
|---|---|---|
| WO | WO-2013/080222 | 6/2013 |
| WO | WO-2013/190384 A1 | 12/2013 |

OTHER PUBLICATIONS

Chen et. al., "Synthesis and Antibacterial Evaluation of Certain Quinolone Derivatives", J. Med. Chem., 2001, American Chemical Society, vol. 44, pp. 2374-2377.*
Foroumadi et. al., "Synthesis and in vitro antibacterial evaluation of N-[5-(5-nitro-2-thienyl)-1.3.4-thiadiazole-2-yl] piperazinyl quinolines", Eur. J. Med. Chem.,2003, Elsevier, vol. 38, pp. 851-854.*
Abou-Gharbia et al., "Psychotropic agents: synthesis and antipsychotic activity of substituted beta-carbolines," *J Med Chem*, 30(6):1100-1105 (1987).
Ahsan et al., "Reserpine Analogues: Synthesis of B-Carboline Derrivatives," J. Chem. Soc., pp. 3928-3920, 1963.
Annesley et al., "Glucuronidation of prodrug reactive site: isolation and characterization of oxymethylglucuronide metabolite of fosphenytoin," *Clin Chem*, 47(5):910-8 (2001).
Barkema et al., "Invited Review: The Role of Cow, Pathogen, and Treatment Regimen in the Therapeutic Success of Bovine *Staphylococcus aureus* Mastitis," *Journal Dairy Science*, 89:1877-1895 (2006).
Bastin et al., "Salt Selection and Optimisation Procedures for Pharmaceutical New Chemical Entities," Organic Process Res. & Dev., 4(5):427-435 (2000).
Berge et al., "Pharmaceuticals Salts," J. of Pharm. Sciences, 66(1):1-19 (1977).
Bergler et al., "Protein EnvM is the NADH-dependent enoyl-ACP reductase (FabI) of *Escherichia coli*," *J Biol Chem*, 269(8):5493-5496 (1994).
Chen et al., "Synthesis and Antibacterial Evaluation of Certain Quinolone Derivatives," J Medicinal Chem, vol. 44, pp. 2374-2377 (2001).
Claus et al., "Formaldehydabspaltende Phenolcarbonsäurederivate," Monatsh. Chem., 97:271-279, 1966.
Database CA on STN, AN 7:66733, Rosenmund et al., "Chemistry of indole II. Beckmann and Schmidt Rearrangements of Some Indole Ketones," Chem. Ber., 103(2): 496-509 (1970).
Database CAOLD on STN, AN CA51:10524d, Hellman etal., "N-Mannich bases (VI) condensation of N-dialkylaminomethylbenzamides with amines and amides, (VII) N-acylaminomethylation of indole," Direct Submission, 1953.
Database CAPLUS on STN AN 1999:325910 Aslanian, et al., "Preparation of (phenylaiky)imidazoles as H3 receptor antagonists," WO99/24406. 1999.
Database CAPLUS on STN, AN 1977:439214. Misztal et al., "Synthesis and pharmacologic properties of pyridoyl derivatives of 3-methylaminoindole 2-methyltryptamine and isotryptamine," Arch Immuno Ther Exp., 24(6):851-862, 1976.
Database CAPLUS on STN, AN 1986:68547, Stuetz et al., "Synthesis and Structure-activity relationships of naftifine-related allylamine antimycotics," J. Med. Chem., 29(1):112-25, 1986.
Database CAPLUS on STN, AN 1991:428908, Fuse et al., "Preparation of cinnamamide derivatives an antihyperlipidemics," EP407200A1, 1991.
Database Crossfile Beilstein, 1966, Database accession No. 2819049, 2819050, XP002216033.
Dykhuizen, Antonie van Leeuwenhoek, Kluwer Academic Publishers, col. 73, pp. 25-33 (1998).
Ettmayer et al., "Lessons learned from marketed and investigational prodrugs," J Med Chem, 47(10):2393-2404 (2004).
European Search Report (extended) for European Patent Application No. 08714623.9 dated Jul. 16, 2014. 5 pages.
European Search Report for EP 11 793 310.1 dated Oct. 30, 2013, 9 pages.

Foroumadi et al., "Synthesis and in Vitro Antibacterial Evaluation of N-[5-(5-Nitro-2-Thienyl)-1,3,4-Thiadiazole-2-yl] Piperazinyl Quinolones," European J Medicinal Chem, 38:851-854 (2003).
Grassberger et al., "Preparation and antibacterial activities of new 1,2,3-diazaborine derivatives and analogues," *J Med Chem.*, 27(8):947-953 (1984).
Heath et al., "A triclosan-resistant bacterial enzyme," *Nature*, 406(6792):145-146 (2000).
Heath et al., "Regulation of fatty acid elongation and initiation by acyl-acyl carrier protein in *Escherichia coli*," *J Biol Chem.*, 271(4):1833-1836 (1996).
Heck, "Palladium-Catalyzed Vinylation of Organic Halides," Organic Reactions, 1982, 27, pp. 345-390.
Heimbach et al., "Absorption rate limit considerations for oral phosphate prodrugs," *Pharm Res.*, 20(6):848-856 (2003).
Himmer et al., "Synthesis and antibacterial in vitro activity of novel analogues of nematophin," *Bioorg Med Chem Lett.*, 8(15):2045-2050 (1998).
Hungarian Search Report dated Dec. 31, 2003, 1 page.
International Preliminary Report on Patentability dated Jan. 20, 2009, for PCT/CA2007/001277, 8 pages.
International Search Report and Written Opinion for International Application No. PCT/IB2013/001780 dated Dec. 3, 2013, 12 pages.
International Search Report and Written Opinion for International Application No. PCT/US2011/040187 dated Nov. 30, 2011, 7 pages.
International Search Report dated Jun. 5, 2008 for PCT/CA2008/000300, 3 pages.
International Search Report dated Sep. 12, 2007 for PCT/US2006/045903, 6 pages.
Jianxiong Li et al., "Synthesis and Antistaphylococcal Activity of Nematophin and Its Analogs," Bioorganic & Medicinal Chemistry Letters Oxford, GB, 7(10): 1349-1352, (May 20, 1977).
Jossang-Yanagida et al., "Tetrahydropyridoazepines and Tetrahydropyridoazepinones from the Corresponding Dihydroquinolones," J. Heterocyclic Chemistry, 1978, vol. 15, pp. 249-251.
Kaplan et al., "F1-2005—In Vitro and In Vivo Absorption Properties of AFN-1252, a Novel Specific-Spectrum Anti-Staphylcoccal Agent," 233—New Agents on Bacterial Membranes Presentation Abstract Tuesday, Sep. 15, 2009, 9:00 AM-11:00 AM.
Kaplan et al., "F1-2006—Correlation of AFN-1252 Phase 0 Microdosing and Phase 1 Pharmacokinetics," 233—New Agents on Bacterial Membranes Presentation Abstract Tuesday, Sep. 15, 2009.
Karlowsky et al., "In vitro activity of API-1252, a novel FabI inhibitor, against clinical isolates of *Staphylococcus aureus* and *Staphylococcus epidermidis*," *Antimicrobial Agents and Chemotherapy*, 51(4);1580-1581 (2007).
Karlowsky et al., "AFN-1252, a FabI Inhibitor, Demonstrates a *Staphylococcus*-Specific Spectrum of Activity," *Antimicrobial Agents and Chemotherapy*, 53(8); 3544-3548 (2009).
Kearney et al., "The in vitro enzymic labilities of chemically distinct phosphomonoester prodrugs", Pharm Res, 9(4):497-503 (1992).
Leppik et al "Pharmacokinetics and safety of a phenytoin prodrug given i.v. or i.m. in patients" *Neurology.*, 40(3 Pt 1):456-60 (1990).
Levy et al., "Molecular basis of triclosan activity," *Nature.*, 398(6726):383-384 (1999).
McMurry et al., "Triclosan targets lipid synthesis," *Nature.*, 394(6693):531-532 (1998).
Miller et al., "Discovery of aminopyridine-based inhibitors of bacterial enoyl-ACP reductase (FabI)," *J Med Chem.*, 45(15):3246-3256 (2002).
Misztal et al., "Synthesis and pharmacologic properties of pyridoyl derivatives of 3-methylaminoindole 2-methyltryptamine and isotryptamine," *Arch Immunol Ther Exp (Warsz).*, 24(6):851-862 (1976).
Pachter et al., "The Chemistry of Hortiamine and 6-Methoxyhetsinine," J. Amer. Chem., 83:635-642 (1961).
Patent abstract of Japan vol. 2000, No. 02, Feb. 29, 2000, JP 11-302173.
Payne et al., "Bacterial Fatty-Acid Biosynthesis: A Genomics-Driven Target for Antibacterial Drug Discovery," Drug Discovery Today, 2008 pp. 537-541.

(56) References Cited

OTHER PUBLICATIONS

Payne et al., "Discovery of a Novel and Potent Class of Fab I-Directed Antibacterial Agents," *Am Soc for Microbiology*, 46(10):3118-3124 (2002).

Ramnauth et al., "2,3,4,5-Tetrahydro-1H-pyrido[2,3-b and e][1,4]diazepines as inhibitors of the bacterial enoyl ACP reductase, Fab I," *Bioorganic & Medicinal Chemistry Letters*, 19(18):5359-5362 (2009).

Rautio et al., "Prodrugs: Design and Clinical Applications," Nature Reviews Drug Discovery, vol. 7, pp. 255-270 (2008).

Rehse et al., "Dopaminanaloge 1,2,3,4-Tetrahydro-B-Carboline," Arch. Pharm., 311(1): 11-18 (1978).

Seefeld et al., "Indole naphthyridinones as inhibitors of bacterial enoyl-ACP reductases FabI and FabK," *J Med Chem.*, 46(9):1627-1635 (2003).

Shoji et al., "Two Novel Alkaloids from Evodia Rutaecarpa," J. Natural Products, 52(5):1160-1162 (1989).

Sladowska et al., "Synthesis and properties of amides of 1-benzyl-3-methyl- and 1-butyl-3-phenyl-7-methyl-4-oxo-2-thioxo (2,4-dioxo)-1,2,3,4-tetrahydropyrido-[2,3-d]pyrimidine-6-carboxy lic acids," *Farmaco Sci.*, 41(12):954-963 (1986).

Stutz et al. "Synthesis and Structure-Activity Relationships of Naftifine-Related Allylamine Antimycotics," Journal of Medicinal Chemistry, 1986, vol. 29, No. 1, 112-125.

Turnowsky et al., "envM genes of *Salmonella typhimurium* and *Escherichia coli*," *J Bacteriol.*, 171(12):6555-6565 (1989).

Varia et al., "Phenytoin Prodrugs III: Water-Soluble Prodrugs for Oral and/or Parenteral Use", J Pharm Sci, 73(8):1068-1073 (1984).

Varia et al., "Phenytoin prodrugs IV: Hydrolysis of various 3-(hydroxymethyl)phenytoin esters", J Pharm Sci, 73(8):1074-1080 (1984).

Varia et al., "Phenytoin prodrugs V: In vivo evaluation of some water-soluble phenytoin prodrugs in dogs", J Pharm Sci, 73(8):1080-1087 (1984).

Varia et al., "Phenytoin prodrugs VI: In vivo evaluation of a phosphate ester prodrug of phenytoin after parenteral administration to rats", J Pharm Sci, 73(8):1087-1090 (1984).

Ward et al., "Kinetic and structural characteristics of the inhibition of enoyl (acyl carrier protein) reductase by triclosan," *Biochemistry.*, 38(38):12514-12525 (1999).

\* cited by examiner

PRODRUG DERIVATIVES OF (E)-N-METHYL-N-((3-METHYLBENZOFURAN-2-YL)METHYL)-3-(7-OXO-5,6,7,8-TETRAHYDRO-1,8-NAPHTHYRIDIN-3-YL)ACRYLAMIDE

CROSS REFERENCE TO RELATED APPLICATIONS

This application is a continuation of U.S. patent application Ser. No. 14/010,166, filed Aug. 26, 2013, which is a continuation of International Patent Application No. PCT/IB2013/001780, filed Jun. 19, 2013, which claims priority to and the benefit of U.S. Provisional Patent Application No. 61/661,559, filed Jun. 19, 2012, the entirety of each of which are incorporated by reference herein.

BACKGROUND

Infections caused by or related to bacteria are a major cause of human illness worldwide. Unfortunately, the frequency of resistance to standard antibacterials has risen dramatically over the last decade, especially in relation to *Staphylococcus aureus*. For example, such resistant *S. aureus* includes MRSA, resistant to methicillin, vancomycin, linezolid and many other classes of antibiotics, or the newly discovered New Delhi metallo-beta-lactamase-1 (NDM-1) type resistance that has shown to afford bacterial resistant to most known antibacterials, including penicillins, cephalosporins, carbapenems, quinolones and fluoroquinolones, macrolides, etc. Hence, there exists an urgent, unmet, medical need for new agents acting against bacterial targets.

In recent years, inhibitors of FabI, a bacterial target involved in bacterial fatty acid synthesis, have been developed and many have been promising in regard to their potency and tolerability in humans, including a very promising FabI inhibitor, (E)-N-methyl-N-((3-methylbenzofuran-2-yl)methyl)-3-(7-oxo-5,6,7,8-tetrahydro-1,8-naphthyridin-3-yl)acrylamide. This compound, however, has been found to be difficult or impracticable to formulate into acceptable oral and parenteral (e.g., intravenous or subcutaneous) formulations, and has marked insolubility, poor solution stability, and oral bioavailability. Much effort, over a decade or more, has been expended to design and synthesize an alternative compound that retains the significant inhibition of FabI upon administration, but has improved physical and chemical characteristics that finally allow for practical oral and parenteral formulations. Up to now, no such compound has been identified that has adequate stability in the solid state, in aqueous solutions, together with excellent oral bioavailability that is necessary for oral and/or a parenteral administration, and is capable of being formulated into an oral and/or intravenous or intramuscular drug product using practical and commonly utilized methods of sterile formulation manufacture.

SUMMARY

The present disclosure is directed to specific prodrugs of the active compound (E)-N-methyl-N-((3-methylbenzofuran-2-yl)methyl)-3-(7-oxo-5,6,7,8-tetrahydro-1,8-naphthyridin-3-yl)acrylamide (compound IV), a potent inhibitor of bacterial fatty acid metabolism (via inhibition of FabI). Disclosed prodrug compounds can be administered by oral, intravenous, and/or intramuscular routes and once administered, undergo in vivo a biotransformation in one or more stages to liberate the active compound. The disclosed prodrugs are surprisingly stable in the solid state while also having high aqueous solubility and bioavailability properties. For example, one or more disclosed compounds have also been found to be surprisingly stable to sterilization by gamma radiation, and thus well suited to the production of a sterile formulation for use in the treatment of illnesses caused by bacterial infections.

Provided herein for example, are compounds represented by:

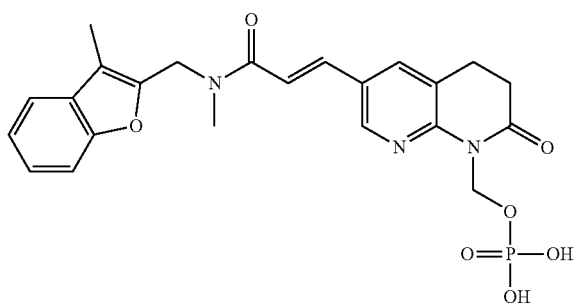 [SMILES: Cc1c(CN(C)C(=O)/C=C/c2cnc3c(c2)CCC(=O)N3COP(=O)(O)O)oc2ccccc12]

and pharmaceutically acceptable salts thereof.

For example, provided herein is a compound represented by:

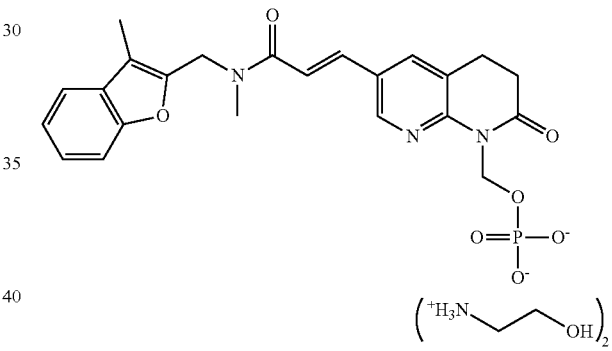

that is both surprisingly stable in crystalline form, and very soluble in aqueous solutions at room temperature. (e.g. 25° C.).

DETAILED DESCRIPTION

Introduction

Figure 1A:
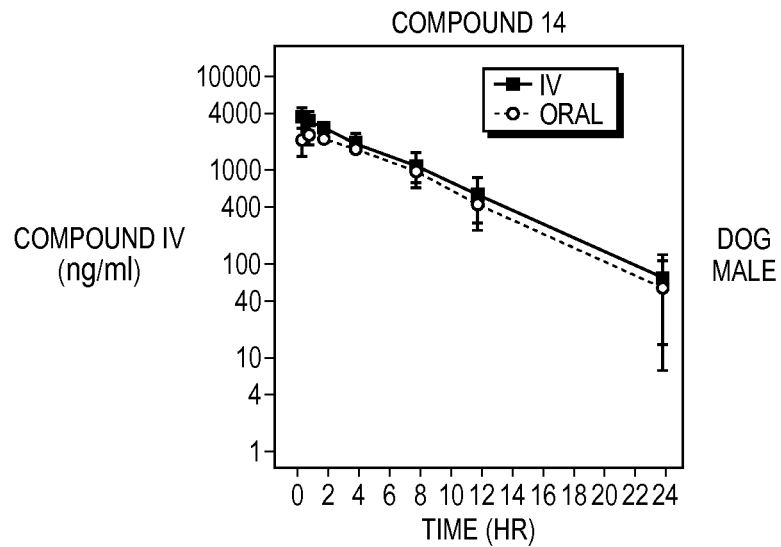
FIGS. 1A-F depict mean plasma time-concentration profiles of disclosed compounds at a dose level of 5 mg/kg in male dogs and female rats, and specifically show the pharmacokinetics of Compound IV in male dogs and female rats after intravenous or oral administration of Compound 9, Compound 10 and Compound 14.

The disclosure is generally directed to compounds that are in part e.g., soluble and stable in water and/or in other solvents at e.g., room temperature at an acceptable pH such as a pH between about 4 and about 8, e.g. at a pH of about 6, or about 7.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The term "including" is used to mean "including but not limited to". "Including" and "including but not limited to" are used interchangeably.

The term "FabI" is art-recognized and refers to the bacterial enzyme believed to function as an enoyl-acyl carrier protein (ACP) reductase in the final step of the four reactions involved in each cycle of bacterial fatty acid biosynthesis. This enzyme is believed to be widely distributed in bacteria and plants.

The term "enzyme inhibitor" refers to any compound that prevents an enzyme from effectively carrying out its respective biochemical roles. Therefore a "FabI inhibitor" is any compound that inhibits FabI from carrying out its biochemical role. The amount of inhibition of the enzyme by any such compound will vary and is described herein and elsewhere.

The term "antibiotic agent" or "antibacterial agent" shall mean any drug that is useful in treating, preventing, or otherwise reducing the severity of any bacterial disorder, or any complications thereof, including any of the conditions, disease, or complications arising therefrom and/or described herein. Antibiotic agents include, for example, cephalosporins, quinolones and fluoroquinolones, penicillins and beta lactamase inhibitors, carbapenems, monobactams, macrolides and lincosamides, glycopeptides, rifampin, oxazolidinones, tetracyclines, aminoglycosides, streptogramins, sulfonamides, and the like. Other general categories of antibiotic or antibacterial agents which may be part of a subject composition include those agents known to those of skill in the art as antibiotics and that qualify as (with defined terms being in quotation marks): "drug articles" recognized in the official United States Pharmacopoeia or official National Formulary (or any supplement thereto); "new drug" and "new animal drug" approved by the FDA of the U.S. as those terms are used in Title 21 of the United States Code; any drug that requires approval of a government entity, in the U.S. or abroad ("approved drug"); any drug that it is necessary to obtain regulatory approval so as to comply with 21 U.S.C. § 355(a) ("regulatory approved drug"); any agent that is or was subject to a human drug application under 21 U.S.C. § 379(g) ("human drug"). (All references to statutory code for this definition refer to such code as of the original filing date of the provisional application of which this application claims priority). Other antibiotic or antibacterial agents are disclosed herein, and are known to those of skill in the art. In certain embodiments, the term "antibiotic agent" does not include an agent that is a FabI inhibitor, so that the combinations of the present invention in certain instances will include one agent that is a FabI inhibitor and another agent that is not.

The term "illness" as used herein refers to any illness caused by or related to infection by an organism.

The term "bacterial illness" as used herein refers to any illness caused by or related to infection by bacteria.

The term "cis" is art-recognized and refers to the arrangement of two atoms or groups around a double bond such that the atoms or groups are on the same side of the double bond. Cis configurations are often labeled as (Z) configurations.

The term "substantially the same" when used to describe X-ray powder diffraction patterns, is meant to include patterns in which peaks are within a standard deviation of ±0.2 2θ.

The term "trans" is art-recognized and refers to the arrangement of two atoms or groups around a double bond such that the atoms or groups are on the opposite sides of a double bond. Trans configurations are often labeled as (E) configurations.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Antibiotic and antibacterial agents and Fab I inhibitors are examples of therapeutic agents.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The compounds of the disclosure may contain one or more chiral centers and/or double bonds and, therefore, exist as geometric isomers, enantiomers or diastereomers. The enantiomer and diastereomers may be designated by the symbols "(+)," "(−)." "R" or "S," depending on the configuration of substituents around the stereogenic carbon atom, but the skilled artisan will recognize that a structure may denote one or more chiral centers implicitly. Mixtures of enantiomers or diastereomers may be designated "(±)" in nomenclature, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans" or "Z/E."

The term "stereoisomers" when used herein consist of all geometric isomers, enantiomers or diastereomers. The present invention encompasses various stereoisomers of these compounds and mixtures thereof. Conformational isomers and rotamers of disclosed compounds are also contemplated.

Individual enantiomers and diastereomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. The compounds disclosed here may exist in single or multiple crystalline forms or polymorphs. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$ $^{31}P$, $^{32}P$, $^{35}S$, $^{18}F$ and $^{36}Cl$, respectively. For example, a compound of the invention may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

The term "$ED_{50}$" is art-recognized. In certain embodiments, $ED_{50}$ means the effective dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term that refers to the therapeutic index of a drug, defined as $ED_{50}/LD_{50}$.

The term "$K_i$" is art-recognized and refers to the dissociation constant of the enzyme-inhibitor complex.

The term "antimicrobial" is art-recognized and refers to the ability of the compounds disclosed herein to prevent, inhibit or destroy the growth of microbes such as bacteria, fungi, protozoa and viruses.

The term "antibacterial" is art-recognized and refers to the ability of the compounds disclosed herein to prevent, inhibit or destroy the growth of microbes of bacteria.

The term "microbe" is art-recognized and refers to a microscopic organism. In certain embodiments the term microbe is applied to bacteria. In other embodiments the term refers to pathogenic forms of a microscopic organism.

The term "alkyl" as used herein refers to a saturated straight or branched hydrocarbon, such as a straight or branched group of 1-6, 1-4, or 1-3 carbon atoms, referred to herein as $C_1$-$C_6$alkyl, $C_1$-$C_4$alkyl, and $C_1$-$C_3$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, a phosphate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate, phosphinate and phosphate), sulfonyl (including sulfate, sulfonamido, sulfamoyl and sulfonate), and silyl groups, as well as ethers, alkylthios, carbonyls (including ketones, aldehydes, carboxylates, and esters), nitrile and isonitrile, and the like.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, phosphate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "aralkyl" or "arylalkyl" is art-recognized and refers to an alkyl group substituted with an aryl group (e.g., an aromatic or heteroaromatic group).

The term "carbocycle" is art-recognized and refers to an aromatic or non-aromatic ring in which each atom of the ring is carbon.

The term "cycloalkyl" as used herein refers to a monocyclic saturated or partically unsaturated hydrocarbon group of for example 3-6, or 4-6 carbons, referred to herein, e.g., as "$C_{3-6}$cycloalkyl" or "$C_{4-6}$cycloalkyl," and derived from a cycloalkane. Exemplary cycloalkyl groups include, but are not limited to, cyclohexane, cyclohexene, cyclopentane, cyclobutane, cyclopropane or cyclopentene.

The terms "halo" or "halogen" as used herein refer to F, Cl, Br, or I.

The terms "heteroaryl" as used herein refers to a monocyclic aromatic 4-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, benzofuran, thiophene, pyrrole, thiazole, oxazole, isothiazole, isoxazole, imidazole, pyrazole, triazole, pyridine, and pyrimidine.

The terms "hydroxy" and "hydroxyl" as used herein refers to the radical —OH.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on page 560 of "*Advanced Inorganic Chemistry*" by Cotton and Wilkinson, Interscience Publishers, 1966.

The definition of each expression, e.g. alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate, p-toluenesulfonate, methanesulfonate, and nonafluorobutanesulfonate functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in the compositions disclosed herein may exist in particular geometric or stereoisomeric forms. In addition, polymers of the present invention may also be optically active. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound disclosed herein is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "prodrug" refers to a derivative of an active compound (drug) that undergoes a transformation under the conditions of use, such as within the body, to release the active drug. Prodrugs are frequently, but not necessarily, pharmacologically inactive until converted into the active drug.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds.

For purposes of this invention, the chemical elements are identified in accordance with the Periodic Table of the Elements, CAS version, *Handbook of Chemistry and Physics*, $67^{th}$ Ed., 1986-87, inside cover. Also for purposes of the disclosure, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The definition of each expression, e.g. lower alkyl, m, n, p and the like, when it occurs more than once in any structure, is intended to be independent of its definition elsewhere in the same structure.

The term "pharmaceutically-acceptable salts" is art-recognized and refers to the relatively non-toxic, inorganic and organic acid addition salts, or inorganic or organic base addition salts of compounds, including, for example, those contained in compositions of the present invention.

The term "treating" includes any effect, e.g., lessening, reducing, modulating, or eliminating, that results in the improvement of the condition, disease, disorder and the like.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal. Non human animals include companion animals (e.g. cats, dogs) and animals raised for consumption (i.e. food animals), such as cows, pigs, chickens)

The term "mammal" is known in the art, and exemplary mammals include humans, primates, bovines, porcines, canines, felines, and rodents (e.g., mice and rats).

The term "bioavailable" is art-recognized and refers to a form of the subject disclosure that allows for it, or a portion of the amount administered, to be absorbed by, incorporated to, or otherwise physiologically available to a subject or patient to whom it is administered.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as dextrose, lactose, glucose and sucrose; (2) starches, such as corn starch and potato starch; (3) cellulose, and its derivatives, such as microcrystalline cellulose, sodium carboxymethyl cellulose, methyl cellulose, ethyl cellulose, hydroxypropylmethyl cellulose (HPMC), and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate, glyceryl behenate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. The disclosed excipients may serve more than one function. For example, fillers or binders may also be disintegrants, glidants, anti-adherents, lubricants, sweeteners and the like.

Contemplated equivalents of the compositions described herein include compositions which otherwise correspond thereto, and which have the same general properties thereof, wherein one or more simple variations of substituents or components are made which do not adversely affect the characteristics of the compositions of interest. In general, the components of the compositions of the disclosure may be prepared by the methods illustrated in the general reaction schema and written procedures as, for example, described below, or by modifications thereof, using readily available starting materials, reagents and conventional synthesis procedures. In these reactions, it is also possible to make use of variants which are in themselves known, but are not mentioned here.

The disclosed compounds can be characterized by X-ray powder diffractometry (XRPD). An XRPD spectrum may be obtained with a measurement error depending on measurement conditions. In particular, intensities in a XRPD may fluctuate depending on measurement conditions. Therefore, it should be understood that the compounds providing any XRPD spectra substantially the same as the disclosed spectra fall within the scope of the disclosure. Those skilled in the art can readily judge the substantial identity of XRPD spectra.

Generally, a measurement error of diffraction angle for a X-ray powder diffraction is about 5% or less, and such degree of a measurement error should be taken into account as to diffraction angles. For example, the diffraction angles may be reported with a measurement error of ±1°, ±2°, ±3°, or ±5° 2θ.

Compounds

Disclosed herein, for example, are compounds represented by formula I:

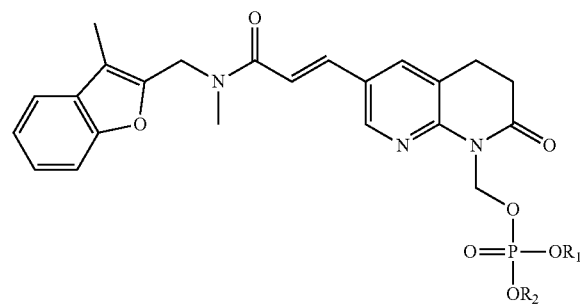

I where $R_1$ and $R_2$ are each independently selected from the group consisting of hydrogen, an alkali metal, $NH_4^+$, $NH^+$—$(R_3)_3$, $NH_2^+$—$(R_3)_2$, and $NH_3^+$—$(R_3)$, or $R_1$ and $R_2$ taken together are an alkaline earth metal; and $R_3$ is independently selected for each occurrence from the group consisting of hydrogen, $C_{1-6}$ alkyl-, hydroxy$C_{1-6}$alkyl-, aryl (e.g., phenyl) and aryl$C_{1-6}$alkyl (e.g. benzyl).

In certain embodiments, $R_1$ and $R_2$ are each $NH_3^+$—$(R_3)$; or $R_1$ and $R_2$ is H; and one of $R_1$ and $R_2$ is $NH_4^+$ or $NH_3^+$—$(R_3)$. $R_3$ for example, may be —$CH_2CH_2OH$.

In certain embodiments, $R_1$ and $R_2$ are an alkali metal. Alkali metals are found in Group 1 of the periodic table and have only one electron in their outer shell. Examples of alkali metals are lithium, sodium, and potassium. In certain embodiments, for example, the alkali metal is sodium or potassium.

In other embodiments, $R_1$ and $R_2$ taken together are an alkaline earth metal. Alkaline earth metals are found in Group 2 of the periodic table and have an oxidation number of $^+2$. Examples of alkaline earth metals are beryllium, magnesium, and calcium. In certain embodiments, for example, the alkaline earth metal is calcium or magnesium.

In some embodiments, $R_1$ and $R_2$ taken together are a metal from Groups 8-12 of the periodic table that has an oxidation number of $^+2$, such as iron, nickel, copper and zinc, or $^+3$, such as iron In certain embodiments, for example, the metal is iron or zinc.

In yet another embodiment, $R_1$ and $R_2$ are each independently selected from hydrogen and an ammonium moiety represented by $NH_3^+$—$(R_3)$. In certain other embodiments one of $R_1$ or $R_2$ is H; if $R_1$ is H, $R_2$ is an ammonium moiety represented by $N(R_3)_4^+$ (e.g., $NH_3^+$—$(R_3)$,) or if $R_2$ is H, $R_1$ is ammonium moiety represented by $N(R_3)_4^+$ (e.g., $NH_3^+$—$(R_3)$,). Alternatively, both $R_1$ and $R_2$ may each be $NH_3^+$—$(R_3)$. In certain embodiments, the ammonium moiety is selected from the group consisting of ammonium, methylammonium, dimethylammonium, ethylammonium, diethylammonium, ethanolammonium, diethanolammomium and triethanolammonium.

In some embodiments, for example, a provided compound is represented by:

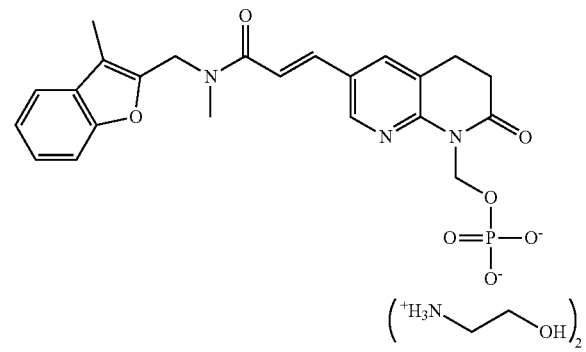

((E)-6-[(N-methyl-((3-methylbenzofuran-2-yl)methyl) amino)-3-oxoprop-1-en-1-yl)-2-oxo-3,4-dihydro-1,8-naphthyridin-1(2H)-yl]methylphosphate bis-ethanolammonium salt; compound 10)

In other embodiments, a provided compound is represented by:

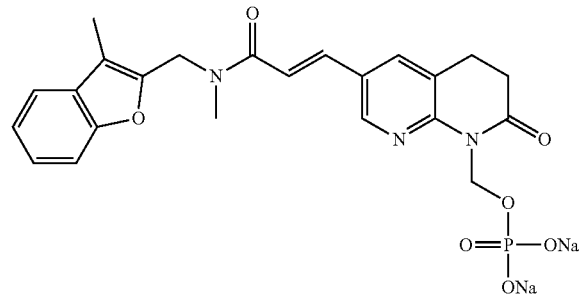

((E)-6-[(N-methyl-((3-methylbenzofuran-2-yl)methyl) amino)-3-oxoprop-1-en-1-yl)-2-oxo-3,4-dihydro-1,8-naphthyridin-1(2H)-yl]methylphosphate disodium salt; compound 9) or the compound:

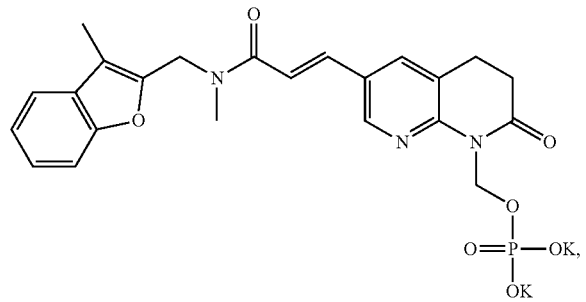

((E)-6-[(N-methyl-((3-methylbenzofuran-2-yl)methyl) amino)-3-oxoprop-1-en-1-yl)-2-oxo-3,4-dihydro-1,8-naphthyridin-1(2H)-yl]methylphosphate dipotassium salt; compound 11)

In yet another embodiment, a representative compound is

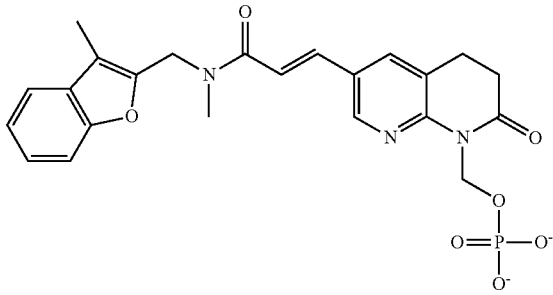

2NH₄⁺

((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate bis-ammonium salt; compound 14).

Exemplary compounds provided herein may be represented by:

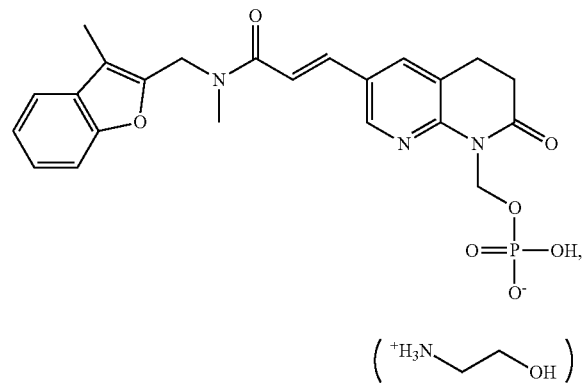

((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate monoethanolammonium salt);

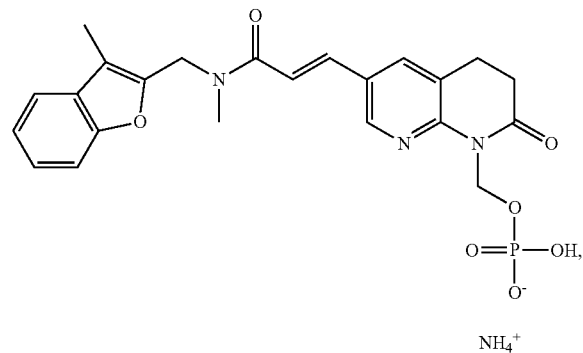 [SMILES: Cc1c(CN(C)C(=O)/C=C/c2cnc3c(c2)CCC(=O)N3COP(=O)([O-])O)oc2ccccc12 ; [NH4+]]

NH₄⁺

((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate monoammonium salt);

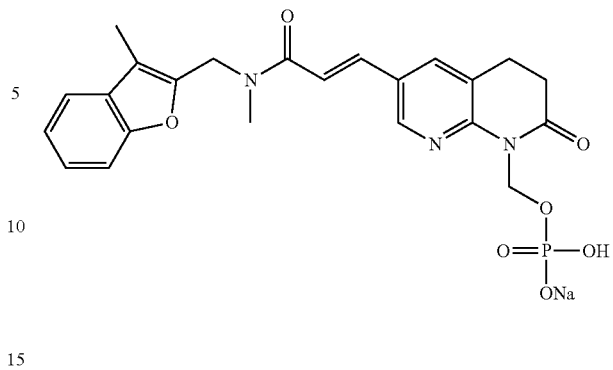

((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate monosodium salt), and:

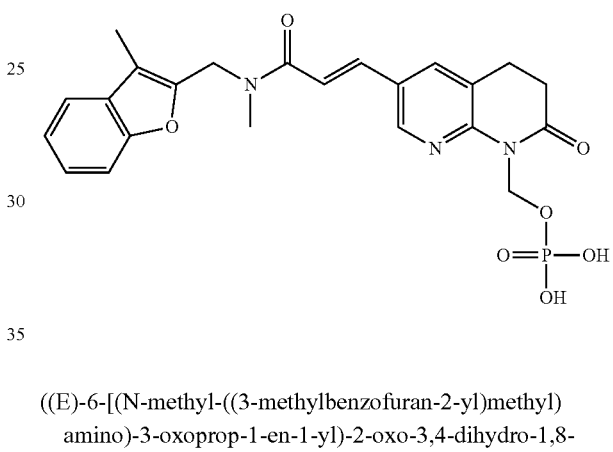

((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methyl phosphate, compound V).

Contemplated herein are compounds represented by:

AA

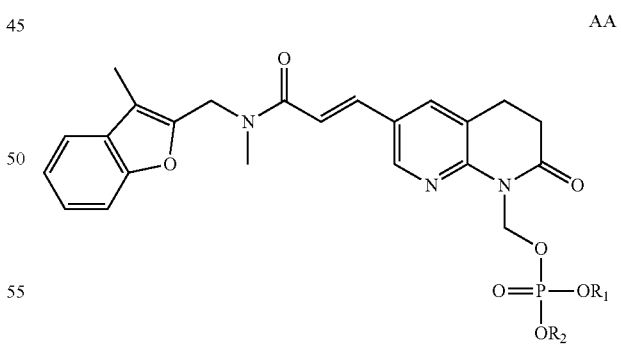

wherein $R_1$ and $R_2$ may independently selected from H and —C($R_{10}R_{10}$)—O—C(O)—$R_{11}$, wherein $R_{10}$ is independently selected from H and $C_{1-6}$alkyl (e.g. methyl); $R_{11}$ is selected from the group consisting of $C_{1-6}$ alkyl (e.g. methyl), $C_{3-6}$cycloalkyl, phenyl, —O—$C_{1-6}$ alkyl (e.g. —O—$CH_3$ or -O—$C_2H_5$), —O—$C_{3-6}$cycloalkyl, and –O-phenyl, or a pharmaceutically acceptable salt thereof Also provided herein are compounds represented by:

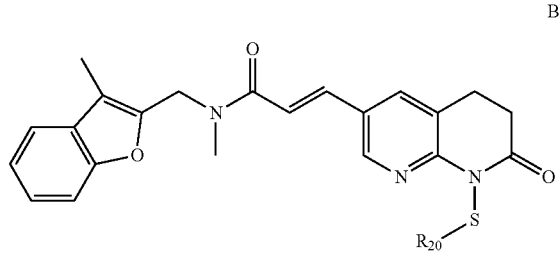

BB where $R_{20}$ is selected from the group consisting of $C_{1-6}$alkyl (optionally substituted by hydroxyl, $NR_{23}NR_{24}$, (wherein $R_{23}$ and $R_{24}$ are independently selected for each occurrence from H, —C(O)—$C_{1-6}$alkyl, $C_{1-6}$alkyl or taken together form a heterocycle), hydroxyl, —O—$C_{1-6}$alkyl, or C(O)—$C_{1-6}$alkyl), —$CH_2$—$CH(CO_2R_{21})$—$NHR_{22}$, —$C_{1-6}$alkyl-C(O)O—$R_{21}$, phenyl and $C_{3-6}$cycloalky; wherein $R_{21}$ is independently selected from each occurrence from H and $C_{1-6}$alkyl, and $R_{22}$ is selected from H and —C(O)—$C_{1-6}$alkyl; or a pharmaceutically acceptable salt thereof In other embodiments, provided herein are compounds represented by:

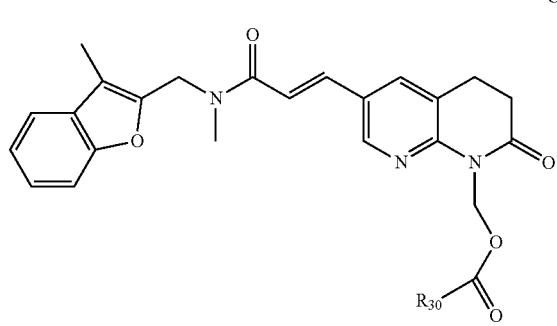

CC wherein $R_{30}$ is selected from the group consisting of H, —O—$C_{1-6}$alkyl (e.g., —O-ethyl) and $C_{1-6}$alkyl (e.g., t-butyl), or a pharmaceutically acceptable salt thereof.

Also provided herein are compounds represented by:

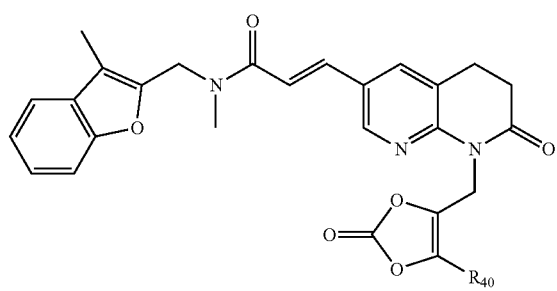

DD wherein $R_{40}$ is selected from H and $C_{1-6}$alkyl (e.g. methyl), or a pharmaceutically acceptable salt thereof In other embodiments, provided herein are compounds represented by:

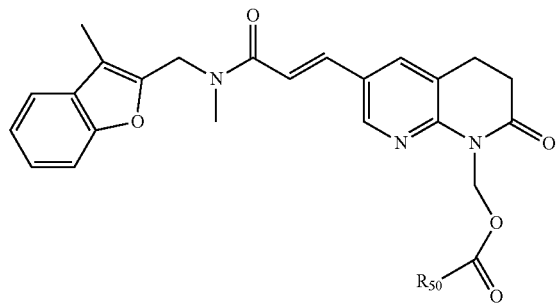

EE wherein $R_{50}$ is an amino acid residue. For example, $R_{50}$ may be selected from the group consisting of —$CR_{51}R_{52}$—$NR_{53}R_{54}$, wherein $R_{51}$ and $R_{52}$ are independently selected from the group consisting of $C_{1-4}$alkyl optionally substituted by carboxy or amino (e.g., methyl, isopropyl, hydrogen), and $R_{53}$ and $R_{54}$ are hydrogen; or $R_{51}$ and $R_{53}$ taken together with the atoms on which they are attached form a 5-membered ring (e.g., a proline residue) and $R_{52}$ and $R_{54}$ are H. In another embodiment, $R_{51}$ and $R_{52}$ are independently selected from the group consisting of $C_{1-4}$alkyl optionally substituted by carboxy or amino (e.g., methyl, isopropyl, hydrogen), $R_{53}$ is hydrogen, and $R_{54}$ is —C(O)—$CR_{55}R_{56}$—$NR_{57}R_{58}$, wherein $R_{55}$ and $R_{56}$ are independently selected from the group consisting of $C_{1-4}$alkyl optionally substituted by carboxy or amino (e.g., methyl, isopropyl, hydrogen), and $R_{57}$ and $R_{58}$ are hydrogen; or $R_{55}$ and $R_{57}$ taken together with the atoms on which they are attached form a 5-membered ring (e.g., a proline residue) and $R_{56}$ and $R_{58}$ are H; or a pharmaceutically acceptable salt thereof.

Also provided herein are compounds represented by:

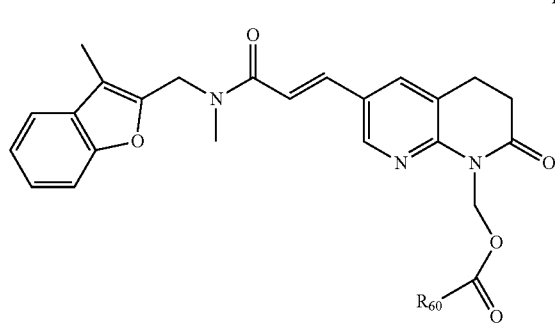

FF wherein $R_{60}$ is $NR_{61}R_{62}$, wherein $R_{61}$ and $R_{62}$ may each independently be selected from the group consisting of H, $C_{1-6}$alkyl (optionally substituted by phenyl), $C_{3-6}$cycloalkyl, and phenyl, or taken together with the nitrogen to which they are attached, form a 4-6 membered heterocyclic ring; or a pharmaceutically acceptable salt thereof.

In another embodiment, provided herein are compounds represented by:

GG

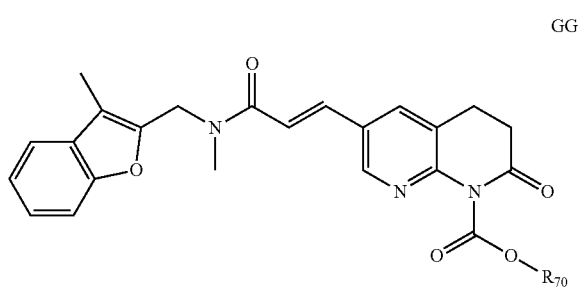

wherein R$_{70}$ is —CR$_{71}$R$_{72}$—O—R$_{73}$ wherein R$_{71}$ and R$_{72}$ may each independently be selected from the group consisting of H and C$_{1-6}$alkyl (optionally substituted by halo); and R$_{73}$ is selected from the group consisting of: —C(O)—(CH$_2$)$_t$—X$_7$; —P(O)(O—R$_{74}$)$_2$ and

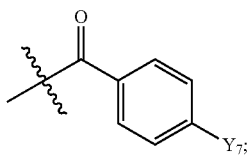

wherein t is 0, 1, 2, 3 or 4;

X$_7$ is selected from the group consisting of amino optionally substituted by one or two C$_{1-6}$alkyl, heterocyclyl optionally substituted by one or more C$_{1-6}$alkyl; and —O—PO$_3$H$_2$ or alkyl ester thereof;

Y$_7$ is selected from the group consisting of —CH$_2$—O—PO$_3$H or alkyl ester thereof, and —OPO$_3$H$_2$ or an alkyl ester thereof; and R$_{74}$, may be independently selected for each occurrence from H or C$_{1-6}$alkyl, or a pharmaceutically acceptable salt thereof.

In certain embodiments, for example, the compounds disclosed herein, once administered, possess improved bioavailability profiles when compared to (E)-N-methyl-N-((3-methylbenzofuran-2-yl)methyl)-3-(7-oxo-5,6,7,8-tetrahydro-1,8-naphthyridin-3-yl)acrylamide (compound IV) or salts thereof. For example, the compounds disclosed herein may possess at least 2-fold, at least 3-fold, at least 4-fold, at least 5-fold, at least 7-fold, at least 8-fold, at least 9-fold, at least 10-fold or at least 20-fold greater bioavailability as compared to (E)-N-methyl-N-((3-methylbenzofuran-2-yl)methyl)-3-(7-oxo-5,6,7,8-tetrahydro-1,8-naphthyridin-3-yl) acrylamide or salts thereof.

In certain embodiments, for example, the compounds disclosed, once administered, herein possess improved bioavailability profiles when compared to the p-toluenesulfonic salt of (E)-N-methyl-N-((3-methylbenzofuran-2-yl)methyl)-3-(7-oxo-5,6,7,8-tetrahydro-1,8-naphthyridin-3-yl)acrylamide. For example, the compounds disclosed herein may possess at least 2-fold, at least 3-fold, at least 4, fold, at least 5-fold, at least 7-fold, at least 8-fold, at least 9-fold, at least 10-fold or at least 20-fold greater bioavailability (e.g. oral bioavailability) as compared to the p-toluenesulfonic salt of (E)-N-methyl-N-((3-methylbenzofuran-2-yl)methyl)-3-(7-oxo-5,6,7,8-tetrahydro-1,8-naphthyridin-3-yl)acrylamide or salts thereof.

In another aspect, disclosed herein are pharmaceutical compositions comprising the compounds disclosed herein and a pharmaceutically acceptable excipient.

In certain embodiments, the composition is formulated for one of: intravenous administration, injectable administration, topical administration, systemic administration, aerosol administration to the respiratory epithelium, or oral administration. For example, provided here is a composition comprising a disclosed compound and pharmaceutically acceptable excipient or carrier suitable for oral administration, intravenous administration, subcutaneous administration, intranasal administration or a composition suitable for inhalation.

Methods

In another aspect, disclosed herein are methods of treating a bacterial infection, comprising administering to a patient in need thereof the pharmaceutical composition comprising a disclosed compound.

In a certain embodiment, disclosed herein is a method of treating a bacterial infection, comprising administering to a patient in need thereof a pharmaceutical composition that includes a disclosed compound, where when the compound is administered to said patient, provides a mean plasma level at least 2 times, at least 3 times, at least 4 times, at least 5 times, at least 7 times, at least 8 times, at least 9 times, at least 10 times or at least 20 times higher than that obtained by administering the same amount of (E)-N-methyl-N-((3-methylbenzofuran-2-yl)methyl)-3-(7-oxo-5,6,7,8-tetrahydro-1,8-naphthyridin-3-yl)acrylamide or salts thereof, on a molar basis, at about 4 hours after administration.

In another embodiment, disclosed herein is a method of treating a bacterial infection, comprising administering to a patient in need thereof a pharmaceutical composition that includes a disclosed compound, wherein when the disclosed compound is administered to said patient, provides a mean plasma level of (E)-N-methyl-N-((3-methylbenzofuran-2-yl)methyl)-3-(7-oxo-5,6,7,8-tetrahydro-1,8-naphthyridin-3-yl)acrylamide at least 2 times, at least 3 times, at least 4 times, at least 5 times, at least 7 times, at least 8 times, at least 9 times, at least 10 times or at least 20 times higher than that obtained by administering the same amount, on a molar basis, of p-toluenesulfonic acid salt of (E)-N-methyl-N-((3-methylbenzofuran-2-yl)methyl)-3-(7-oxo-5,6,7,8-tetrahydro-1,8-naphthyridin-3-yl)acrylamide, at about 4 hours after administration. In certain embodiments, the patient is a human.

Also provided herein is a method for treating cystic fibrosis in a patient in need thereof, comprising administering a disclosed compound. For example, provided here is a method of treating cystic fibrosis in a patient in need thereof comprising administering by inhalation a pharmaceutically effective amount of a composition comprising a disclosed compound. Alternatively, a method of treating cystic fibrosis in a patient in need thereof is provided, comprising orally, rectally or parenterally administering a disclosed compound.

In certain embodiments, disclosed herein are methods of treating a S. aureus infection (e.g., a methicillin-resistant S. aureus infection) in a patient in need thereof, comprising administering a disclosed compound. Other contemplated methods include treating H. influenza and/or P. aeruginosa infection in a patient in need thereof (e.g., a patient suffering from cystic fibrosis comprising administering an pharmaceutically effective amount of a disclosed compound.

For example, disclosed here is a method of treating a bacterial infection in a patient in need thereof comprising enterally (e.g., orally) administering a composition comprising a disclosed compound, e.g. compound 10. Such methods may further comprising administering, in a separate dosage form, an additional antibacterial or antibiotic agent as disclosed herein. Also disclosed here is a method of treating a bacterial infection in a patient in need thereof comprising parenterally (e.g., intravenously, intramuscularly, or subcutaneously) administering a composition comprising a disclosed compound, e.g. compound 10. In some embodiments, methods of treating a bacterial infection by systemically administrating a pharmaceutically effective amount of a disclosed compound are contemplated.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes, for example, subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

Topical administration is also contemplated, for example a method of treating an ophthalmic bacterial infection comprising topically an effective amount of a disclosed compound.

It will be appreciated that in certain embodiments, contemplated methods may include administration by inhalation or intratracheal instillation of a composition (e.g. an aerosolized, pH buffered composition) comprising a disclosed compound. The "term" inhaled administration" includes administration of a substantially uniform distribution of appropriately sized particles to the respiratory epithelium of the nose, central airways, the peripheral aspect of the lung and/or the alveolar region of the lung. Such particles may be introduced to the patient and/or produced using an appropriate device.

Disclosed methods may also include administration of one or more additional agents, e.g. further comprising administering one or more further antibiotic agent(s). For example, disclosed herein is method of treating a bacterial infection in a patient in need thereof, comprising administering an effective amount of a disclosed compound, and further administering (simultaneously or sequentially) one or more antibiotic agents or antibacterial agents selected from the group consisting of: vancomycin, clindamycin, macrolides, linezolid, sulfamethoxazole (and/or other sulfa agents), cephalosporins, carbapenems, tetracyclines, glycylcyclines, tobramicin, arbekacin, gentamicin, quinolones (e.g. fluoroquinolones, such as ciprofloxin, levofloxin) or pleuromutilins and combinations thereof. For example, provided herein is a method of treating an ophthalmic bacterial infection comprising topically administering an effective amount of a disclosed compound, and optionally further administering a fluoroquinolone and/or an aminoglycoside. In another embodiments, disclosed herein is method of treating or ameliorating cystic fibrosis in a patient in need thereof, comprising administering an effective amount of a disclosed compound, and further administering (simultaneously or sequentially) one or more therapeutic agents selected from the group consisting of: aztreonam, levofloxin, vancomycin, linezolid, sulfamethoxazole (and/or other sulfa agents), tobramicin, gentamicin, quinolone (e.g. fluoroquinolone) and combinations thereof.

Another aspect of the disclosure relates to a kit comprising the pharmaceutical composition comprising the disclosed compounds and instructions for use thereof.

Scheme 1 depicts an exemplary synthetic route and proposed mechanism for the in vivo processing of the disclosed compounds to the biologically active form, compound IV. Disclosed compounds can be administered in a water-solubilized chemical form. Once administered, the water-solubilized compound is metabolized in-vivo in systemic circulation and other extracellular fluid compartments to the active antibacterial of compound IV, for example as depicted in scheme 1:

Scheme 1

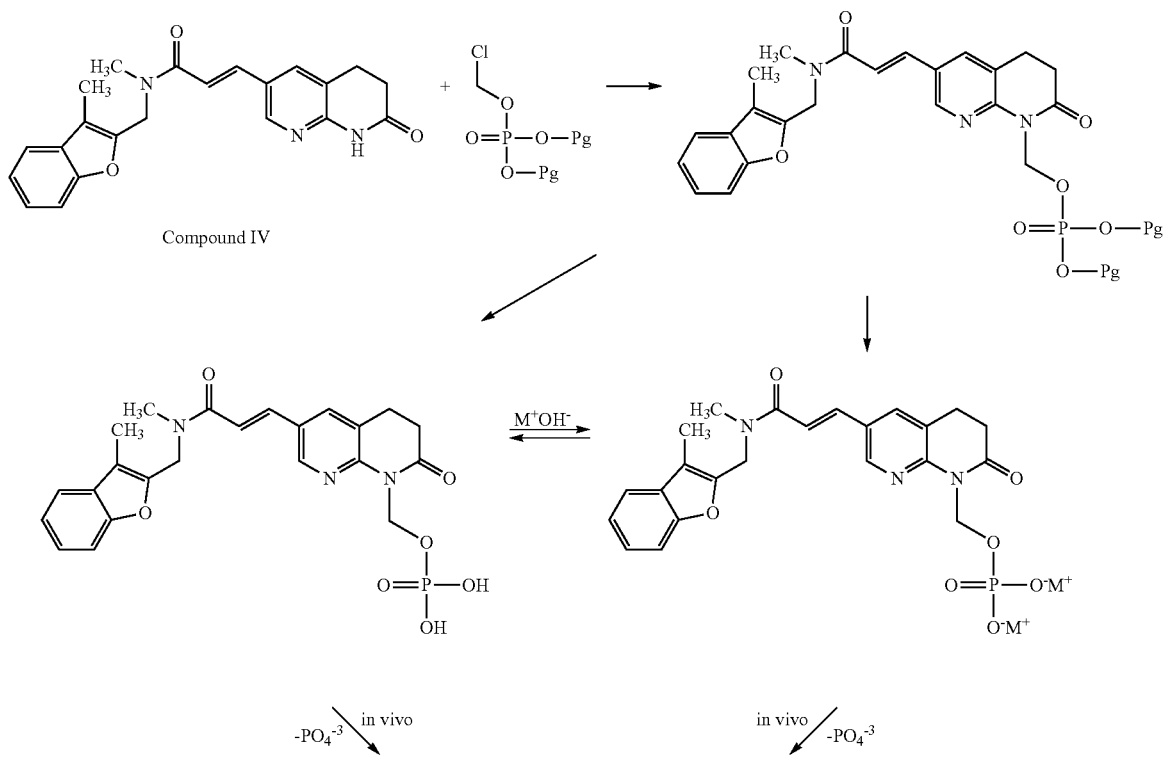

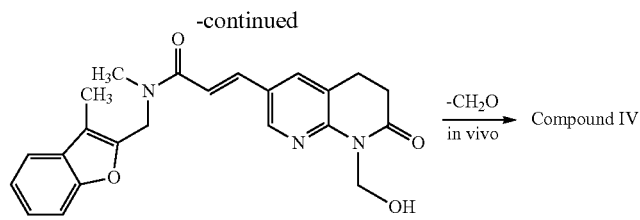

M⁺ is Na⁺, K⁺, etc

In certain embodiments, the compound below is contemplated. Such compound, without being limited by any theory, may also be a metabolite upon administration in certain patient species, such as dog:

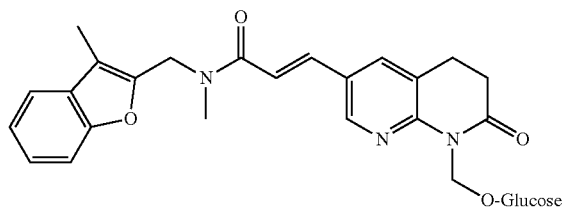

Yet another aspect of the disclosure relates to a method of preparing the compounds disclosed herein. In certain embodiment, the disclosure relates to a method of preparing a compound of formula II, comprising contacting the phosphate compound of formula III with a compound of formula IV, wherein formula II is represented by:

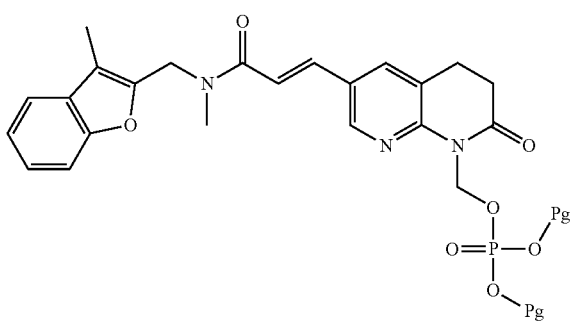

Formula III is represented by:

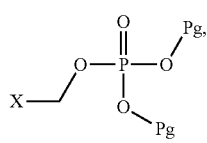

wherein:

X represents a leaving group; Pg represents a protecting group. Formula IV is represented by:

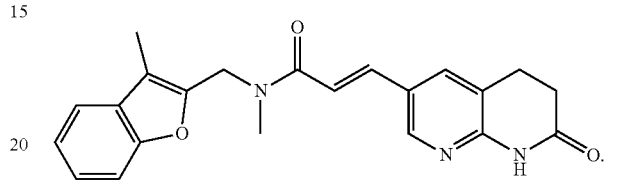

In certain embodiments, X is a halogen,

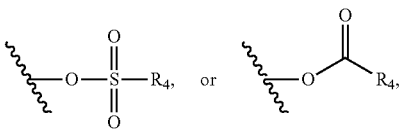

wherein $R_4$ is alkyl, aryl, aralkyl, or haloalkyl. In other embodiments, X is halogen. In certain other embodiments, X is chloride.

In certain embodiments, Pg is $C_{1-6}$alkyl-Si($R_5$)$_3$, wherein $R_5$ is $C_{1-6}$alkyl. In other embodiments, Pg is —(CH$_2$)$_2$—Si(CH$_3$)$_3$. In other embodiments, Pg is $C_{1-6}$alkyl, for example, t-butyl.

Pg may be aryl$C_{1-6}$alkyl, for example, benzyl. In another embodiment, Pg is $C_{1-6}$alkyloxycarbonyl, e.g., Pg may be t-butyloxycarbonyl.

In other embodiments, Pg is aryl$C_{1-6}$alkyloxycarbonyl. In other embodiments, Pg is benzyloxycarbonyl.

It will be appreciated that contacting the phosphate compound of formula III with a compound of formula IV may be conducted in the presence of a solvent, e.g., dimethylformamide (DMF) and/or tetrahydrofuran (THF). Contacting the phosphate compound of formula III with a compound of formula IV may further comprise adding a base such as potassium t-butoxide (KOtBu) and/or NaH.

In certain embodiments, the method further comprises contacting a Brønsted acid (for example, trifluoroacetic acid) and a compound of e.g., formula II to provide a compound of formula:

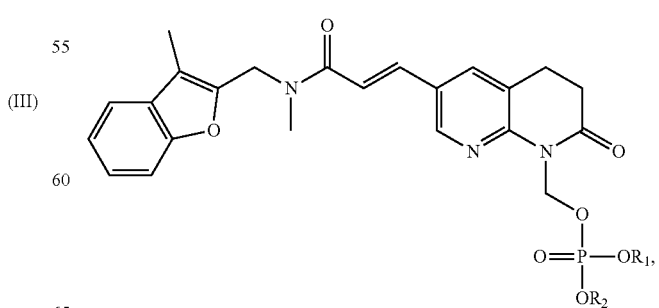

wherein $R_1$ and $R_2$ are described above.

In a similar manner and in some embodiments, compounds of formula BB-DD (for example) can be prepared using a reagent such as (in lieu of, e.g., formula III):

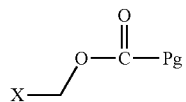

wherein:

X represents a leaving group (e.g. halogen such as Cl); Pg represents a protecting group (such as t-butyl or —O-ethyl).

Toxicology of Compounds

Acute toxicity can be assessed using increasing doses in mice and rodents. Exploratory acute toxicity in mice and/or rats after single dose may be undertaken to begin estimation of the therapeutic window of inhibitors and to identify the potential target organism of toxicity. As candidate selection nears, these studies may provide guidance for the selection of proper doses in multi-dose studies, as well as establish any species-specific differences in toxicities. These studies may be combined with routine pharmacokinetic (PK) measurements to assure proper dosages were achieved. Generally 3-4 doses will be chosen that are estimated to span a range having no effect through to higher doses that cause major toxic, but non-lethal, effects. Animals will be observed for effects on body weight, behavior and food consumption, and after euthanasia, hematology, blood chemistry, urinalysis, organ weight, gross pathology and histopathology will be undertaken.

Cytotoxicity Assays

Cytotoxicity of the new compounds may be evaluated by the Alamar Blue assay according the manufacturer's instructions. Human cell lines (e.g. Jurkat) grown in 96 well plates may be exposed to serial dilutions of the tested compounds. After adding Alamar Blue, cell viability may be determined by measuring the absorbance of the reduced and oxidized forms of Alamar Blue at 570 nm and 600 nm. Cytotoxicity may be reported as $LD_{50}$, the concentration that causes a 50% reduction in cell viability.

Dosages

The dosage of any disclosed compositions will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible effects on the timing of administration of the formulation, may need to be identified for any particular composition of the disclosure. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the disclosure, the therapeutically effective dose may be estimated initially from cell culture assays.

Compositions are also contemplated herein that include one or more of the disclosed compounds with a second component. Second components in such compositions of the present disclosure are usually an antibiotic agent other than a disclosed compound. Additional components may also be present, including FabI inhibitors or antibiotic agents. The contemplated methods of treatment disclosed herein, in some embodiments, may further comprise administering another agent such as one described below. For example, a method of treating a bacterial infection is provided that comprises administering a disclosed compound and further comprises administering an antibiotic agent or antibacterial agent described below.

Non-limiting examples of antibiotic agents that may be used in the antibacterial compositions of the disclosure include cephalosporins, quinolones and fluoroquinolones, penicillins, penicillins and beta lactamase inhibitors, carbepenems, monobactams, macrolides and lincosamines, glycopeptides, rifampin, oxazolidonones, tetracyclines, aminoglycosides, streptogramins, sulfonamides, and others. Each family comprises many members.

Cephalosporins can be further categorized by generation. Non-limiting examples of cephalosporins by generation include the following. Examples of cephalosporins—First generation compounds include Cefadroxil, Cefazolin, Cephalexin, Cephalothin, Cephapirin, and Cephradine. Second generation compounds include Cefaclor, Cefamandol, Cefonicid, Cefotetan, Cefoxitin, Cefprozil, Ceftmetazole, Cefuroxime, Cefuroxime axetil, and Loracarbef. —Third generation include Cefdinir, Ceftibuten, Cefditoren, Cefetamet, Cefpodoxime, Cefprozil, Cefuroxime (axetil), Cefuroxime (sodium), Cefoperazone, Cefixime, Cefotaxime, Cefpodoxime proxetil, Ceftazidime, Ceftizoxime, and Ceftriaxone. Fourth generation compounds include Cefepime.

Non-limiting examples of quinolones and fluoroquinolones include Cinoxacin, Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Trovafloxacin, Oxolinic acid, Gemifloxacin, and Pefloxacin.

Non-limiting examples of penicillins include Amoxicillin, Ampicillin, Bacampicillin, Carbenicillin Indanyl, Mezlocillin, Piperacillin, and Ticarcillin.

Non-limiting examples of penicillins and beta lactamase inhibitors include Amoxicillin-Clavulanic Acid, Ampicillin-Sulbactam, Benzylpenicillin, Cloxacillin, Dicloxacillin, Methicillin, Oxacillin, Penicillin G (Benzathine, Potassium, Procaine), Penicillin V, Piperacillin+Tazobactam, Ticarcillin+Clavulanic Acid, and Nafcillin. Non-limiting examples of carbepenems include Imipenem-Cilastatin and Meropenem.

A non-limiting example of a monobactam includes Aztreonam. Non-limiting examples of macrolides and lincosamines include Azithromycin, Clarithromycin, Clindamycin, Dirithromycin, Erythromycin, Lincomycin, and Troleandomycin. Non-limiting examples of glycopeptides include Teicoplanin and Vancomycin. Non-limiting examples of rifampins include Rifabutin, Rifampin, and Rifapentine. A non-limiting example of oxazolidonones includes Linezolid. Non-limiting examples of tetracyclines include Demeclocycline, Doxycycline, Methacycline, Minocycline, Oxytetracycline, Tetracycline, and Chlortetracycline.

Non-limiting examples of aminoglycosides include Amikacin, Arbakacin, Gentamicin, Kanamycin, Sisomicin, Arbekacin, Neomycin, Netilmicin, Streptomycin, Tobramycin, and Paromomycin. A non-limiting example of streptogramins includes Quinopristin+Dalfopristin.

Non-limiting examples of sulfonamides include Mafenide, Silver Sulfadiazine, Sulfacetamide, Sulfadiazine, Sulfamethoxazole, Sulfasalazine, Sulfisoxazole, Trimethoprim-Sulfamethoxazole, and Sulfamethizole.

Non-limiting examples of other antibiotic agents include Bacitracin, Chloramphenicol, Colistimethate, Fosfomycin, Isoniazid, Methenamine, Metronidazole, Mupirocin, Nitrofurantoin, Nitrofurazone, Novobiocin, Polymyxin B, Spectinomycin, Tobramycin, Tigecycline, Trimethoprim, Colistin, Cycloserine, Capreomycin, Pyrazinamide, para-Aminosalicyclic acid, and Erythromycin ethylsuccinate+sulfisoxazole.

Formulations

Pharmaceutical compositions of the disclosure may be administered by various means, depending on their intended use, as is well known in the art. For example, if compositions of the disclosure are to be administered orally, they may be formulated as tablets, capsules, granules, powders or syrups.

Alternatively, formulations disclosed herein may be administered parenterally as injections (intravenous, intramuscular or subcutaneous), drop infusion preparations or suppositories. For application by the ophthalmic mucous membrane route, the compositions disclosed herein may be formulated as eye drops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent. The disclosed excipients may serve more than one function. For example, fillers or binders may also be disintegrants, glidants, antiadherents, lubricants, sweeteners and the like.

In formulations of the disclosure, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal (e.g., by inhalation using a dry powder formulation or a nebulized formulation), topical (including buccal and sublingual), pulmonary (including aerosol administration), rectal, vaginal, aerosol and/or parenteral (e.g., by injection, for example, intravenous or subcutaneous injection) administration. The formulations may conveniently be presented in unit dosage form and may be prepared by any methods well known in the art of pharmacy. The amount of a composition that may be combined with a carrier material to produce a single dose vary depending upon the subject being treated, and the particular mode of administration.

Methods of preparing these formulations include the step of bringing into association compositions of the disclosure with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the disclosure may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, dextrose, lactose, sucrose, glucose, mannitol, and/or silicic acid; (2) binders, such as, for example, celluloses (e.g., microcrystalline cellulose, methyl cellulose, hydroxypropylmethyl cellulose (HPMC) and carboxymethylcellulose), alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8)

absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like. The disclosed excipients may serve more than one function. For example, fillers or binders may also be disintegrants, glidants, anti-adherents, lubricants, sweeteners and the like.

Formulations and compositions may include micronized crystals of the disclosed compounds. Micronization may be performed on crystals of the compounds alone, or on a mixture of crystals and a part or whole of pharmaceutical excipients or carriers. Mean particle size of micronized crystals of a disclosed compound may be for example about 5 to about 200 microns, or about 10 to about 110 microns.

A tablet may be made by compression or molding, optionally with one or more accessory ingredients. Compressed tablets may be prepared using binder (for example, gelatin, microcrystalline cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. The disclosed excipients may serve more than one function. For example, fillers or binders may also be disintegrants, glidants, anti-adherents, lubricants, sweeteners and the like.

It will be appreciated that a disclosed composition may include lyophilized or freeze dried compounds disclosed herein. For example, disclosed herein are compositions that disclosed compounds crystalline and/or amorphous powder forms. Such forms may be reconstituted for use as e.g., an aqueous composition.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, and patches. The active component may be mixed under sterile conditions with a pharmaceutically acceptable carrier, and with any preservatives, buffers, or propellants that may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It should be noted that excipients given as examples may have more than one function. For example, fillers or binders can also be disintegrants, glidants, anti-adherents, lubricants, sweeteners and the like.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. For example, provided herein is an aqueous composition that includes a disclosed compound, and may further include for example, dextrose (e.g., about 1 to about 10 weight percent dextrose, or about 5 weight percent dextrose in water (D5W).

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

It will be appreciated that contemplated formulations, such as oral formulations (e.g. a pill or tablet), may be formulated as controlled release formulation, e.g., an immediate release formulation, a delayed release formulation, or a combination thereof.

In certain embodiments, the subject compounds may be formulated as a tablet, pill, capsule or other appropriate ingestible formulation (collectively hereinafter "tablet"). In certain embodiments, a therapeutic dose may be provided in 10 tablets or fewer. In another example, a therapeutic dose is provided in 50, 40, 30, 20, 15, 10, 5 or 3 tablets.

In a certain embodiment, a disclosed compound is formulated for oral administration as a tablet, capsule, or an aqueous solution or suspension. In another embodiment of a tablet form the tablets are formulated such that the resulting amount of antibacterial agent (or antibacterial agents) provided in 20 tablets, if taken together (e.g., over time) once administered, would provide a dose of at least the median effective dose ($ED_{50}$), e.g., the dose at which at least 50% of individuals exhibited the quantal effect of inhibition of bacterial cell growth or protection (e.g., a statistically significant reduction in infection). In a further embodiment, tablets may be formulated such that the total amount of antibacterial agent (or antibacterial agents) provided upon administration in 10, 5, 2 or 1 tablets would provide at least an $ED_{50}$ dose to a patient (human or non-human mammal). In other embodiments, the amount of antibacterial agent (or antibacterial agents) provided, upon administration, in 20, 10, 5 or 2 tablets taken in a 24 hour time period would provide a dosage regimen providing, on average, a mean plasma level of the antibacterial agent(s) of at least the $ED_{50}$ concentration (the concentration for 50% of maximal effect of, e.g., inhibiting bacterial cell growth). In other embodiments less than 100 times, 10 times, or 5 times the $ED_{50}$ is provided. In other embodiments, a single dose of tablets (1-20 tablets) provides about 0.25 mg to 1250 mg of compound(s).

Likewise, compounds disclosed herein can be formulated for parenteral administration, as for example, for subcutaneous, intramuscular or intravenous injection, e.g., the antibacterial agent can be provided in a sterile solution or suspension (collectively hereinafter "injectable solution"). The injectable solution may be, in some embodiments, formulated such that the amount of antibacterial agent (or antibacterial agents) provided in, for example, in about 0.1 to about 200 cc bolus injection, or a dose administered intravenously, would provide a dose of at least the median effective dose, or less than 100 times the $ED_{50}$, or less than 10 or 5 times the $ED_{50}$. The injectable solution may be formulated such that the total amount of antibacterial agent (or antibacterial agents) provided (upon administration) in 100, 50, 25, 10, 5, 2.5, or 1 cc injections would provide an $ED_{50}$ dose to a patient, or less than 100 times the $ED_{50}$, or less than 10 or 5 times the $ED_{50}$. In other embodiments, the amount of antibacterial agent (or antibacterial agents) provided, upon administration, in a total volume of 100 cc, 50, 25, 5 or 2 cc to be injected at least twice in a 24 hour time period would provide a dosage regimen providing, on average, a mean plasma level of the antibacterial agent(s) of at least the $ED_{50}$ concentration, or less than 100 times the $ED_{50}$, or less than 10 or 5 times the $ED_{50}$. In other embodiments, a single dose injection provides about 0.25 mg to 1250 mg, or about 0.25 mg to about 2500 mg of antibacterial agent.

Kits

This disclosure also provides kits for conveniently and effectively implementing the methods disclosed herein. Such kits comprise any subject composition, and a means for facilitating compliance with methods disclosed herein. Such kits provide a convenient and effective means for assuring that the subject to be treated takes the appropriate active in the correct dosage in the correct manner. The compliance means of such kits includes any means which facilitates administering the actives according to a method disclosed herein. Such compliance means include instructions, packaging, and dispensing means, and combinations thereof. Kit components may be packaged for either manual or partially or wholly automated practice of the foregoing methods. In other embodiments involving kits, the disclosure contemplates a kit including compositions disclosed herein, and optionally instructions for their use.

The examples which follow are intended in no way to limit the scope of the disclosure but are provided to illustrate how to prepare and use compounds disclosed herein. Many other embodiments of this disclosure will be apparent to one skilled in the art.

EXAMPLES

Example 1: Synthesis of Various Salt Forms of (E)-(6-[N-(methyl-((3-methylbenzofuran-2-yl)methyl)amino)-3-oxoprop-1-en-1-yl)-2-oxo-3,4-dihydro-1,8-naphthyridin-1(2H)-yl]methyl phosphate—Compound V The compounds were prepared according to the procedures described below and as shown in Scheme 2.

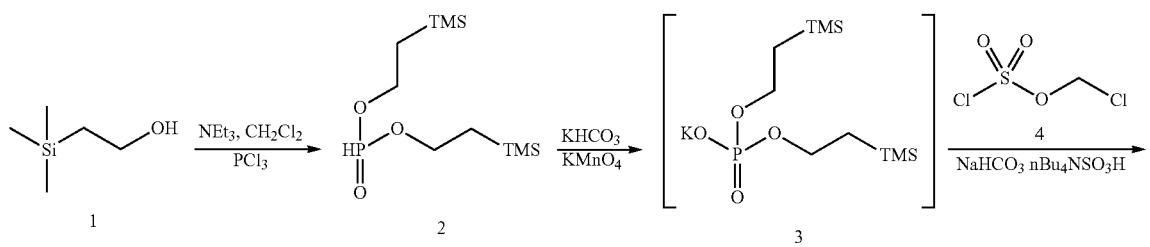

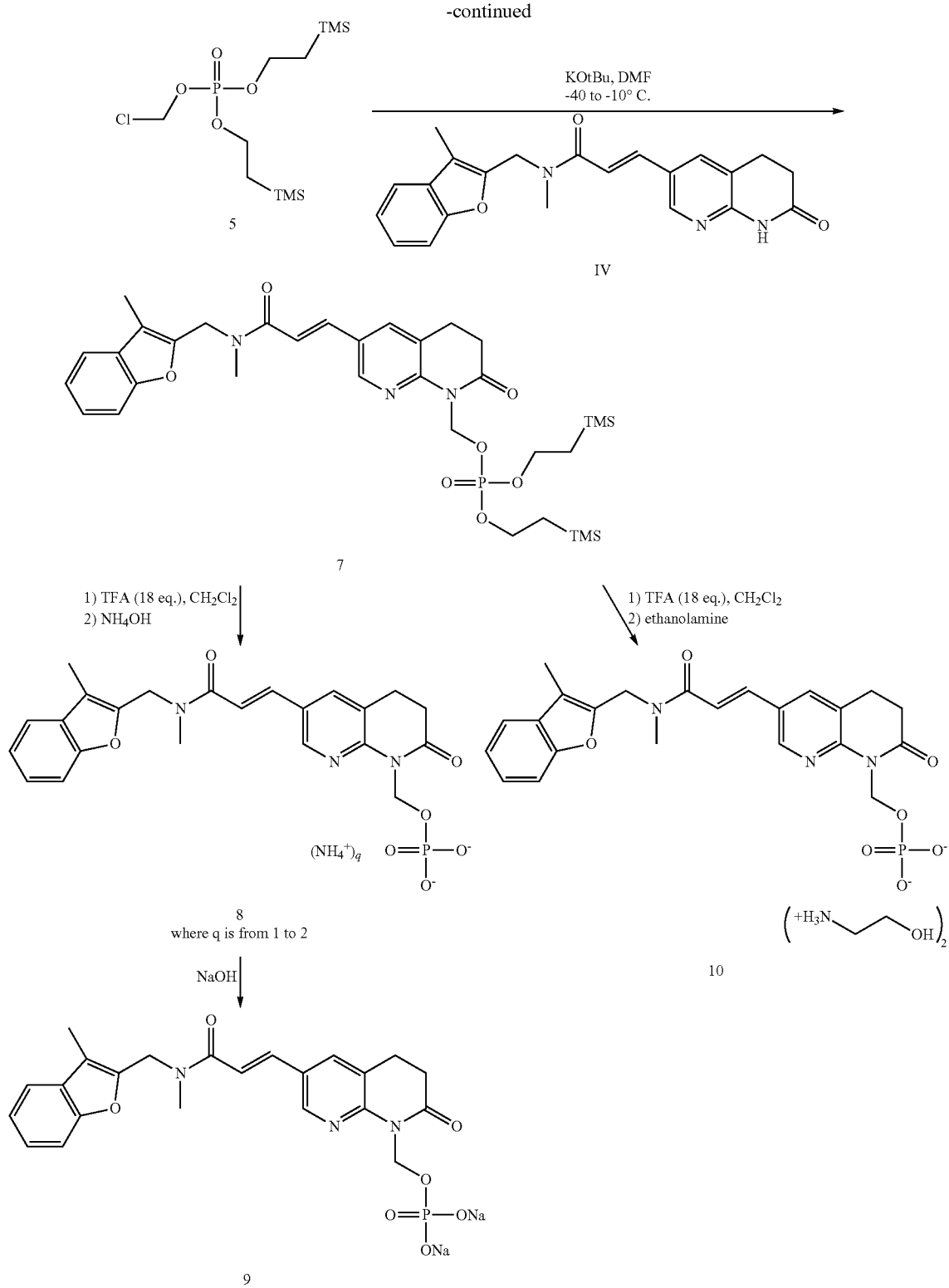

Synthesis of Compound 2

Phosphorus trichloride (49.2 mL, 564 mmol) was added dropwise to a 0° C. solution of trimethylsilylethanol, compound 1, (200 g, 1.69 mol, 3 eq.) and triethylamine (160 mL, 1.15 mol, 2 eq.) in 3.5 L dichloromethane. An exotherm was observed so the addition had to be slow enough to maintain the temperature below 10° C. Upon complete addition, triethylamine hydrochloride precipitated and the thick slurry was stirred for 30 minutes at 0° C., then 30 minutes at room temperature. Water (1 L) was added to clarify the solution, and the clear two-phase solution was stirred for one hour at room temperature. The organic layer was separated, washed with water, dried over anhydrous sodium sulfate, filtered and the filtrate concentrated under vacuum at 25-50° C. to remove residual volatiles. The reaction afforded 150 g (99%) of compound 2. $^1$H NMR of the material indicated >95% purity.

Compound 2 $^1$H NMR (400 MHz, CDCl$_3$): δ 7.68 and 5.95 (2s, 1H), 4.19 (m, 4H), 1.10 (m, 4H), 0.05 (s, 18H).

Synthesis of Compound 5

Phosphinic acid compound 2 (110 g in 2.5 L of water, 390 mmol) was added to 2.5 L of water and potassium bicarbonate (22 g, 220 mmol, 0.56 eq.). The solution was placed in a 25° C. water bath and potassium permanganate (80 g, 506 mmol, 1.3 eq.) was added in four 20 g portions every twenty minutes so as not to allow the temperature of the solution to exceed 40° C. The slurry was then heated to 50° C. for 30 minutes and then filtered hot using a Buchner funnel and filter paper. To the clear aqueous filtrate solution was added sodium bicarbonate (115 g, 1365 mmol, 3.5 eq.) followed by tetrabutylammonium hydrogensulfate (13.3 g, 39 mmol, 0.1 eq.). Dichloromethane (1.5 L) was added and the solution was cooled to 0° C. to which 47 mL (468 mmol, 1.2 eq.) of chloromethyl chlorosulfate, 4 was added slowly. The slurry was stirred for 12 hours as it warmed to room temperature. The organic layer was separated and the aqueous layer was extracted once more with dichloromethane (0.5 L). The combined organic layers were dried over anhydrous sodium sulfate and concentrated in vacuo to yield the crude product which was purified by flash chromatography (25% EtOAc/hexanes with 3% NEt$_3$) to yield 75 g (55% yield) of compound 5 as a colorless oil which was >95% pure as indicated by $^1$H NMR.

Compound 5: $^1$H NMR (400 MHz, CDCl$_3$): δ 5.68 (d, 2H), 4.20 (m, 4H), 1.13 (m, 4H), 0.05 (s, 18H).

Synthesis of Compound IV Free Base

Compound IV as the tosylate monohydrate salt (100 g, 183 mmol) was placed in methanol (3 L) and ethyl acetate (500 mL) and heated to 65° C. over a 2-hour period. To the hot suspension was added sodium hydroxide (150 mL of a 2N solution, 300 mmol) and the resultant slurry was stirred for 30 minutes. The reaction was cooled to room temperature and the solid was filtered. The solid was washed with water (2×500 mL) followed by ether (500 mL). The white cake was dried under vacuum overnight to yield 61.7 g (90% yield) of pure compound IV free base as an off-white solid.

Compound IV (free base): $^1$H NMR (400 MHz, DMSO d$_6$): δ 10.65 (s, 1H), 8.36 (m, 1H), 8.08 (m, 1H), 7.58-7.18 (m, 6H), 5.00, 4.80 (2s, 2H), 3.18 (s, 2H), 2.92 (m, 3H), 2.50 (m, 2H), 2.25 (s, 3H).

Synthesis of Compound 7

Compound IV free base (37.5 g, 100 mmol) was placed in DMF (1000 mL), cooled to −40° C. and KOtBu (12.3 g, 110 mmol, 1.1 eq.) was added in portions. The solution was stirred for 90 minutes upon which compound 5 (64 g, 184 mmol, 1.84 eq., dissolved in 50 mL of DMF), was added over 15 minutes. The yellow orange solution was stirred for an additional two hours as it warmed to −28° C. The dark orange solution was stirred for 1.5 hours as it warmed to −10° C. and then a further 1.5 hours as it warmed to −5° C. The reaction was quenched with dilute aqueous ammonium chloride (1 L) followed by water (2 L) and the organic layer was extracted twice with ethyl acetate (EtOAc, 2 L). The organic phases were back-extracted with water (1 L), dried over anhydrous sodium sulfate, filtered and concentrated in vacuo, to give the crude product which was purified by flash chromatography (1 kg of silica gel using 50-100% EtOAc/hexanes) to yield 41 g (60% yield) of pure 7 as a viscous bright yellow oil.

Compound 7 $^1$H NMR (400 MHz, DMSO d$_6$): δ 8.52 (d, 1H), 8.20 (d, 1H), 7.55-7.21 (m, 6H), 5.93 (s, 2H), 5.00-4.80 (2s from rotamers, 2H), 4.00 (m, 4H), 3.18-2.92 (2s from rotamers, 3H), 2.92 (m, 2H), 2.25 (s, 3H), 0.97 (t, 4H), 0.00 (s, 18H).

Analogs of compound 7 (as represented by Formula II, above) may be prepared using different analogs of compound 5, (as represented by Formula III, above) together with a solvent and a base, as described above. The table below indicates the significance of compound 5. Different Pg's used in compound III to produce compound II are shown below.

| Pg | Base | Solvent | Comments |
| --- | --- | --- | --- |
| CH$_2$CH$_2$TMS | KOtBu | DMF | 50% (large scale) to 70% (small scale) conversion |
| Ethyl | KOtBu | DMF | No detectable product |
| tert-butyl | KOtBu | DMF | No detectable product |
| Benzyl | KOtBu | DMF | No detectable product |
|  | NaH | THF | No detectable product |

Synthesis of Compound 8

Compound 7 (96 g, 140 mmol) was dissolved in dichloromethane (560 mL), cooled to −25° C. and trifluoroacetic acid (187 mL, 2520 mmol, 18 eq.) in 85 mL of dichloromethane was added slowly over 15 minutes while maintaining the temperature below −15° C. The solution was stirred for 45 minutes as it warmed to −5° C., then re-cooled to −35° C. and 300 mL of 10M NH$_4$OH in 350 mL of water was added slowly over 20 minutes while maintaining the temperature below 0° C. The solution was warmed to room temperature, the volatile dichloromethane solvent was removed in vacuo and the resulting milky aqueous solution was filtered to remove insoluble reaction by-products. The filtrate was concentrated in vacuo using added toluene (2×1 L) to remove residual water, yielding a pale yellow sticky solid. This solid was suspended in 95% ethanol (3.5 L) and stirred for 3 hours at 60° C., followed by stirring at room temperature for overnight. The solid was then filtered, air dried, suspended in 95% ethanol (3.5 L) and isolated by filtration to produce a pale yellow brittle solid powder. The solid was ground to a fine off-white powder with a mortar and pestle to provide 43 g (88.6 mmol, 63% yield) of Compound 8 ((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate ammonium salt) at >98% purity by HPLC. Note: the number of ammonium cations in 8 was unknown.

Compound 8: $^1$H NMR (400 MHz, DMSO d$_6$): δ 8.49 (d, 1H), 8.10 (d, 1H), 7.55-7.10 (m, 6H), 5.70 (s, 2H), 4.98-4.77 (2s from rotamers, 2H), 3.18-2.90 (2s from rotamers, 3H), 2.88 (m, 2H), 2.63 (m, 2H), 2.25 (s, 3H).

Synthesis of Compound 9

Compound 8 (23.7 g, 45.6 mmol) was placed in water (300 mL) and sodium hydroxide (880 mL of a 0.1N solution, 88 mmol, 96% of theoretical for each acid unit) was added slowly over 5 minutes. The resulting solution was filtered to remove particulates. The aqueous solution was then freeze dried in vacuo over 3 days to yield compound 9 (23.6 g, 99%) as an off-white fluffy powder which was pure (>98%) by HPLC and $^1$H NMR. Compound 9 is ((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate disodium salt).

Compound 9 $^1$H NMR (400 MHz D$_2$O): δ 8.03 (s, 1H), 7.50-6.60 (m, 7H), 5.32 (m, 2H), 4.48-4.42 (2s from rotamers, 2H), 2.88-2.80 (2s from rotamers, 3H), 2.70-2.21 (m, 4H), 1.85 (2s from rotamers, 3H).

Recrystallization of Compound 9

Compound 9 (1.2 g, 2.27 mmol) was added to water (16 mL) and lowered into a 70° C. oil bath. The compound dissolved in less than 2 minutes. Then isopropyl alcohol (40 mL) was added, the heating and stirring were stopped and the mixture was left to stand overnight to induce precipitation. The next day a white suspension was obtained. The suspension was stirred for 15 minutes, filtered, and the solid was washed with isopropyl alcohol, air dried, then pumped under high vacuum giving 0.790 g of 9 as a white crystalline solid compound 9 (>98%) by HPLC and $^1$H NMR.

Alternative Synthetic Route to Compound 9

Compound 8 (2 g, 3.85 mmol) was placed in a round bottom flask and 0.5N NaOH (14.6 mL, 7.3 mmol) was added. The mixture was heated at 75° C. in an oil bath for approximately 2 minutes. The resulting solution was filtered on a Buchner filter. The filter was and rinsed with water and isopropyl alcohol. The filtrate and washings was stirred at room temperature and some seed crystals were added to the solution. The crude compound 9 oiled out on the surface of the round bottom flask. Upon stirring, the oil solidified into a white solid. This white suspension was stirred for 2 hours, and then filtered. The isolated solid was washed with isopropyl alcohol (2×), air dried, then pumped under high vacuum overnight, giving 1.76 g (3.33 mmol) of compound 9 as a white powder which was pure (>98%) by HPLC and $^1$H NMR.

Synthesis of Compound 10

Compound 7 (38.4 g, 55.9 mmol) was dissolved in dichloromethane (233 mL) and cooled to −20° C. (bath temperature). Trifluoroacetic acid (74.7 mL, 18 eq., 1 mol) in dichloromethane (50 mL) was slowly added to the mixture. The mixture was stirred at −2 to 0° C. for 15 minutes then cooled to <−30° C. (bath temperature) and ethanolamine (70.9 mL, 1.17 mol) in dichloromethane (150 mL) was slowly added. The cold bath was then removed and the mixture left to warm to room temperature for 1 hour. The mixture solidified as a crystalline mass and was diluted with dichloromethane (500 mL) and filtered. The isolated solid was washed with dichloromethane (200 mL) and air dried. The solid was stirred overnight in isopropyl alcohol (700 mL), filtered, washed with isopropyl alcohol and air dried. The resultant solid was again stirred overnight in isopropyl alcohol (700 mL), filtered, washed with isopropyl alcohol and air dried. Separately, the above sequence was performed again with a separate batch of Compound 7 (38.4 g, 55.9 mmol) and the combined solids were then stirred overnight in isopropyl alcohol (700 mL), filtered, washed with isopropyl alcohol and air dried. The combined solid from the two batches was then placed in a 65° C. water bath and stirred in 95% ethanol (1 L) overnight as it cooled to room temperature to effect crystallization. The solid was isolated by filtration, washed with isopropyl alcohol and air dried. The solid was then again placed in a 65° C. water bath and stirred in 95% ethanol (1 L) overnight as it cooled to room temperature to effect crystallization. The solid was isolated by filtration, rinsed with isopropyl alcohol and air dried. The solid was suspended in water (200 mL) and heated at 50° C. until the entire solid dissolved. The solution was then filtered to remove all insoluble solid impurities. The resulting filtrate was diluted with isopropyl alcohol (2.4 L) until the solid began to precipitate and the slurry was stirred overnight to effect crystallization. Finally, the suspension was filtered and the solid was washed with isopropyl alcohol (200 mL) and dried to give the desired product as a white solid. The compound was pure (>98%) by HPLC and $^1$H NMR. $^{19}$F NMR against an internal standard (CF$_3$CH$_2$OH) indicated <500 ppm of residual trifluoroacetate salts. The purified solid was then ground to a fine powder and placed under vacuum overnight to give 46.1 g (68% yield) of white crystalline solid compound 10 ((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate bis-ethanolammonium salt). The compound was pure (>98%) by HPLC and $^1$H NMR. $^{19}$F NMR against an internal standard (CF$_3$CH$_2$OH) indicated <1000 ppm of residual trifluoroacetate salts.

Compound 10 $^1$H NMR (400 MHz, DMSO d$_6$ at 80° C.): δ 8.42 (s, 1H), 8.00 (s, 1H), 7.55 (d, 1H), 7.50 (s, 1H), 7.45 (s, 1H), 5.65 (s, 2H), 4.45 (bs, 2H), 3.60-3.40 (m, 8H), 3.10 (bs, 2H), 2.90 (t, 2H), 2.60 (t, 2H), 2.45 (s, 3H), 2.20 (s, 3H). Compound 10 $^{13}$C NMR (500 MHz, D$_2$O): δ When a chemical shift has the sign "(d)" it denotes rotamers causing doubling of the carbon signals: 173(d), 166(d), 153, 151, 148, 146(d), 139, 134(d), 129(d), 126, 124(d), 122(d), 121(d), 119(d), 117(d), 113(d), 110(d), 65, 57, 43(d), 41, 35(d), 30, 22, 7.0. Melting Point: 183° C. decomposes at 220° C.

Synthesis of Compound 9 from Compound 10

Compound 10 (490 mg, 0.81 mmol) was placed in a round bottom flask, to which was added 0.5N sodium hydroxide (3.05 mL, 1.53 mmol) and the flask lowered into a 75° C. bath. Water (2.53 mL) was then added to the solution, followed by isopropyl alcohol (25.2 mL). The homogeneous mixture was stirred at room temperature overnight and some seed crystals were added. After standing overnight, the compound oiled out on the surface of the round bottom flask. More seed solids were added to the flask, and the flask was cooled over dry ice. After a white solid started to form, the mixture was stirred for 3 hours at room temperature. The solids were filtered, washed with isopropyl alcohol (2×20 mL), air dried, and then pumped under high vacuum affording 329 mg of a white powder compound 9 which was pure by $^1$H NMR.

Synthesis of Compound 11

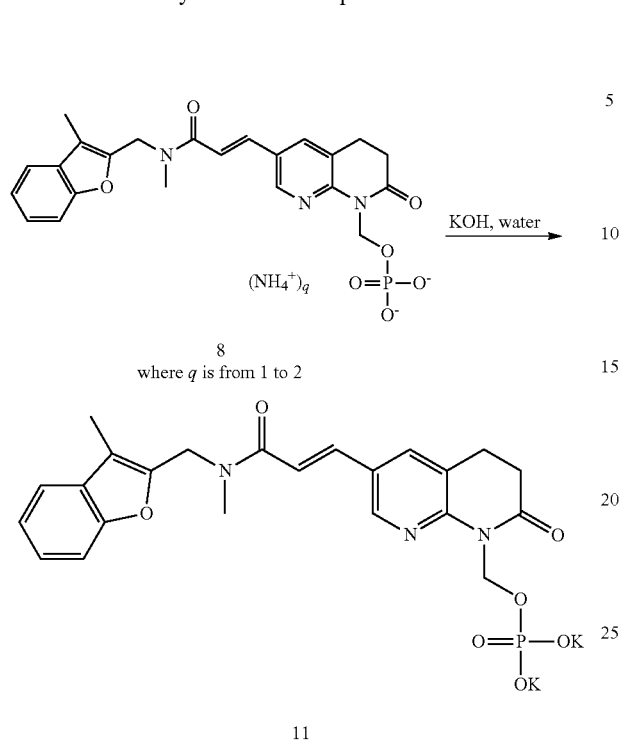

where q is from 1 to 2

Compound 8 (1.11 g, 2.29 mmol) was placed in water (100 mL) and potassium hydroxide (43.5 mL of a 0.1N solution, 4.35 mmol) was added slowly over 5 minutes. All the solids went into solution and the clear solution was filtered through filter paper to remove particulates. The aqueous solution was then freeze dried in vacuo over 2 days to yield Compound 11 (E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate dipotassium salt) (1.11 grams) as a white fluffy powder was pure (>98%) by HPLC and 1H NMR.

Compound 11 $^1$H NMR (400 MHz, D$_2$O): δ 8.00 (s, 1H), 7.47-6.58 (m, 7H), 5.50 (m, 2H), 4.47-4.42 (2s from rotamers, 2H), 2.85-2.78 (2s from rotamers, 3H), 2.68-2.40 (m, 4H), 1.92-1.90 (2s from rotamers, 3H).

Synthesis of Compound 12

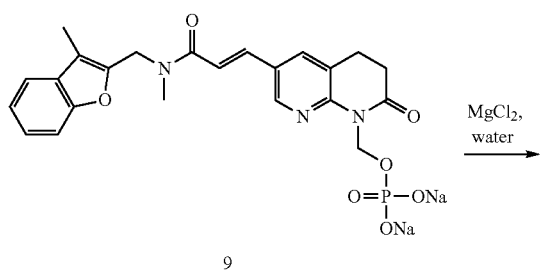

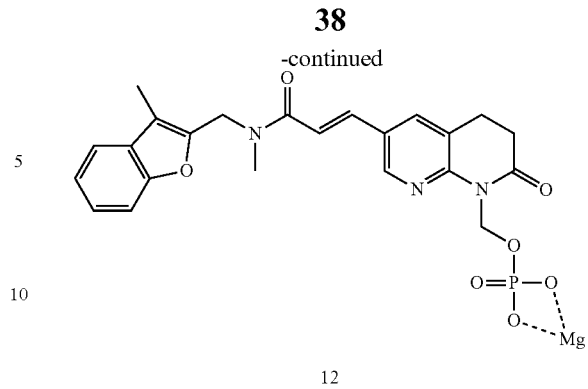

Compound 9 (200 mg, 0.38 mmol) was placed in water (12 mL) and magnesium chloride hexahydrate (85 mg, 0.42 mmol in 4 mL water) was added slowly. A white solid began to appear almost immediately, the mixture was stirred overnight, the solid filtered, washed with water, air dried and then pumped under high vacuum to yield 12 (120 mg) as a white powder which could not be fully analyzed by HPLC or $^1$H NMR spectra due to insolubility. Compound 12 is (E)-6-[(N-methyl-((3-methylbenzofuran-2-yl)methyl)amino)-3-oxoprop-1-en-1-yl)-2-oxo-3,4-dihydro-1,8-naphthyridin-1 (2H)-yl]methylphosphate magnesium salt.

Synthesis of Compound 13

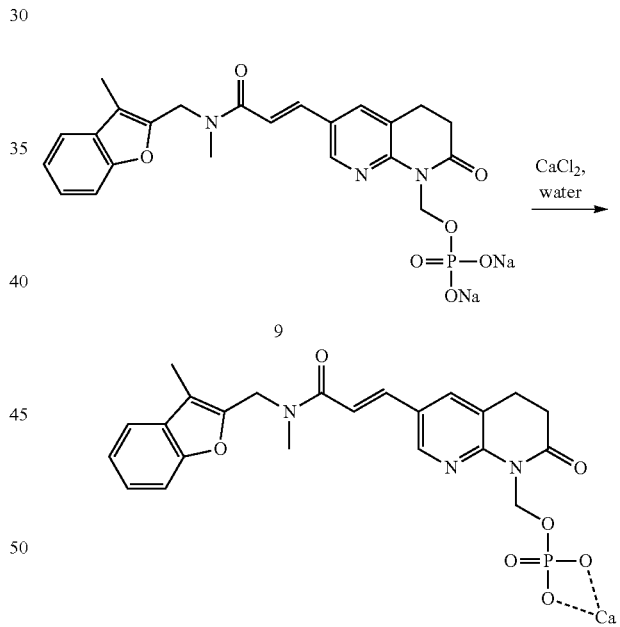

Compound 9 (200 mg, 0.38 mmol) was placed in water (12 mL) and calcium chloride dihydrate (61 mg, 0.41 mmol in 4 mL water) was added slowly. A white solid was formed and the mixture was stirred overnight. The resulting white solid was filtered, washed with water, air dried and then pumped under high vacuum to yield 13 ((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate calcium salt) as a white powder (100 mg) which could not be fully analyzed by HPLC or $^1$H NMR due to its insolubility.

Preparation of Compound 14

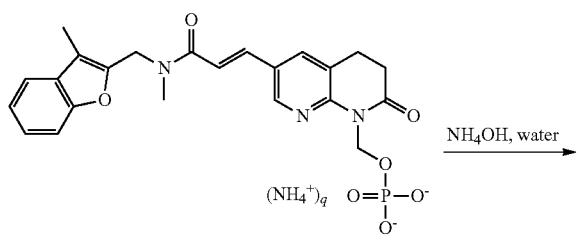

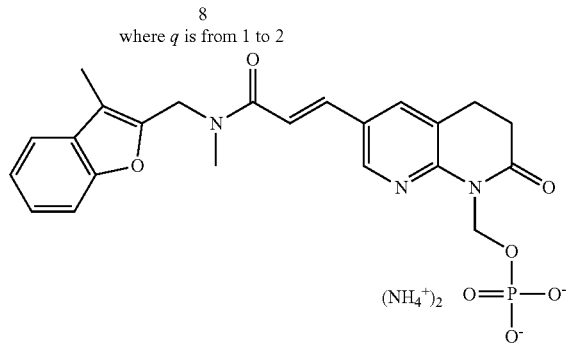

Compound 8 (1.11 g, 2.29 mmol) was placed in water (100 mL) and ammonium hydroxide 0.1M (23 mL, 2.3 mmol) was added slowly. All the solids went into solution and the clear solution was filtered through filter paper to remove particulates. The aqueous solution was then freeze dried over 2 days to yield 14 (1.1 grams) as a white fluffy amorphous powder which was analytically pure (>98%) by HPLC and 1H NMR. Compound 14 ((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methyl-phosphate diammonium salt) is a more water-soluble amorphous form compared to less water soluble compound 8.

Compound 14: 1H NMR (400 MHz, $D_2O$): δ 8.10 (d, 1H), 7.63-6.75 (m, 7H), 5.62 (m, 2H), 4.52 (s, 2H), 2.95-2.87 (2s from rotamers, 3H), 2.77-2.50 (m, 4H), 2.05-2.03 (2s from rotamers, 3H).

Synthesis of Compound 15

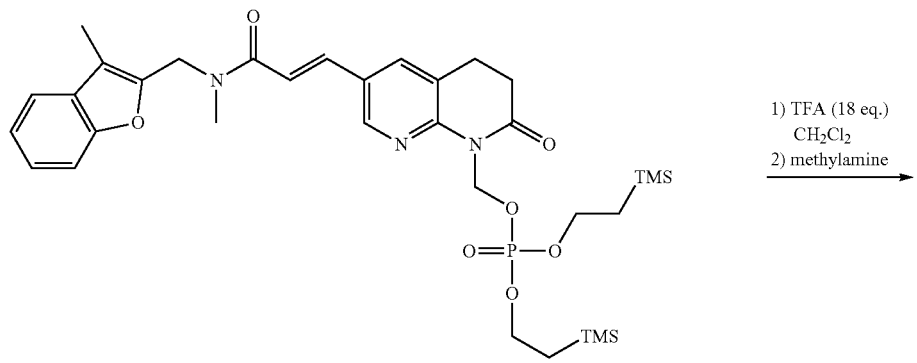

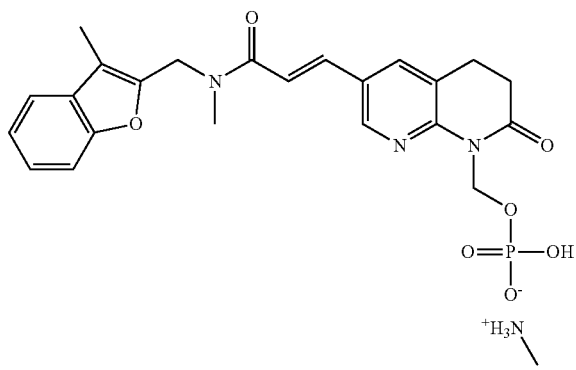

Compound 7 (1 g, 1.46 mmol) was dissolved in dichloromethane (6 mL) and cooled to −10° C. (bath temperature), to this was slowly added trifluoroacetic acid (1.95 mL, 26.2 mmol) in dichloromethane (0.9 mL). The mixture was stirred at −10° C. for 15 minutes then cooled to <−30° C. (bath temperature) and methylamine (40% in water/3.88 mL) was slowly added. The cold bath was then removed and the mixture left to warm to room temperature. The mixture was concentrated, suspended in toluene and concentrated (repeated 4×) to remove water and the residue pumped under high vacuum to dryness. The residue was stirred overnight in 5% isopropanol/diethyl ether, the solid filtered, stirred in (5% isopropanol/diethylether) and the solid filtered. The solid obtained was then suspended and stirred in 30 mL of isopropyl alcohol (60° C. 1 hr, then 3 days at room temperature) filtered and the solid stirred in 30 mL of isopropyl alcohol (60° C. 4 hr, then room temperature overnight) and filtered. This solid was then washed with isopropanol, air dried and vacuum dried yielding 330 mg of compound 15 as a white powder which was analytically pure (>97%) by HPLC and $^1$H NMR. ((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate monobasic methylammonium salt.)

Compound 15 $^1$H NMR (400 MHz, D$_2$O): δ 7.87 (d, 1H), 7.22-6.35 (m, 7H), 5.45 (br s, 2H), 4.30-4.22 (2s from rotamers, 2H), 2.64-2.62 (2s from rotamers, 3H), 2.50-2.27 (m, 7H), 1.75-1.70 (2s from rotamers, 3H).

Synthesis of Compound 16

Compound 7 (2.1 g, 3.06 mmol) was dissolved in dichloromethane (12 mL) and cooled to −10° C. (bath temperature), to this was slowly added trifluoroacetic acid (4.09 mL, 55 mmol) in dichloromethane (2 mL). The mixture was stirred at −10° C. for 15 minutes then cooled to <−30° C. (bath temperature) and dimethylamine (40% in water, 1.9 mL) was slowly added. The cold bath was then removed and the mixture left to warm to room temperature. The mixture was concentrated, diluted with toluene and concentrated (repeated 4×) to remove water, and the residue pumped under high vacuum to dryness. The residue was stirred overnight in 5 mL isopropanol/50 mL diethylether, and the solid filtered. The solid residue obtained was then suspended in 60 mL of isopropyl alcohol (65° C. for 2 hours followed by room temperature overnight), filtered, washed with isopropyl alcohol, air dried, and this purification process was repeated a second time. The solid was pumped under high vacuum overnight giving 732 mg of Compound 16 as a white powder. ((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate monobasic dimethylammonium salt).

Compound 16: 1H NMR (400 MHz, D$_2$O): δ 7.92 (s, 1H), 7.33-6.43 (m, 7H), 5.50 (s, 2H), 4.35-4.30 (2s from rotamers, 2H), 2.75-2.73 (2s from rotamers, 3H), 2.58-2.27 (m, 10H), 1.82 (s, 3H).

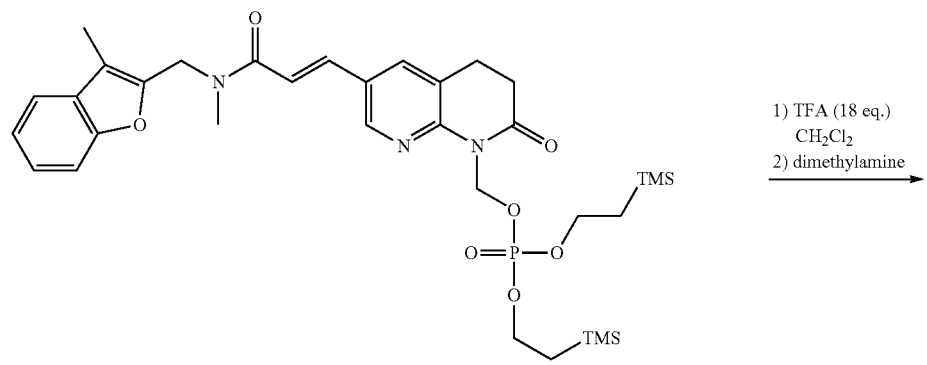

7

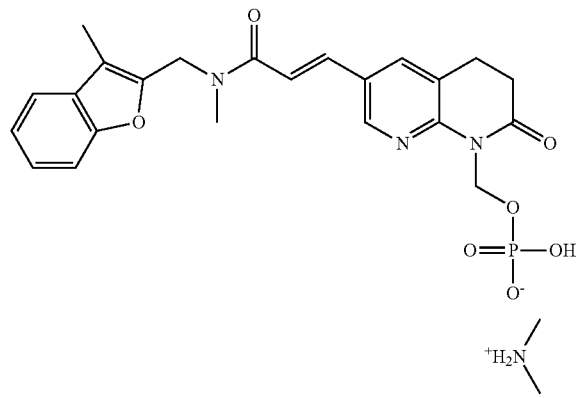

16

Synthesis of Compound 17

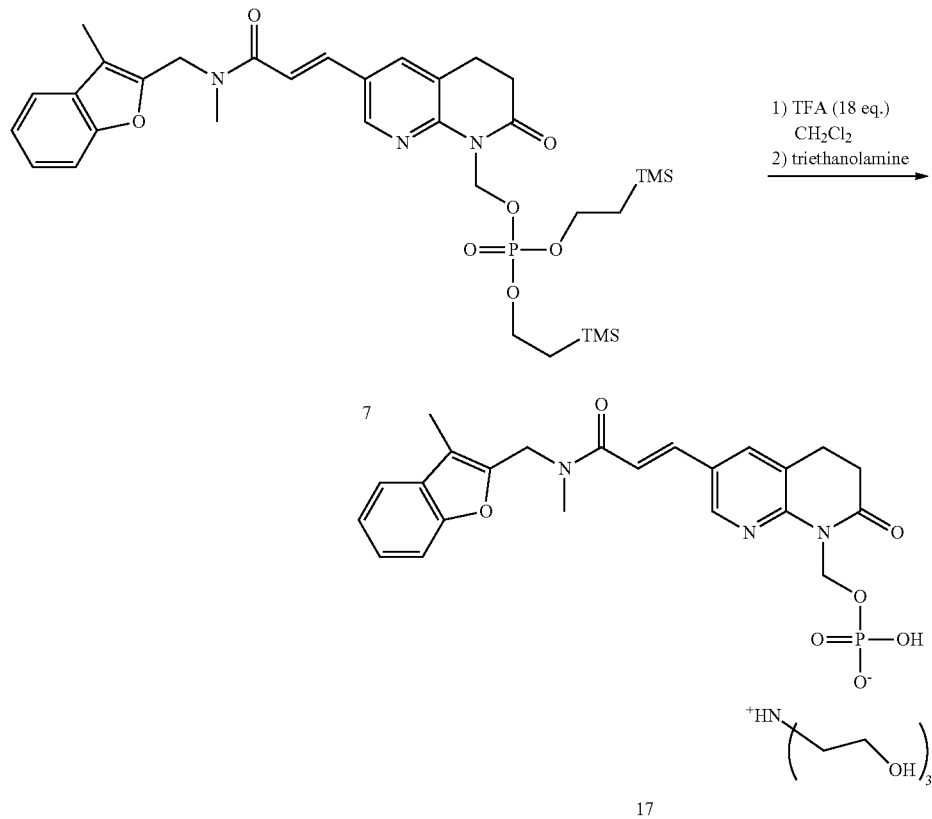

Compound 7 (1.95 g, 2.84 mmol) was dissolved in dichloromethane (12 mL) and cooled to −10° C. (bath temperature). Trifluoroacetic acid (3.8 mL, 51 mmol) in dichloromethane (3 mL) was slowly added to the cooled solution. The mixture was stirred at −10° C. for 15 minutes then cooled to <−30° C. (bath temperature) and triethanolamine (7.9 mL, 60 mmol) in dichloromethane (3 mL) was slowly added. The cold bath was then removed and the mixture left to warm to room temperature. The mixture was suspended in 10% isopropyl alcohol/diethyl ether (20 mL), stirred overnight and filtered, to yield a solid which consisted of product and undesired salts. The filtrates were evaporated to dryness and the residue was triturated with 10% isopropyl alcohol/diethyl ether. After the 2 washes in 10% isopropanol/diethylether, the desired compound crystallized and was washed with isopropyl alcohol (2×20 mL), filtered and air dried. The desired compound 17 was pure by $^1$H NMR. ((E)-6-[(N-methyl((3-methylbenzofuran-2-yl)methyl)amino)-3-oxoprop-1-en-1-yl]-2-oxo-3,4-dihydro-1,8-naphthyridin-1(2H)-yl]methylphosphate monobasic triethanolammonium salt).

Compound 17: $^1$H NMR (400 MHz D$_2$O): δ 8.05 (m, 1H), 7.58-6.70 (m, 7H), 5.60 (br s, 2H), 4.58-4.54 (2s from rotamers, 2H), 3.78 (br s, 6H), 3.30 (br s, 6H), 3.08, 1.97 (m, 10H).

Synthesis of Compound 18

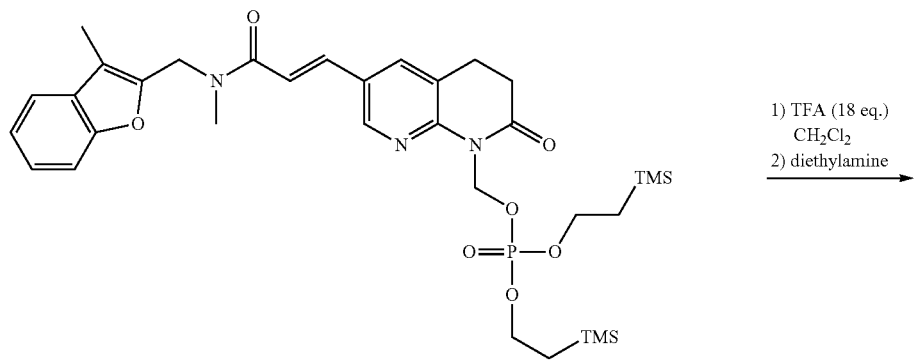

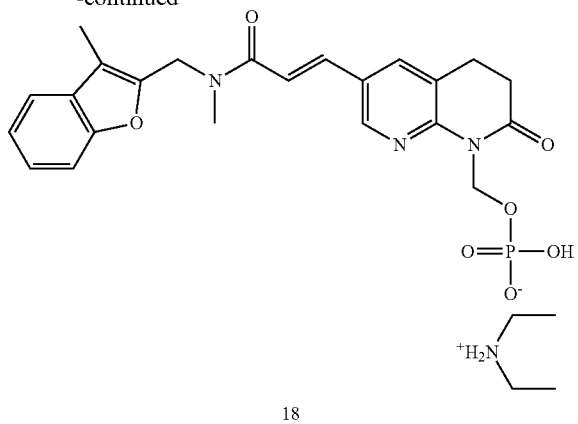

18

Compound 7 (2.2 g, 3.2 mmol) was dissolved in dichloromethane (13 mL) and cooled to −10° C. (bath temperature), to this was slowly added trifluoroacetic acid (4.3 mL, 58 mmol) in dichloromethane (3 mL). The mixture was stirred at −10° C. for 15 minutes, then cooled to <−30° C. (bath temperature) and diethylamine (6.95 mL) in dichloromethane (3 mL) was slowly added. The cold bath was then removed and the mixture left to warm to room temperature. The mixture was concentrated on the evaporator. The residue crystallized on stirring in ethyl acetate. The solid was filtered then washed 3 times in isopropyl alcohol (iPrOH), filtered, and air dried to afford 1.1 g of the desired Compound 18 ((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methylphosphate monobasic diethylammonium salt).

Compound 18: $^1$H NMR (400 MHz, DMSO d$_6$): δ 8.45 (d, 1H), 8.13 (d, 1H), 7.55-7.12 (m, 6H), 6.70 (s, 2H), 4.97, 4.77 (2s, 2H), 3.85 (q, 4H), 3.18-2.25 (m, 10H), 1.15 (t, 6H).

An alternate synthetic route to key intermediate compound 7 is described below in Scheme 3. Key intermediate, compound 7 is then converted to target compound 10 as described in Scheme 2.

Scheme 3

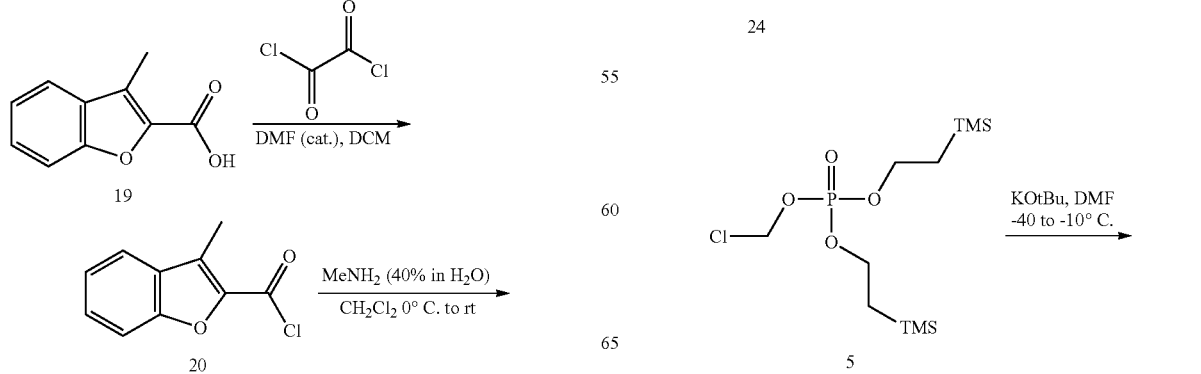

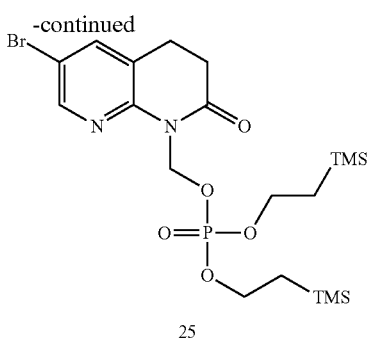

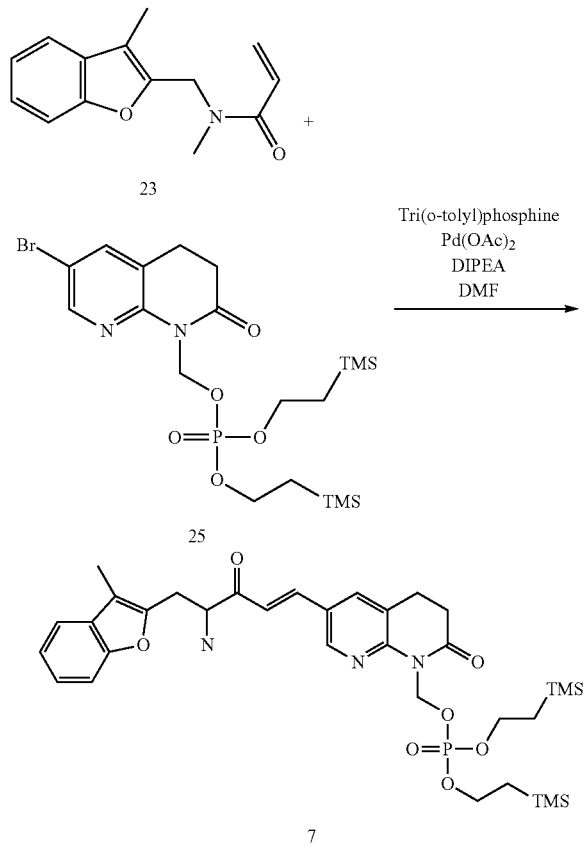

Synthesis of Compound 20

Oxalyl chloride (193 μL, 2.21 mmol, 2.0 eq.) was added dropwise, at room temperature to a solution of commercially available compound 19 (300 mg, 1.07 mmol) and DMF (one drop) in dichloromethane (17 mL). The reaction mixture was stirred at room temperature for 4 hours. Water (30 mL) was added to the reaction and the two phases were separated. The aqueous layer was extracted twice with dichloromethane. The combined organic layers were washed with saturated brine solution, dried over anhydrous sodium sulfate, filtered and concentrated in vacuo to yield 300 mg (90% yield) of the desired acid chloride 20. This material was used without further purification.

Synthesis of Compound 21

Methylamine (40% in water, 189 μL, 5.39 mmol, 3.5 eq.) was added dropwise at 0° C. to a solution of compound 20 (300 mg, 1.54 mmol) in dichloromethane (15 mL). The reaction mixture was warmed to room temperature and stirred for 2 hours. Water (50 mL) was added to the reaction and the two phases were separated. The aqueous layer was extracted twice with dichloromethane. The combined organic layers were washed with saturated brine solution, dried over anhydrous sodium sulfate, filtered and the filtrate concentrated in vacuo to yield 291 mg (100% yield) of the desired amide 21. This material was used without further purification.

Synthesis of Compound 22

To a stirred solution of compound 21 (286 mg, 1.51 mmol) in THF (12 mL) was added LiAlH$_4$ (75 mg, 1.96 mmol, 1.3 eq.) portionwise at room temperature. The reaction mixture was stirred and heated to reflux for 5 hours and then cooled to 0° C. Water (68 μL) was added and the mixture was stirred for 10 minutes. Sodium hydroxide 15% aqueous solution (75 μL) was added and the mixture was stirred for a further 15 minutes. Finally water (227 μL) was added and the solution was filtered through a pad of Celite and rinsed with EtOAc. The two layers were separated and the aqueous layer was extracted twice with EtOAc. The organic layers were combined and washed with saturated brine solution, dried over anhydrous sodium sulfate, filtered and the concentrated in vacuo to yield 235 mg (89% yield) of the desired amine product 22. This material was used without further purification.

Synthesis of Compound 23

To a stirred solution of compound 22 (117 mg, 0.671 mmol) in dichloromethane (6.7 mL) at room temperature was added dropwise triethylamine (140 μL, 1.00 mmol, 1.49 eq.) followed by acryloyl chloride (109 μL, 1.34 mmol, 2.0 eq.). The reaction mixture was stirred at room temperature for 4 hours and the solvent and reactants were removed in vacuo. The crude product was purified by flash chromatography (gradient, 0% to 40% EtOAc in hexanes) to yield 77 mg (50% yield) of the desired acrylamide 23.

Compound 23: $^1$H NMR (200 MHz, CDCl$_3$): δ 7.50 (m, 2H), 7.25 (m, 2H), 6.80-6.60 (m, 1H), 6.35-6.40 (m, 1H), 5.75 (t, 1H), 4.80-4.50 (2s from rotamers, 2H), 3.20-3.00 (2s from rotamers, 3H), 2.30 (s, 3H).

Synthesis of Compound 25

Commercially available compound 24 (300 mg, 1.32 mmol) was placed in DMF (13 mL), cooled to −40° C. and KOtBu (162 mg, 1.45 mmol, 1.1 eq.) was added in portions. The solution was stirred for 90 minutes upon which compound 5 (1150 mg, 3.33 mmol dissolved in 3 mL of DMF, 2.3 eq.), was added over 15 minutes. The yellow orange solution was stirred for an additional two hours as it warmed to −28° C. The dark orange solution was stirred for 1.5 hours as it warmed to −10° C. and then a further 1.5 hours as it warmed to −5° C. The reaction was quenched with dilute ammonium chloride (60 mL) followed by water (20 mL). The organic and aqueous layers were separated. The aqueous layer was extracted twice with ethyl acetate (80 mL). The combined organic layers were back extracted with water (100 mL) to removed DMF, and were dried over anhydrous sodium sulfate. The dried organic layers were filtered and concentrated in vacuo to give a solid residue. The crude solid was purified by flash chromatography (24 g of silica gel using 50-100% EtOAc/hex) to yield 150 mg (22% yield) of pure compound 25 as a viscous bright yellow oil.

Compound 25: $^1$H NMR (400 MHz, CDCl$_3$): δ 8.25 (s, 1H), 7.60 (s, 1H), 6.00 (d, 2H), 4.10 (m, 4H), 2.92 (t, 2H), 2.70 (t, 2H), 1.05 (m, 4H), 0.00 (s, 18H).

Synthesis of Compound 7

Compound 23 (77 mg, 0.336 mmol) and compound 25 (150 mg, 0.279 mmol) were dissolved in dry DMF (2.8 mL) under a nitrogen atmosphere. To this solution was added in this order: palladium (II) acetate (1.56 mg, 0.007 mmol), tri(o-tolyl)phosphine (4.24 mg, 0.014 mmol) and N,N-diisopropylethylamine (74 µL, 0.418 mmol) under a nitrogen atmosphere. The reaction mixture was stirred at 80° C. for 4 hours then cooled to room temperature. Ethyl acetate (20 mL) and a saturated aqueous solution of ammonium chloride (20 mL) were added and the two phases were separated. The aqueous layer was extracted two more times with ethyl acetate. The organic layers were combined and washed with saturated brine solution, dried over anhydrous sodium sulfate, filtered and the solid concentrated in vacuo. The crude product was purified by flash chromatography (gradient, 50% to 100% EtOAc in hexanes) to yield 26.5 mg (14% yield) of the desired compound 7; identical to key intermediate 7 by $^1$H-NMR, MS and HPLC.

Example 2: Solubility Testing

Compounds disclosed herein were tested for aqueous solubility at 25° C. The results are summarized below in Table A. The bis-sodium and bis-ammonium compounds formed unwieldy gels during the solubility experiments. Thus their solubilities were not measured. It is also noteworthy that the bis-sodium salt, originally amorphous, crystallized within 7 days in aqueous buffer, resulting in a solubility of <5 mg/mL (pH 6.6-7.1).

TABLE A

Solubility of Certain Salts in Water at 25° C. (mg free acid equivalent/mL).

| Salt | Water (mg/mL) | Comments |
|---|---|---|
| Bis-Sodium (amorphous) (Compound B) Compound 9 | — | Forms gels |
| Bis-Ammonium (amorphous) (Compound C) Compound 14 | — | Forms gels |
| Bis-Potassium (amorphous) (Compound 11) | >100 | |
| Bis-Potassium (crystalline) (Compound 11) | 30-35 | |
| Calcium (Compound 13) | <0.1 | |
| Magnesium (Compound 12) | <1 | |
| Monobasic Monomethylammonium (15) | <20 | Forms gels |
| Monobasic Dimethylammonium (16) | 20-30 | Forms gels |
| Monobasic Diethylammonium (18) | 50-60 | Forms gels |
| Monobasic Triethanolammonium (17) | 5-15 | Forms gels |
| Bis-Ethanolammonium (crystalline) (Compound A) Compound 10 | >300 | |
| Compound IV | <0.001 | |

Example 3: Solid State Stability Testing

Various compounds disclosed herein have been placed on long-term solid-state stability protocol. The compounds were stored in glass vials closed with PTFE lined caps at 30° C./65% RH, 40° C./75% RH, 50° C. and 60° C. (ambient humidity). The results of the study after 4 weeks are shown in Table B1 and after 3 months in Table B2. Appearance and purity analysis were conducted using HPLC and XPRD. The HPLC analyses were conducted using standard equipment such as a Agilent HP1100 HPLC (Station ID: LZPES HPLC 04) with YMC-Pack ODS-AQ sub 3 µm, 150×4.6 mm The bis-ethanolammonium compound (compound A, 10) possessed markedly improved solid-state stability over the bis-sodium and bis-potassium compounds (see Table B1).

TABLE B1

Solid-state Stability of Salts (4-Weeks)

| Salt | Control* % Area[#] | 30° C./ 65% RH % Area | 40° C./ 75% RH % Area | 50° C./ AMB[+] % Area | 60° C./ AMB % Area |
|---|---|---|---|---|---|
| Bis-Sodium (amorphous) (Compound B) compound 9 | 96.4 | 96.3 | 84.4 | 86.8 | 85.9 |
| Bis-Potassium (crystalline) (11) | 95.4 | 87.8 | 64.3 | 72.5 | 50.7 |
| Bis-Ethanolammonium (crystalline) (Compound A) compound 10 | 98.9 | 98.5 | 98.2 | 99.3 | 98.7 |

*Control sample stored at ambient lab conditions protected from light.
[#]% Area = Relative % area of Compound IV (conjugate base) to the total assay peak area by HPLC analysis.
[+]AMB = ambient humidity.

TABLE B2

Solid-state Stability of Salts (After 3 Months)

| Salt | Control* % Area[#] | 30° C./ 65% RH % Area | 40° C./ 75% RH % Area | 50° C./ AMB[+] % Area |
|---|---|---|---|---|
| Compound 10 | 98.9 | 98.61 | 92.75 | 99.04 |

*Control sample stored at ambient lab conditions protected from light.
[#]% Area = Relative % area of Compound IV (conjugate base) to the total assay peak area by HPLC analysis.
[+]AMB = ambient humidity.

The bis-ethanolammonium compound, Compound A (10) also showed dramatically improved photostability compared to the bis-sodium compound 9 (Table C).

TABLE C

| Salt | Control* % Area[#] | Photo-stability % Area |
|---|---|---|
| Bis-Sodium (amorphous) (Compound B) compound 9 | 96.4 | 55.9 |
| Bis-Ethanolammonium (crystalline) (Compound A) compound 10 | 98.9 | 97.7 |

[+]Exposed to 60% of ICH minimum.
*Control sample stored at ambient lab conditions protected from light.
[#]% Area = Relative % area of Compound IV(conjugate base) to the total assay peak area by HPLC analysis.

Additionally, the crystalline bis-ethanolammonium compound 10, (Compound A) was proven to be stable to gamma irradiation in a range of 25 to 31 kGy.

Samples were prepared for XRPD by sprinkling ~20 mg onto a Si wafer zero background plate and pressing the material flat to ensure the surface is smooth and level. The samples were analyzed according the equipment parameters below.

| Bruker D8-Advance XRPD S/N: 202298 | |
|---|---|
| Configuration | Theta/theta Bragg Brentano |
| Incident Beam Optics | Soller slit = 2° |
| | Divergence slit = 0.2 mm |
| | Antiscatter screen = 21 mm |
| Detector Beam Optics | Soller slit = 2.5° |
| | Ni filter |
| | Antiscatter slit = 3 mm |
| Detector | PSD: Lynx Eye with 1° window |
| Tube | CuKα λ = 1.5418 Å |
| | Voltage = 40 kV, Current = 40 mA |
| Scan Parameters | 2-50° 2θ |
| | Step size 0.049° 2θ |
| | Time per step 1 s |
| | Total Scan Time = 16.5 minutes |

The XRPD results are shown in FIGS. 3A-B, 4A-B, 5 and 6. There was no change in crystal form of compound 10 after 3 months at all conditions. Compound 9 is amorphous and exhibits no change over 4 weeks at all storage conditions. The XRPD for compound 11 shows some changes at 4 weeks, particularly for the 40° C./70% RH condition, where sharper peaks appear particularly above 20° 2θ, and underwent significant degradation at 4 weeks at 40/75 (content ~65%), with many peaks present in its chromatogram.

These studies confirm that: compound 10 is a crystalline salt that is physically and chemically stable over 3 months at 30° C./65% RH and 50° C. when stored in closed vials and light protected. There was no change in appearance and crystal form over 3 months at all storage conditions, and is also stable to gamma irradiation exposure of 28.6-30.9 kGy; compound 9 is an amorphous salt that is chemically stable over 1 month at 30° C./65% RH when stored in closed vials and light protected, with no change in appearance and it remained amorphous over 1 month at all storage conditions; compound 11 is a partially crystalline salt that is not chemically stable over 1 month at 30° C./65% RH, at 40° C./75% RH and at 50° C. when stored in closed vials and light protected. There was no change in appearance and it remained partially crystalline over 1 month at all storage conditions.

Example 4: Solution Stability Testing

The bis-ethanolammonium compound 10 was solubilized at 25 and 1 mg/mL in water for injection (WFI) and 5% dextrose in water (DW5) and tested for stability in solution at various temperatures. Solution stability data in WFI is shown in Table D. Solution stability data in D5W is shown in Table E.

TABLE D

Solution stability of Compound A (10) in water for injection (WFI) at 25° C.

| | Initial | | 4 hours | | 24 hours | | 48 hours | |
|---|---|---|---|---|---|---|---|---|
| Condition | mg/mL | % Area[#] | mg/mL | % Area | mg/mL | % Area | mg/mL | % Area |
| RT | 24.05 | 99.5 | 23.9 | 98.8 | 22.5 | 95.2 | 22.8 | 91.5 |
| 5° C. | | | 25.0 | 99.3 | 24.4 | 98.6 | 23.1 | 98.0 |
| −20° C. | | | — | — | — | — | 24.4 | 99.2 |
| RT | 0.97 | 99.4 | 0.94 | 99.0 | 0.92 | 95.5 | 0.64 | 92.1 |
| 5° C. | | | 0.96 | 99.4 | 0.94 | 98.1 | 0.96 | 98.1 |
| −20° C. | | | — | — | — | — | 0.96 | 99.3 |

[#]% Area = Relative % area of Compound IV (conjugate base) to the total assay peak area by HPLC analysis

TABLE E

Solution stability of Compound A (10) in 5% dextrose in water (D5W) at 25° C.

| | Initial | | 4 hours | | 24 hours | | 48 hours | |
|---|---|---|---|---|---|---|---|---|
| Condition | mg/mL | % Area[#] | mg/mL | % Area | mg/mL | % Area | mg/mL | % Area |
| RT | 24.4 | 99.6 | 24 | 98.9 | 23.8 | 95.6 | 23 | 92.1 |
| 5° C. | | | 24.9 | 99.3 | 24.5 | 98.7 | 24.5 | 98.1 |
| −20° C. | | | | | | | 24.6 | 99.3 |
| RT | 1.00 | 99.5 | 0.99 | 99 | 0.96 | 96.1 | 0.95 | 93.1 |
| 5° C. | | | 0.99 | 99.4 | 0.99 | 98.8 | 1.00 | 98.1 |
| −20° C. | | | | | | | 0.99 | 99.3 |

[#]% Area = Relative % area of Compound IV(conjugate base) to the total assay peak area by HPLC analysis.

Example 5: Comparative Pharmacokinetics

Compounds were tested in both rats and dogs for pharmacokinetic parameters and oral bioavailability against the free base (compound IV), tosylate anhydrate salt (Compound Y) and tosylate monohydrate salt (compound Z) of (E)-N-methyl-N-((3-methylbenzofuran-2-yl)methyl)-3-(7-oxo-5,6,7,8-tetrahydro-1,8-naphthyridin-3-yl)acrylamide designated as compounds IV, Y, and Z respectively, using the conditions described below. The structures of the compounds are shown in Table F.

TABLE F
| Compound | Structure |
|---|---|
| Bis-ammonium (C) Amorphous Compound 14 | 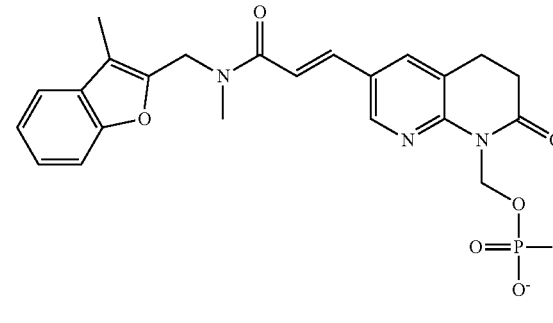 2NH$_4^+$ |
| Bis-sodium (B) Compound 9 | 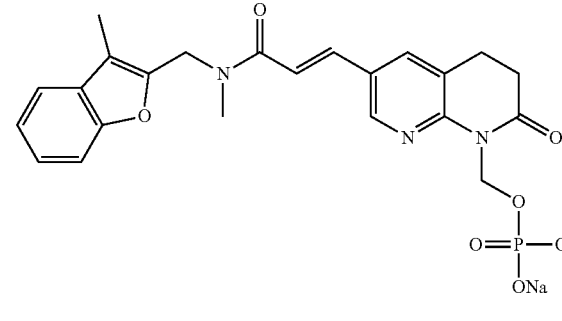 |
| Bis-ethanolammonium (A) Compound 10 | 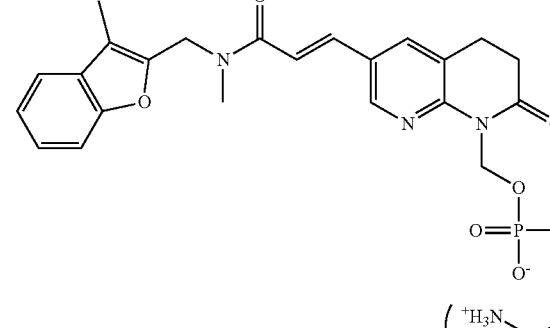 |
| Compound IV (free base) | 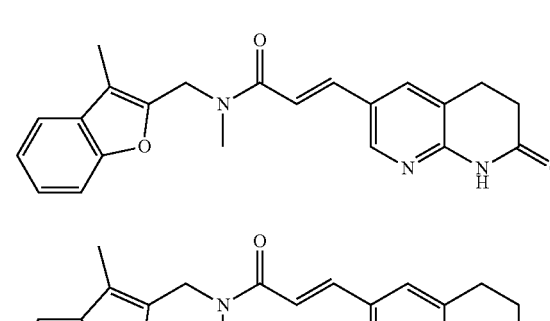 |
| Compound Y (tosylate anhydrate) | 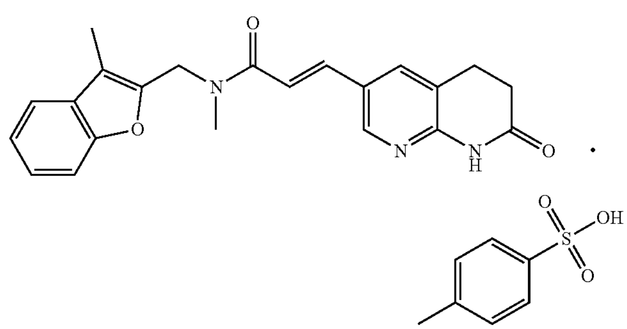 |

TABLE F-continued

| Compound | Structure |
|---|---|
| Compound Z (tosylate monohydrate) | 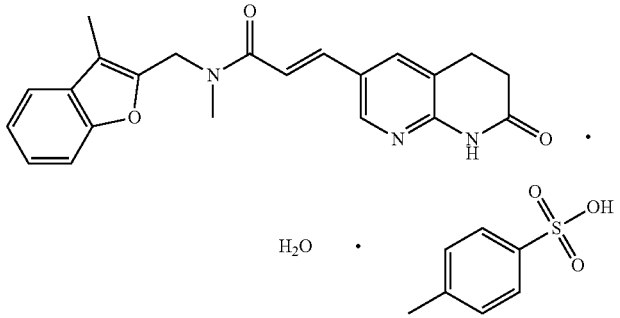 |

Compound IV, Y or Z were administered orally as a suspension using 80% PEG400, 0.5% carboxymethylcellulose or OraPlus as vehicles. When compound IV, Y or Z were administered intravenously, a solution of 40% 2-HP-ß-cyclodextrin in PBS was used as the vehicle, in order to achieve a composition for intravenous administration. For human use however it is noted that such a cyclodextrin formulation would be toxic and unacceptable for treatment.

Bis-ammonium, bis-sodium and bis-ethanolammonium compounds (Compounds 14, 9 and 10) were administered both orally and intravenously as a solution in 5% dextrose in water, normal saline or phosphate buffered saline. For all compounds tested, oral administration was by gavage and intravenous administration by bolus injection or infusion.

Figure 2:
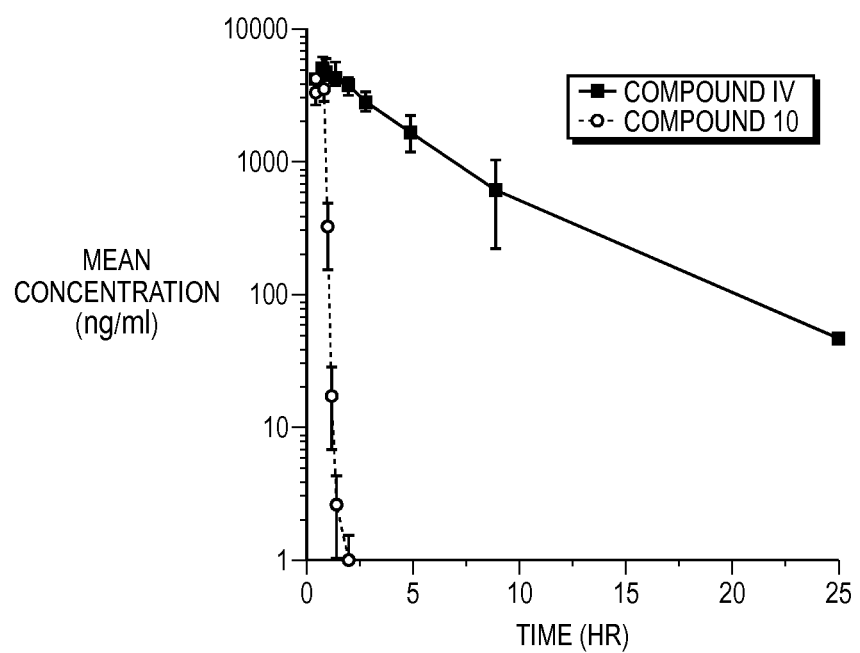
FIG. 2 depicts comparative pharmacokinetics of Compound IV and Compound 10 in male dogs after administration via intravenous infusion of Compound 10.

All dose levels and plasma concentrations are calculated as Compound IV equivalents. There is no gender effect in dogs and female rats. The rapid appearance of compound IV (free base) indicates efficient conversion of Compounds 14, 9 and 10 to Compound IV in plasma. This was confirmed by simultaneous analysis of compound IV and Compound 10 in dog plasma after intravenous dosing with compound 10 as shown in FIG. 2. Similar results were obtained after intravenous dosing Compound 10 in rats.

Table G below summarizes mean pharmacokinetic parameters of compound IV after administration of bis-ammonium (amorphous compound 14), bis-sodium (compound 9) and bis-ethanolammonium (compound 10) in female rats (5 mg/kg, Compound IV equivalents). The data indicate that all compounds are rapidly converted to Compound IV and show comparable pharmacokinetics and oral bioavailability within biological and experimental variation rates.

TABLE G

Pharmacokinetic parameters of compound IV after oral and intravenous administration of compounds 9, 10, and 14 in female rats

Figure 1B:
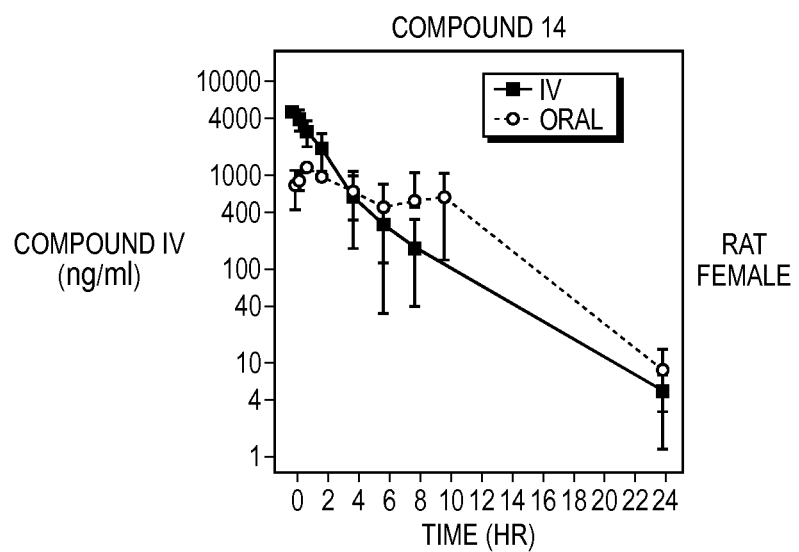
Figure 1C:
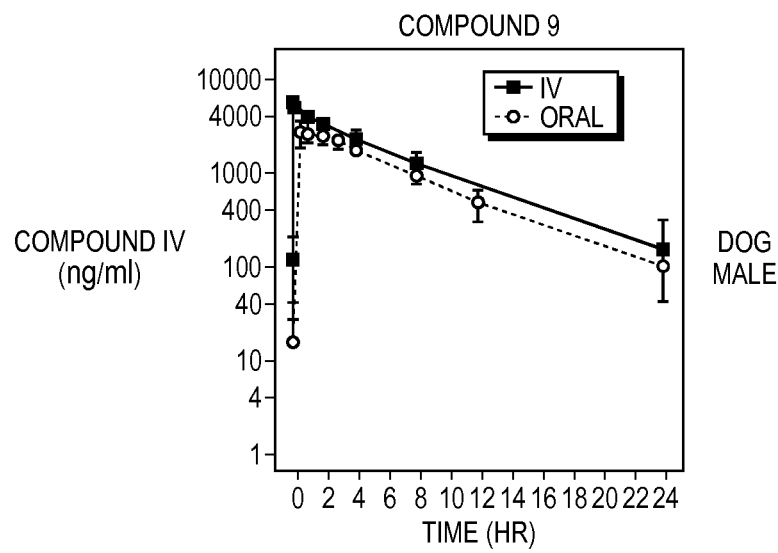
Figure 1D:
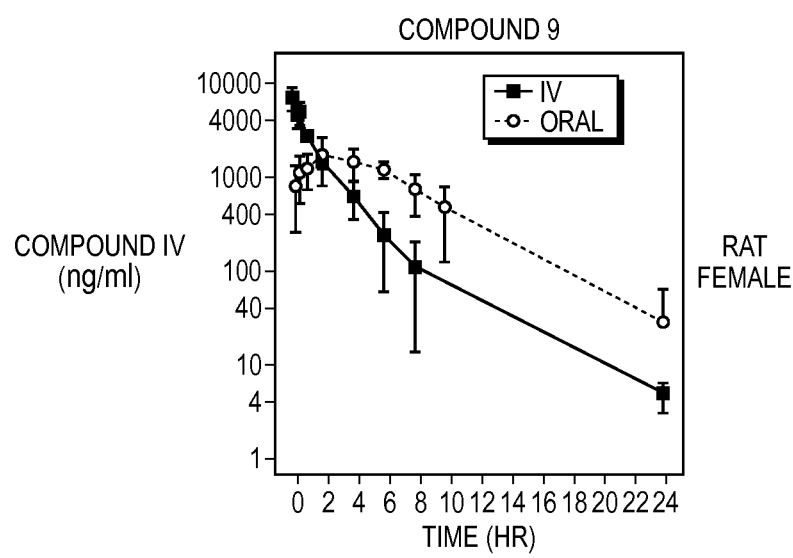
Figure 1E:
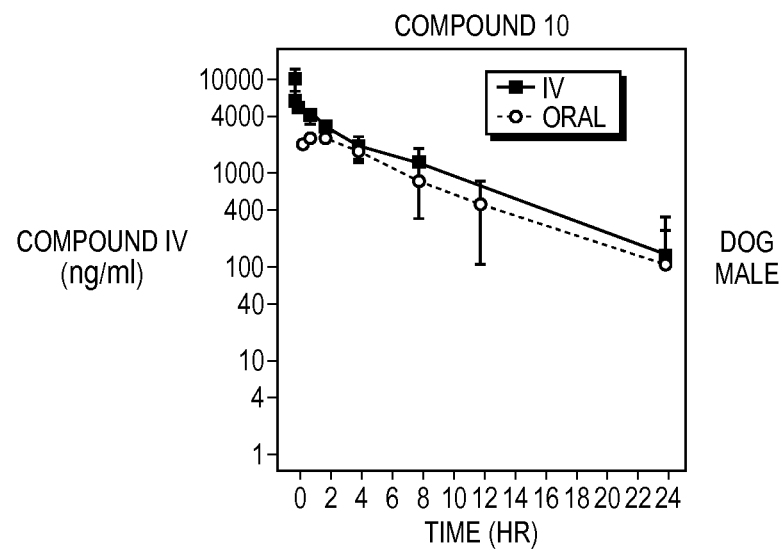
Figure 1F:
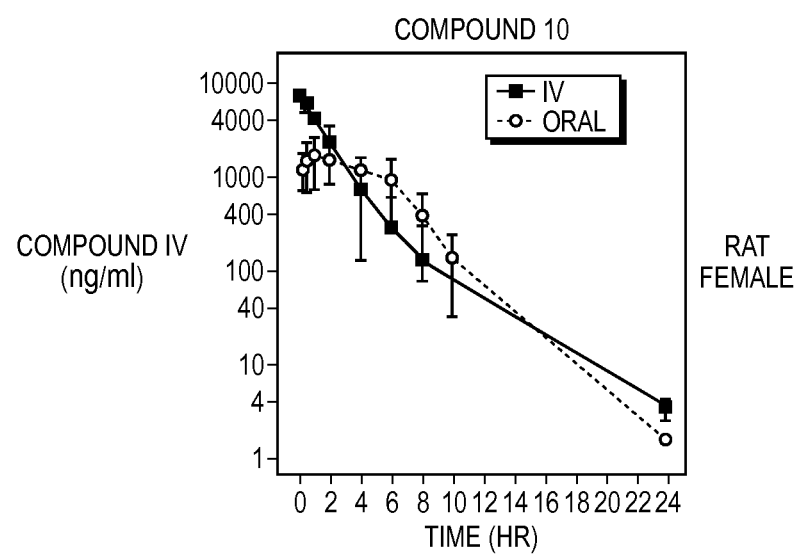

| Route | Compound | Tmax (hr) | Cmax (ng/ml) | Half life (hr) | $AUC_{0-24}$ (hr * ng/ml) | Oral bio-availability |
|---|---|---|---|---|---|---|
| Intravenous | Compound 14 | 0.08 | 5,137 | 3.31 | 12,579 | |
| | Compound 9 | 0.08 | 7,583 | 3.79 | 11,961 | |
| | Compound 10 | 0.14 | 8,070 | 3.65 | 16,092 | |
| Oral | Compound 14 | 1.00 | 1,333 | 2.78 | 12,065 | 96% |
| | Compound 9 | 3.33 | 1,907 | 3.14 | 16,179 | 135% |
| | Compound 10 | 3.00 | 2,040 | 2.20 | 11,376 | 71% | dogs on the PK of these compounds. However, male rats were not a good model for this study because of high clearance rates and low exposures when compared to female rats. Therefore, male rats were typically not tested in these PK models or excluded from the analyses. FIG. 1A-B show mean time-concentration plots for compound IV after administration of bis-ammonium, bis-sodium and bis-ethanolammonium compounds (Compounds 14, 9 and 10) at a dose level of 5 mg/kg (compound IV equivalents) in male Table H below summarizes mean pharmacokinetic parameters of compound IV after administration of bis-ammonium (amorphous compound 14), bis-sodium (compound 9) and bis-ethanolammonium (compound 10) in male dogs (5 mg/kg, Compound IV equivalents). The data indicate that all compounds are rapidly converted to compound IV and show comparable pharmacokinetics and oral bioavailability within biological and experimental variation rates.

TABLE H

Pharmacokinetic parameters of compound IV after intravenous and oral administration of compound 9, 10, and 14 to male dogs

| Route | Compound | Tmax (hr) | Cmax (ng/ml) | Half life (hr) | $AUC_{0-24}$ (hr * ng/ml) | Oral bioavailability |
|---|---|---|---|---|---|---|
| Intravenous | Compound 14 | 0.58 | 4,049 | 3.9 | 26,659 | |
| | Compound 9 | 0.08 | 6,216 | 4.8 | 35,993 | |
| | Compound 10 | 0.09 | 8,331 | 4.6 | 36,083 | |
| Oral | Compound 14 | 1.25 | 2,632 | 3.8 | 20,821 | 78% |
| | Compound 9 | 0.9 | 3,123 | 4.6 | 23,585 | 66% |
| | Compound 10 | 1.33 | 2,684 | 4.6 | 19,765 | 54% |

Table I below summarizes mean pharmacokinetic parameters of compound IV in both dog and rat following intravenous administration of amorphous compound 14, compound 9 and compound 10 with comparative data for Compound Z at a dose level of 5 mg/kg (Compound IV (free base) equivalents). The data indicate that compounds 14, 9 and 10 possessed a longer half-life than Compound Z. Notably, compounds 9 and 10 had the longest half-lives, approximately 60% and 25% longer than Compound Z in rat and dog, respectively. In addition, compound 10 showed the highest exposures (approximately 16% and 11% higher in rat and dog, respectively than Compound Z).

Figure 3A:
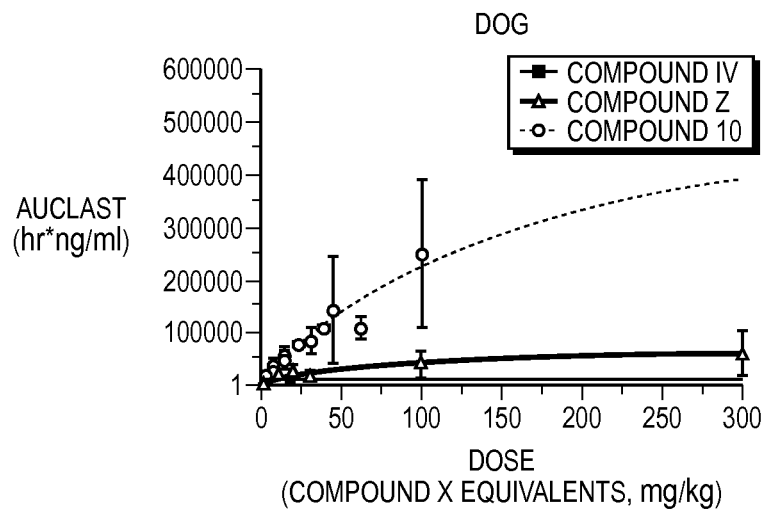
FIGS. 3A-B depict the correlation of exposure (AUC) with oral dose levels of disclosed compounds in A) dog and B) rat and specifically show the pharmacokinetics of Compound IV after oral administration of Compound IV, Compound Z or Compound 10 in dogs (3A) and rats (3B).
Figure 3B:
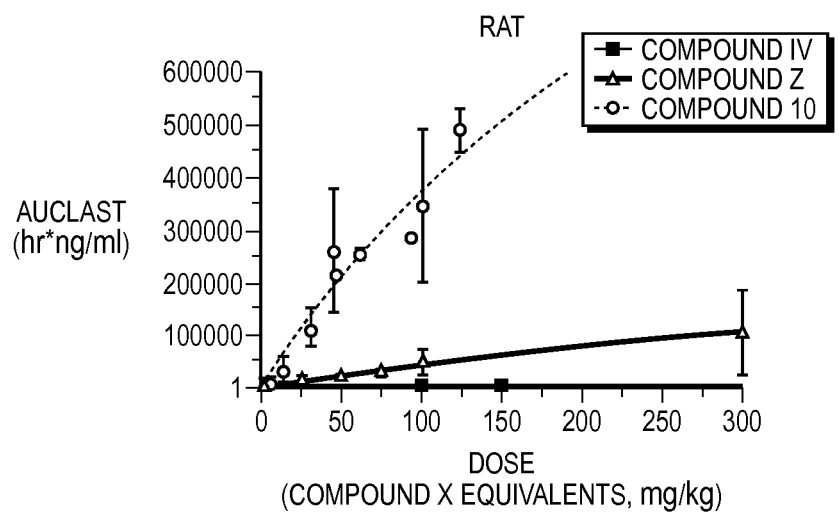
Figure 4A:
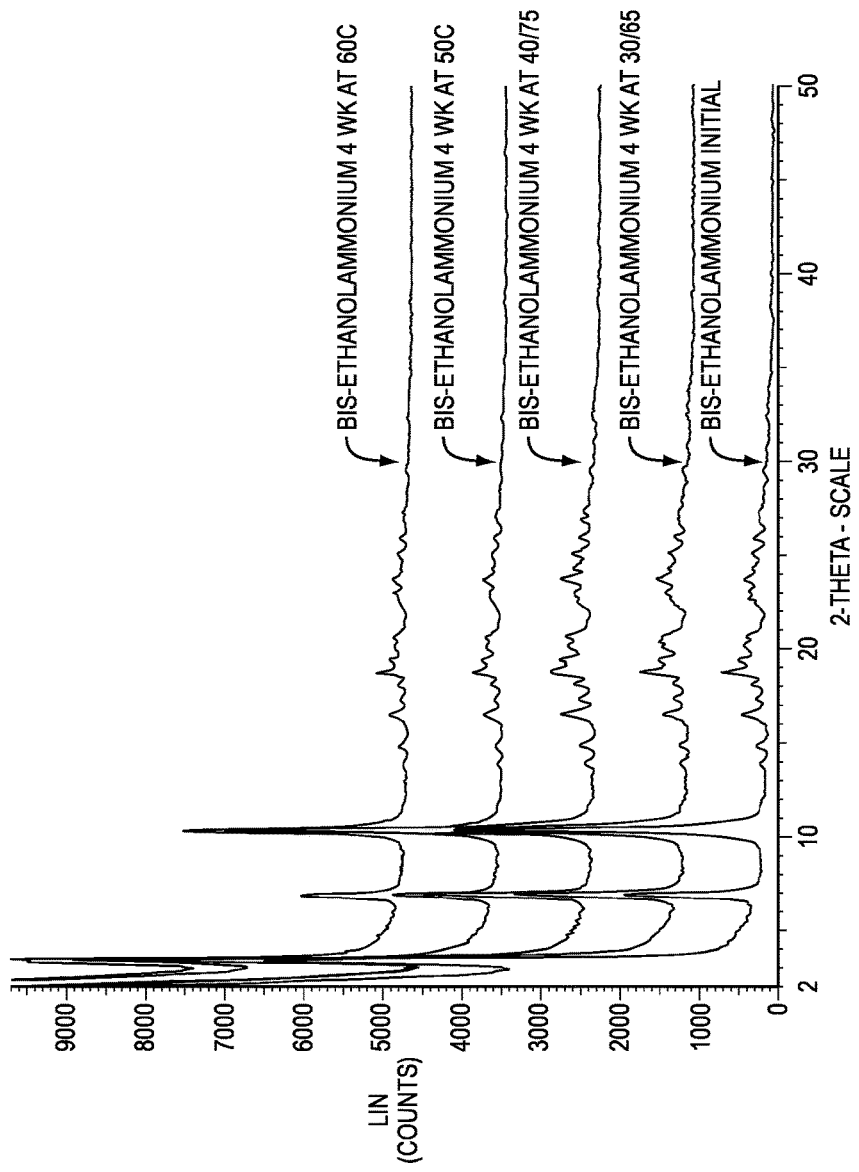
FIGS. 4A-B depict the XRPD spectra of Compound 10.
Figure 4B:
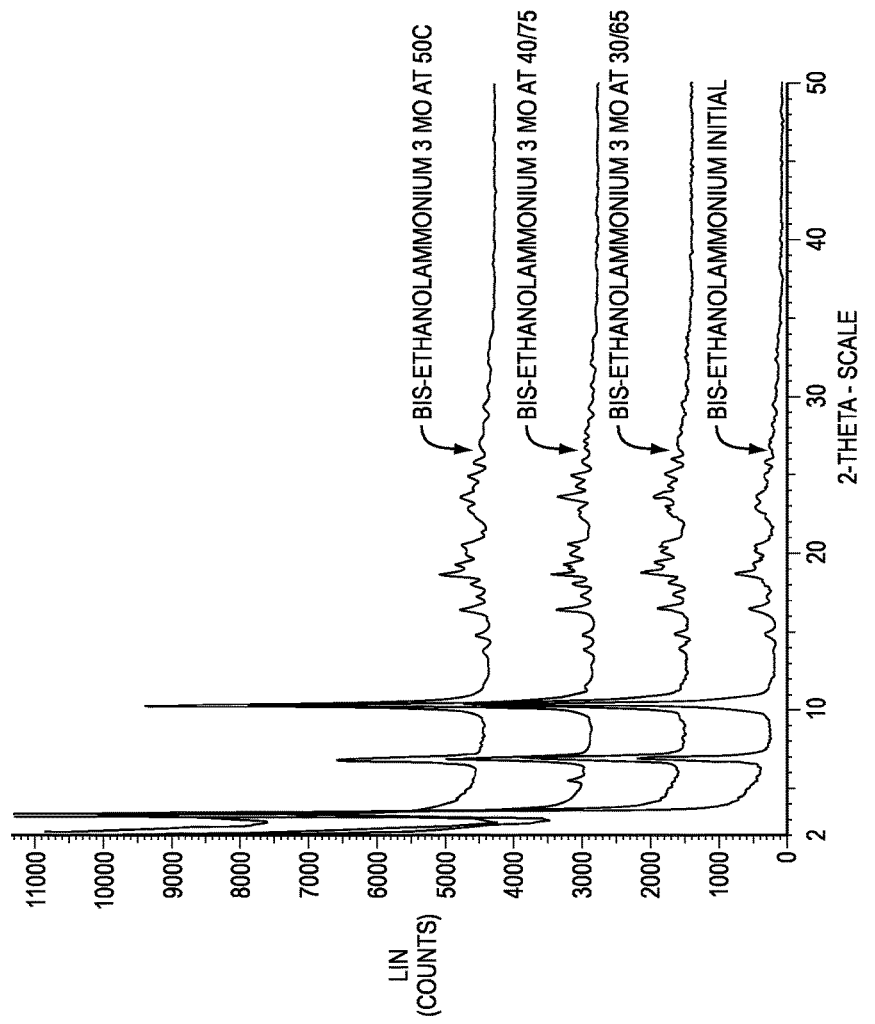
Figure 5:
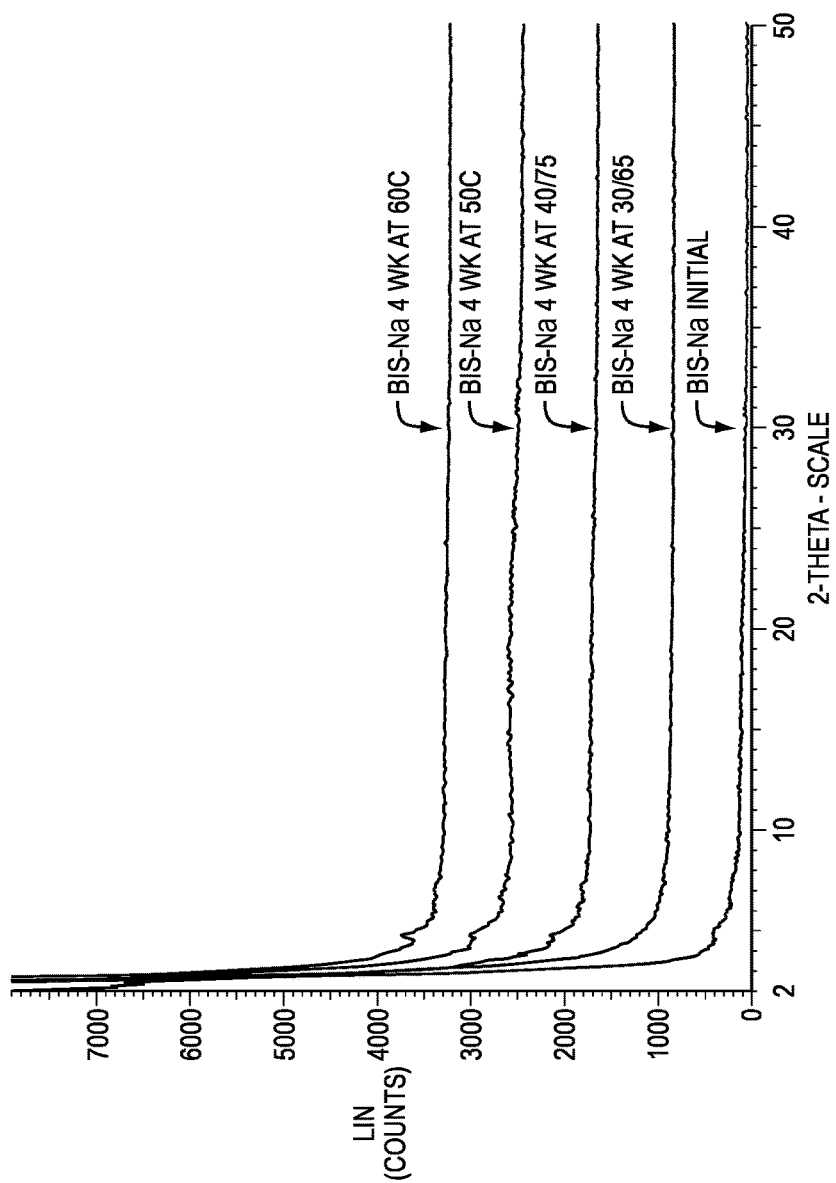
FIG. 5 depicts the XRPD spectra of Compound 9.
Figure 6:
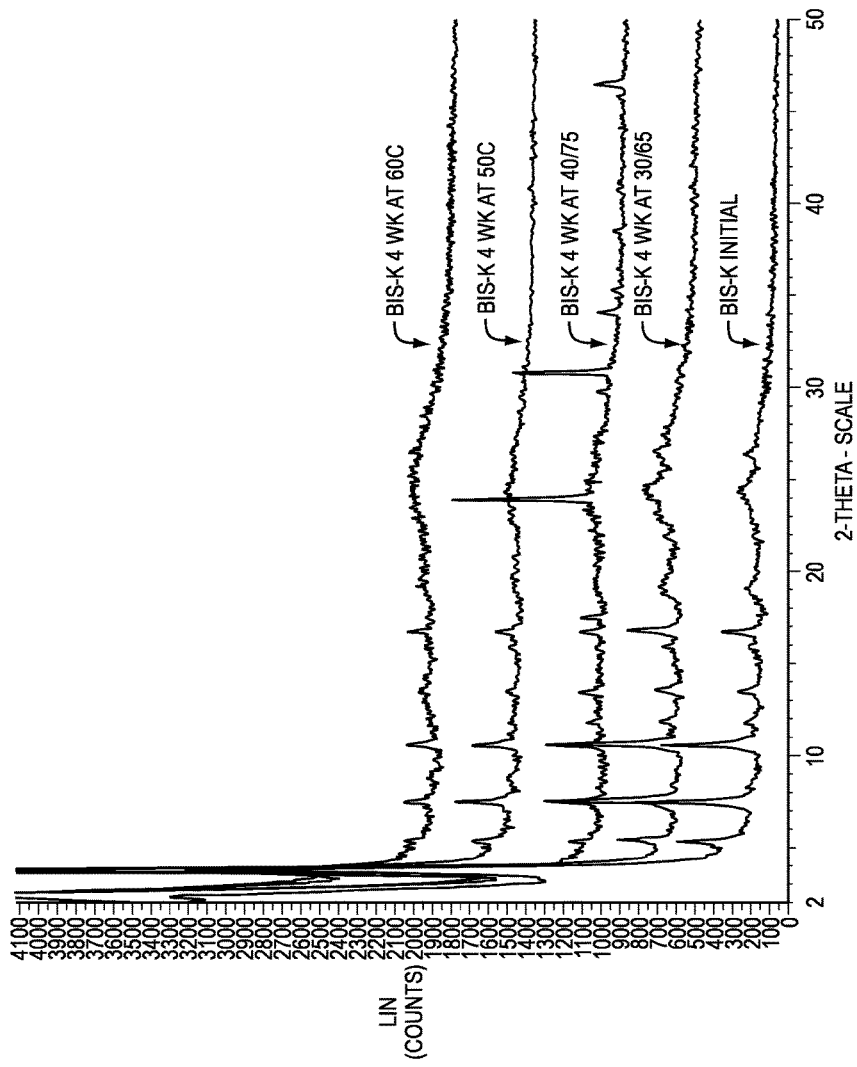
FIG. 6 depicts the XRPD spectra of Compound 11.
Figure 7:
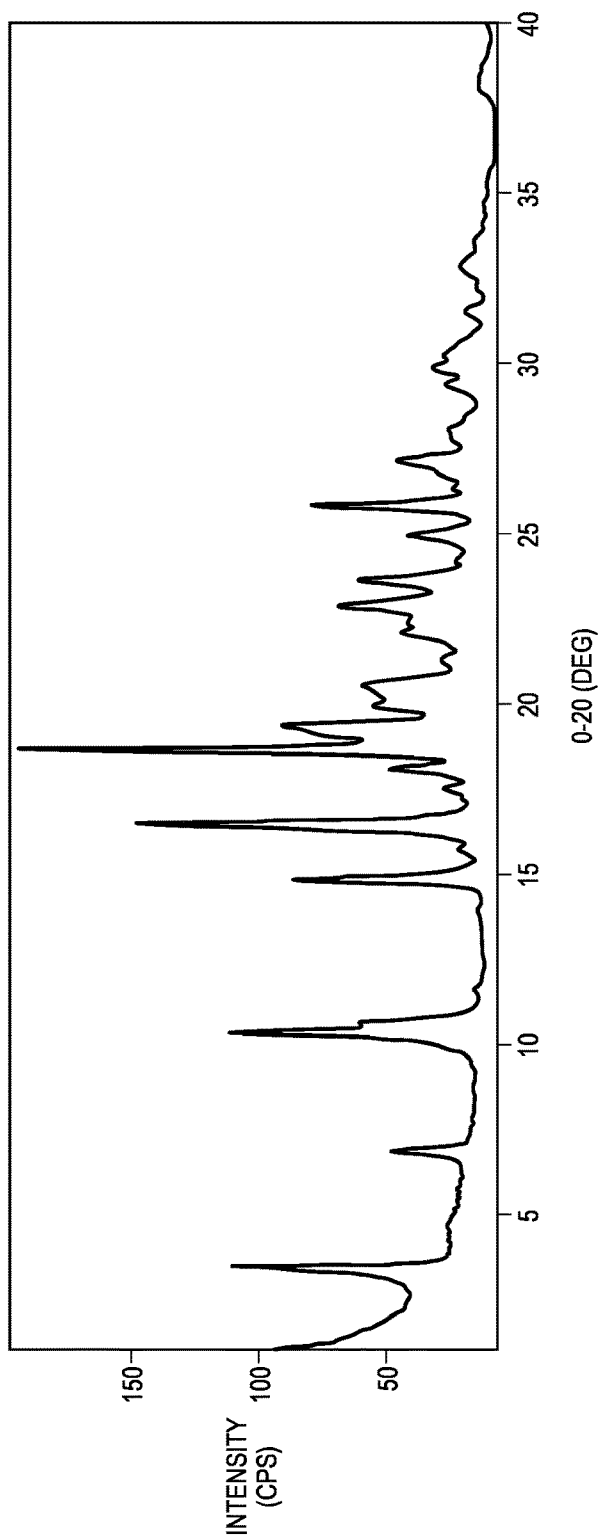
FIG. 7 depicts the XRPD spectra of Compound 10.

FIGS. 3A and 3B show the results of a comparison of the oral bioavailability of the active compound IV in dog and rat after administration of the bis-ethanolammonium compound 10, Compound IV, and Compound Z. As indicated in the Figures, the bis-ethanolammonium compound showed significantly higher oral bioavailability than both compound IV and Compound Z.

Tables K and L show comparative Compound IV oral bioavailability data after administration of compound 10 or Compound Z. Notably, compound 10 possessed improved bioavailability (of compound IV) in both dog and rat models when compared to Compound Z. Specifically, the bis-ethanolammonium compound 10 provided a 3- to 7 fold higher bioavailability of Compound IV in the dog and 7- to 9-fold higher bioavailability of Compound IV in the rat than Compound Z. Remarkably, as shown in Tables M and N, the bioavailability of Compound IV after administration of

TABLE I

Pharmacokinetic parameters of compound IV after intravenous administration of compound 9, 10, and 14 in dog and rat

| Route | Dose level* | Species | Compound | Tmax (hr) | Cmax (ng/ml) | Half life (hr) | $AUC_{0-24}$ (hr * ng/ml) |
|---|---|---|---|---|---|---|---|
| Intravenous | 5 | Rat | Compound Z | 0.02 | 10364 | 2.3 | 13837 |
| | | | Compound 14 | 0.08 | 5137 | 3.3 | 12579 |
| | | | Compound 9 | 0.08 | 7583 | 3.8 | 11961 |
| | | | Compound 10 | 0.14 | 8070 | 3.6 | 16092 |
| | | Dog | Compound Z | 0.02 | 6911 | 3.6 | 43551 |
| | | | Compound 14 | 0.58 | 4049 | 3.9 | 26659 |
| | | | Compound 9 | 0.08 | 6216 | 4.8 | 35993 |
| | | | Compound 10 | 0.08 | 10973 | 4.6 | 48540 |

*(Compound IV molar equivalents, mg/kg)

Table J shows a comparison of the pharmacokinetics of Compound IV following intravenous administration of Compound Z and Compound 10 in dogs. Compound 10 showed significantly longer half-lives than Compound Z at doses of 5 and 25 mg/kg.

TABLE J

Pharmacokinetic parameters of compound IV after intravenous administration of compound 10 and Z

| Route | Dose level (Compound IV molar equivalents, mg/kg) | Species | Compound | Tmax (hr) | Cmax (ng/ml) | Half life (hr) | $AUC_{0-24}$ (hr * ng/ml) |
|---|---|---|---|---|---|---|---|
| intravenous | 1 | Dog | Compound Z | 0.017 | 2129 | 3.5 | 8972 |
| | | | Compound 10 | 1.08[a] | 1262 | 3.5 | 6261 |
| | 5 | | Compound Z | 0.017 | 6911 | 3.6 | 43551 |
| | | | Compound 10 | 0.083 | 10973 | 4.6 | 48540 |
| | 25 | | Compound Z | 0.017 | 31642 | 2.5 | 87438 |
| | | | Compound 10 | 2.92[b] | 9482 | 4.3 | 68402 |

[a] 1 hour infusion;
[b] 4 hour infusion compound 10 was up to 38-fold higher than after administration of Compound IV in the dog and up to 144 fold higher in the rat. Most significantly, the bioavailability of Compound IV after administration of Compound 10 was much less dose-dependent than after administration of compound IV and Z as indicated by the increasing relative bioavailabilities with increasing doses.

TABLE K

Dog Oral Bioavailability: Compound IV exposures after Compound 10 and Compound Z administration

| Dose level (compound IV molar equivalents, mg/kg) | $AUC_{0-24}$ (hr * ng/ml) | | Relative Oral Bioavailability Compound 10/ Compound Z |
|---|---|---|---|
| | Compound Z | Compound 10 | |
| 3 | 3,859 | 10,727 | 2.8 |
| 10 | 11,289 | 34,002 | 3.0 |
| 30 | 25,710 | 92,408 | 3.6 |
| 100 | 45,931 | 226,468 | 4.9 |
| 300 | 59,269 | 387,188 | 6.5 |

TABLE L

Rat Oral Bioavailability: Compound IV exposures after Compound 10 and Compound Z administration

| Dose level (compound IV molar equivalents, mg/kg) | $AUC_{0-24}$ (hr * ng/ml) | | Relative Oral Bioavailability Compound 10/ Compound Z |
|---|---|---|---|
| | Compound Z | Compound 10 | |
| 3 | 1,632 | 14,642 | 9.0 |
| 10 | 5,320 | 47,360 | 8.9 |
| 30 | 15,578 | 135,673 | 8.7 |
| 100 | 46,437 | 379,650 | 8.2 |
| 300 | 107,186 | 782,022 | 7.3 |

TABLE M

Dog Oral Bioavailability: Compound IV exposures after Compound 10 and Compound IV administration

| Dose level (compound IV molar equivalents, mg/kg) | $AUC_{0-24}$ (hr * ng/ml) | | Relative Oral Bioavailability Compound 10/ Compound IV |
|---|---|---|---|
| | Compound IV | Compound 10 | |
| 3 | 9,460 | 10,727 | 1.1 |
| 10 | 9,917 | 34,002 | 3.4 |
| 30 | 10,059 | 92,408 | 9.2 |
| 100 | 10,109 | 226,468 | 22 |
| 300 | 10,123 | 387,188 | 38 |

TABLE N

Rat Oral Bioavailability: Compound IV exposures after Compound 10 and Compound IV administration

| Dose level (compound IV molar equivalents, mg/kg) | $AUC_{0-24}$ (hr * ng/ml) | | Relative Oral Bioavailability Compound 10/ Compound IV |
|---|---|---|---|
| | Compound IV | Compound 10 | |
| 3 | 537 | 14,642 | 27 |
| 10 | 1,469 | 47,360 | 32 |
| 30 | 2,973 | 135,673 | 46 |
| 100 | 4,596 | 379,650 | 83 |
| 300 | 5,446 | 782,022 | 144 |

Example 6: Comparative In Vitro Activity

The in vitro antibacterial activity of prodrug compound 10 bis-ethanolamine salt (prodrug of compound Z/compound IV), compound Z itself, and other comparators were evaluated in a broth microdilution assay against methicillin-resistant and methicillin-sensitive *Staphylococcus aureus*, *Enterococcus faecalis*, *Streptococcus pneumoniae*, *Streptococcus pyogenes* and *Escherichia coli*.

Bacterial Isolates.

Organisms tested in this study are listed in Table P. Clinical isolates consisted of 5 *Staphylococcus aureus* (MSSA), 3 *Staphylococcus aureus* (HA-MRSA), 2 *Staphylococcus aureus* (CA-MRSA), 2 *Enterococcus faecalis* (VSE), 2 *Streptococcus pyogenes*, and 2 *Escherichia coli* (susceptible to most antibiotics). *S. aureus* ATCC 29213, *E. faecalis* ATCC 29212, *S. pneumoniae* ATCC 49619, and *E. coli* ATCC 25922 were tested for the purposes of quality control.

MIC Methodology.

Minimal Inhibitory Concentrations (MIC) values against the selected isolates were determined using the reference broth microdilution method according to the Clinical Laboratory Standards Institute (CLSI) guidelines.

The MIC was read and recorded as the lowest concentration of drug that inhibited visible growth of the organism.

TABLE P

In vitro antibacterial activity of Compound 10, Compound Z and comparator antibiotics

| Organism | MIC (µg/ml) | | | | |
|---|---|---|---|---|---|
| | Compound 10 | Compound Z | Vancomycin | Linezolid | Ciprofloxacin |
| *S. aureus* ATCC 29213 | 4 | 0.004 | 0.5 | 4 | 0.5 |
| *S. aureus* 3104; MSSA | >16 | 0.015 | 0.5 | 2 | 0.25 |
| *S. aureus* 3107; MSSA | 8 | 0.004 | 0.5 | 2 | 0.5 |
| *S. aureus* 3245; MSSA | 16 | 0.015 | 0.5 | 2 | 0.5 |
| *S. aureus* 3250; MSSA | 8 | 0.004 | 0.5 | 4 | 2 |
| *S. aureus* 3856; MSSA | 16 | 0.004 | 1 | 2 | >64 |
| *S. aureus* 3083; HA-MRSA | 4 | 0.004 | 0.5 | 2 | 32 |
| *S. aureus* 3086; HA-MRSA | 16 | 0.03 | 1 | 2 | >64 |
| *S. aureus* 3265; HA-MRSA | 16 | 0.004 | 0.5 | 2 | >64 |
| *S. aureus* 2168; CAMRSA | 4 | 0.004 | 1 | 2 | 16 |
| *S. aureus* 2294; CAMRSA | 16 | 0.03 | 1 | 2 | >64 |
| *E. faecalis* ATCC 29212 | >16 | >2 | 1 | 1 | 0.5 |
| *E. faecalis* 4158; VSE | >16 | >2 | >64 | 1 | 64 |
| *E. faecalis* 4212; VSE | >16 | >2 | 16 | 1 | 32 |
| *S. pneumoniae* ATCC 49619 | >16 | >2 | 0.12 | 1 | 0.5 |

TABLE P-continued

In vitro antibacterial activity of Compound 10, Compound Z and comparator antibiotics

| | MIC (µg/ml) | | | | |
|---|---|---|---|---|---|
| Organism | Compound 10 | Compound Z | Vancomycin | Linezolid | Ciprofloxacin |
| S. pyogenes 6179 | >16 | >2 | 0.25 | 1 | 0.5 |
| S. pyogenes 6528 | >16 | >2 | 0.25 | 1 | 0.5 |
| E. coli ATCC 25922 | >16 | >2 | >64 | 64 | 0.008 |
| E. coli 2214 | >16 | >2 | >64 | >64 | 0.015 |
| E. coli 5255 | >16 | >2 | >64 | 64 | 0.008 |

As shown in Table P, compound 10, a prodrug of compound Z showed 500-4000 times less activity than Compound Z against a panel of 11 *S. aureus* strains. (This negligible activity is probably due to traces of Compound IV (~0.1%) in compound 10 API.) In part by virtue of the prodrug nature, compound 10 shows no inhibition of *S. aureus* FabI; no inhibition of non-staphylococcal species, as does compound Z. The control antibiotics show the expected activity against all bacterial species tested.

Example 7: Preparation of N-Boc Amino Acid Chloromethyl Esters (26), the Corresponding Prodrug N-Boc Amino Acid Esters (27) and the Corresponding Prodrug Amino Acid Esters (28)

The esters can be prepared as in Scheme 3:

Scheme 3:

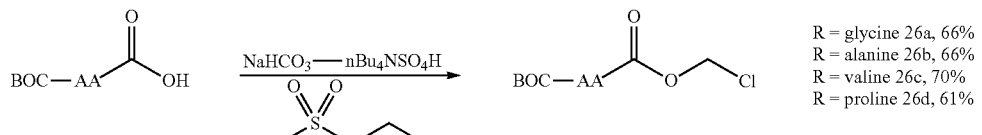

R = glycine 26a, 66%
R = alanine 26b, 66%
R = valine 26c, 70%
R = proline 26d, 61%

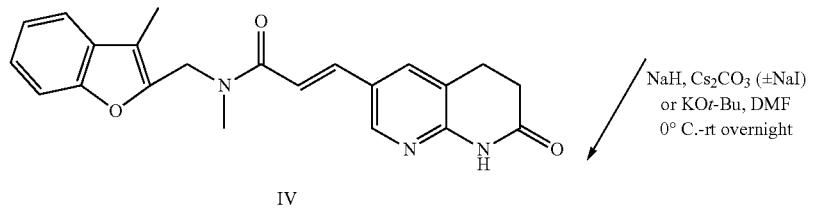

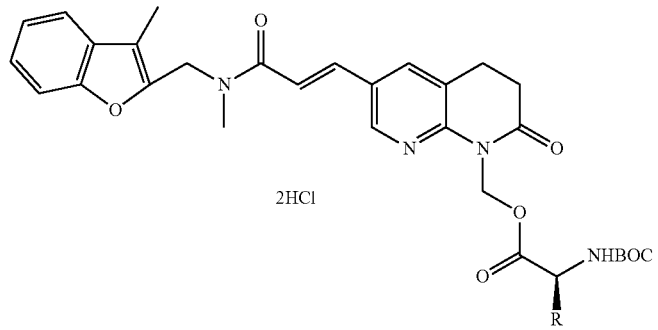

R = glycine 27a, 20%
R = alanine 27b, 20%
R = valine 27c, 20%
R = proline 27d, 61%

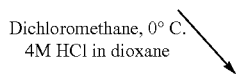

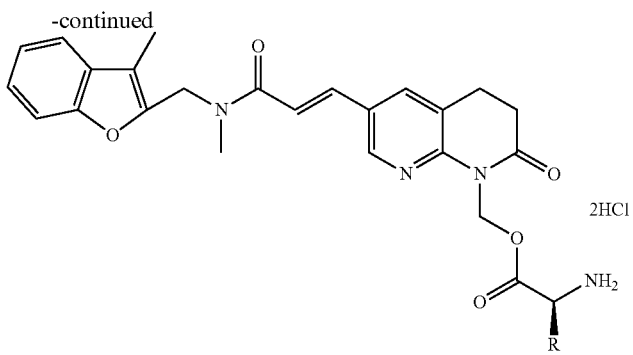

R = glycine 28a, 50%
R = alanine 28b, 55%
R = valine 28c, 45%
R = proline 28d, 60%

To individual two-phase solutions (50 mL water and 50 mL dichloromethane) of sodium bicarbonate (52 mmol, 4 equivalents), tetrabutylammonium hydrogensulfate (1.3 mmol, 0.1 equivalents) and the BOC-protected amino acids that are individually N-BOC-glycine, N-BOC-L-alanine, N-BOC-L-valine, and N-BOC-L-proline (13 mmol, 1 equivalent each) at 0° C. was slowly added (15.6 mmol, 1.2 equivalents) of chloromethyl chlorosulfate in 15 mL of dichloromethane each. The slurries were stirred for 12 hours as they warmed to room temperature. The organic layers were separated and the aqueous layers were individually extracted once more with 50 mL of dichloromethane. The individual combined organic layers were then dried over anhydrous sodium sulfate, filtered and the filtrates concentrated in vacuo to yield the crude products as residues. The residues were individually purified by flash chromatography (25% EtOAc/hex with 3% NEt$_3$ (critical buffer). This yielded pure materials as colorless oils which were each >95% pure by $^1$H NMR:

Compound 26a: $^1$H NMR (400 MHz, CDCl$_3$): δ 5.50 (s, 2H), 5.10 (bs, 1H), 3.95 (d, 2H), 1.40 (s, 9H).

Compound 26b $^1$H NMR (300 MHz, CDCl$_3$): δ 5.73 (dd, 2H), 4.95 (s broad, 1H), 4.35 (m, 1H), 1.47 (s, 9H), 1.42 (d, 3H).

Compound 26c: $^1$H NMR (400 MHz, CDCl$_3$): δ 5.68 (dd, 2H), 5.00 (bs, 1H), 4.20 (m, 1H), 2.20 (m, 1H), 1.40 (s, 9H), 1.00 (d, 3H), 0.95 (d, 3H).

Compound 26d $^1$H NMR (400 MHz, CDCl$_3$): δ 5.75 (m, 2H), 4.35 (m, 1H), 3.50 (m, 2H), 2.25 (m, 1H), 1.95 (m, 3H), 1.41 (s, 9H).

General Procedure for Synthesis of Compounds 27:

Individual reactions of Compound IV (5 mmol, 1 equivalent) were placed in DMF (50 mL) at room temperature and cesium carbonate (6 mmol, 1.2 equivalents) was added to each reaction in portions. The solutions were stirred for 30 minutes upon which (6 mmol, 1.2 equivalents) of the individual chloro reagents, 26 (dissolved in 5 mL of DMF), were added and the yellow solutions were stirred overnight at room temperature. The reactions were quenched with dilute aqueous ammonium chloride (1 L) followed by water (2 L) and the quenched mixtures were individually extracted twice with ethyl acetate (EtOAc) (2 L). After the organic layers were back-extracted with water (1 L) to remove DMF, the organic layers were individually dried over anhydrous sodium sulfate, filtered and the filtrates individually concentrated in vacuo. The crude products were individually purified by flash chromatography (50-100% EtOAc/hex) to yield pure materials as light-colored oils:

Compound 27a $^1$H NMR (300 MHz, CDCl$_3$): δ 8.38 (d, 1H), 7.68 (m, 2H), 7.50 (d, 1H), 7.41 (d, 1H), 7.25 (m, 2H), 6.90 (d, 1H), 6.25 (s, 2H), 5.05 (s broad, 1H), 4.85, 4.75 (2s, 2H), 3.90 (bs, 2H), 3.25, 310 (2s, 3H), 2.98 (m, 2H), 2.78 (m, 2H), 2.32 (s, 3H), 1.42 (s, 9H).

Compound 27b $^1$H NMR (300 MHz, CDCl$_3$): δ 8.38 (d, 1H), 7.68 (m, 2H), 7.50 (d, 1H), 7.41 (d, 1H), 7.25 (m, 2H), 6.90 (d, 1H), 6.30, 6.25 (2s, 2H), 5.05 (s broad, 1H), 4.85, 4.75 (2s, 2H), 4.30 (s broad, 1H), 3.25, 310 (2s, 3H), 2.98 (m, 2H), 2.78 (m, 2H), 2.32 (s, 3H), 1.42 (s, 9H), 1.25 (d, 3H).

Compound 27c $^1$H NMR (300 MHz, CDCl$_3$): 8.42 (m, 1H), 8.10-7.90 (m, 2H), 7.60 (d, 1H), 7.58 (d, 1H), 7.41 (d, 1H), 7.30-25 (m, 2H), 6.30, 6.25 (2s, 2H), 6.05 (s broad, 1H), 4.95, 4.85 (2s, 2H), 4.40, 4.10 (2m, 1H), 3.25, 310 (2s, 3H), 2.98 (m, 2H), 2.78 (m, 2H), 2.32 (s, 3H), 2.05 (m, 1H), 1.42 (s, 9H).

Compound 27d $^1$H NMR (300 MHz, CDCl$_3$): δ 8.40 (d, 1H), 7.66 (m, 2H), 7.50 (d, 1H), 7.41 (d, 1H), 7.25 (m, 2H), 6.89 (d, 1H), 6.22 (m, 2H), 4.83, 4.73 (2s, 2H), 4.25 (m, 1H), 3.45 (m, 2H), 3.25, 310 (2s, 3H), 2.95 (m, 2H), 2.78 (m, 2H), 2.32 (s, 3H), 2.25 (m, 1H), 1.95 (m, 3H), 1.20 (2s, 9H), 1.00, 0.95 (2d, 6H).

General Procedure for Synthesis of Compounds 28

Compounds 27 (0.1 mmol, 1 equivalent) were individually dissolved in dichloromethane (10 mL), cooled to 0° C. and hydrogen chloride (0.4 mL of a 4M solution in dioxane, 16 mmol, 16 equivalents) was added dropwise to each reaction. The individual solutions were stirred for 45 minutes as they warmed to room temperature. The solutions were then concentrated in vacuo to yield sticky oils. Acetone (5 mL) was added to the individual oils and these solutions were vigorously stirred until the oils solidified. The individual solids were filtered and air dried to yield pure materials which were >95% pure by $^1$H NMR, LRMS and HPLC.

Compound 28a: $^1$H NMR (400 MHz, CDCl$_3$): δ 8.95 (s broad, 2H), 8.30 (d, 1H), 7.50-7.20 (m, 7H), 6.15 (s, 2H), 5.00, 4.8 (2s, 2H), 4.40 (m, 1H), 3.90 (s, 2H), 318, 2.90 (2s, 3H), 2.95 (m, 2H), 2.75 (m, 2H), 2.25 (s, 3H).

Compound 28b $^1$H NMR (400 MHz, DMSO d$_6$): δ 8.50 (d, 1H), 8.35 (s broad, 2H), 8.22 (d, 1H), 7.55 (m, 2H), 7.45 (m, 1H), 7.25 (m, 3H), 6.15 (s, 2H), 5.00, 4.80 (2s, 2H), 4.10 (m, 1H), 3.18, 2.90 (2s, 3H), 2.95 (m, 2H), 2.75 (m, 2H), 2.25 (s, 3H), 1.30 (d, 3H).

Compound 28c: $^1$H NMR (400 MHz, CDCl$_3$): δ 8.60-8.40 (m, 3H), 8.20 (m, 2H), 7.70-7.10 (m, 6H), 6.20, 6.10 (2d, 2H), 5.00, 4.80 (2s, 2H), 3.90 (s, 1H), 3.18, 2.90 (2s, 3H), 2.95 (m, 2H), 2.75 (m, 2H), 2.25 (s, 3H), 0.90 (m, 3H).

Compound 28d $^1$H NMR (400 MHz, DMSO d$_6$): δ 9.80 (s broad, 1H), 8.95 (s broad, 1H), 8.50 (d, 1H), 8.23 (d, 1H), 7.55 (m, 2H), 7.45 (m, 1H), 7.25 (d, 3H), 6.15 (s, 2H), 5.00, 4.70 (2s, 2H), 4.28 (m, 1H), 3.18 (m, 5H), 2.95 (m, 2H), 2.75 (m, 2H), 2.25 (s, 3H), 2.18 (m, 1H), 1.90 (m, 3H).

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

We claim:
1. A compound represented by:

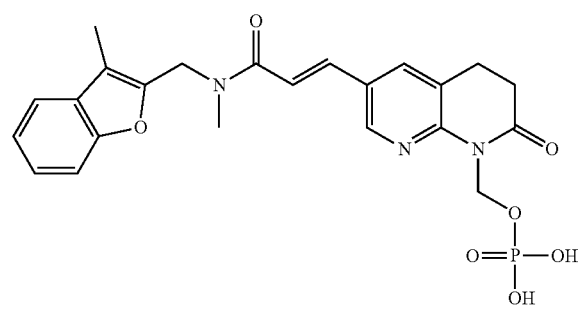

or a pharmaceutically acceptable salt thereof.

2. A pharmaceutically acceptable composition comprising the compound of claim 1 and a pharmaceutically acceptable excipient.

3. The pharmaceutically acceptable composition of claim 2, wherein the composition is a powder, tablet, pill, or capsule.

4. The pharmaceutically acceptable composition of claim 2, wherein the composition is a sterile aqueous composition.

5. A pharmaceutically acceptable composition suitable for oral administration, comprising a compound of claim 1 and a pharmaceutically acceptable excipient suitable for the oral administration.

6. A pharmaceutically acceptable composition for intravenous administration, comprising a compound of claim 1 and a pharmaceutically acceptable excipient suitable for the intravenous administration.

7. A compound represented by formula I:

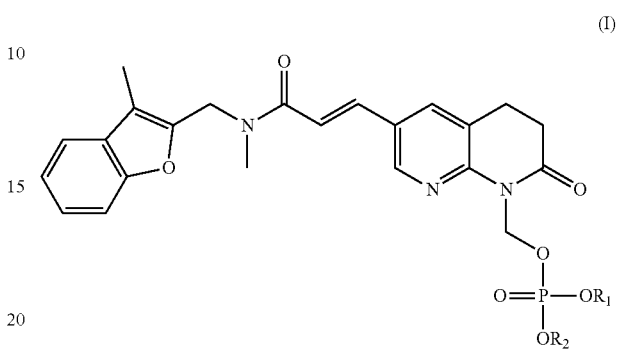

wherein,

R$_1$ and R$_2$ are each independently selected from the group consisting of hydrogen, an alkali metal, NH$_4^+$, NH$_3^+$—(R$_3$), NH$_2^+$—(R$_3$)$_2$, and NH$^+$—(R$_3$)$_3$, or R$_1$ and R$_2$ taken together are an alkaline earth metal; and R$_3$ is independently selected from the group consisting of C$_{1-6}$alkyl-, hydroxyC$_{1-6}$alkyl-, phenyl and benzyl.

8. The compound of claim 7, wherein R$_1$ and R$_2$ are each NH$_3^+$—(R$_3$).

9. The compound of claim 7, wherein one of R$_1$ and R$_2$ is H; and one of R$_1$ and R$_2$ is NH$_4^+$ or NH$_3^+$—(R$_3$).

10. The compound of claim 7, wherein R$_3$ is —CH$_2$CH$_2$OH.

11. The compound of claim 7, wherein R$_1$ and R$_2$ are an alkali metal.

12. The compound of claim 11, wherein the alkali metal is selected from the group consisting of lithium, sodium and potassium.

13. The compound of claim 7, wherein R$_1$ and R$_2$ taken together are an alkaline earth metal.

14. The compound of claim 13, wherein the alkaline earth metal is calcium or magnesium.

15. The compound of claim 7, wherein the compound is represented by:

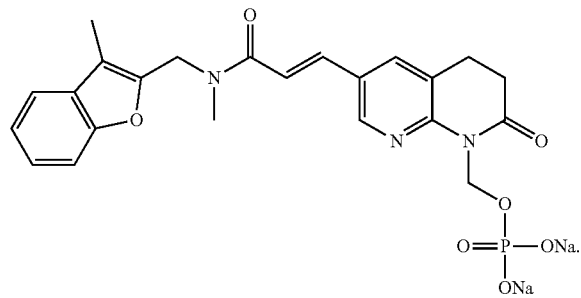

16. The compound of claim 7, wherein the compound is represented by:

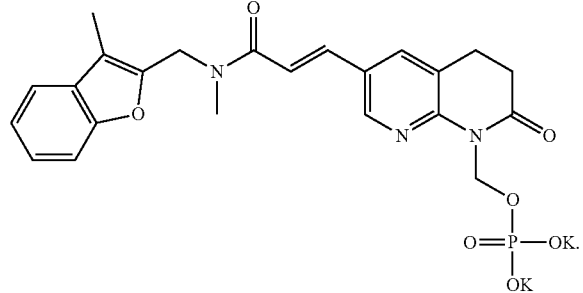

17. The compound of claim 7, wherein the compound is represented by:

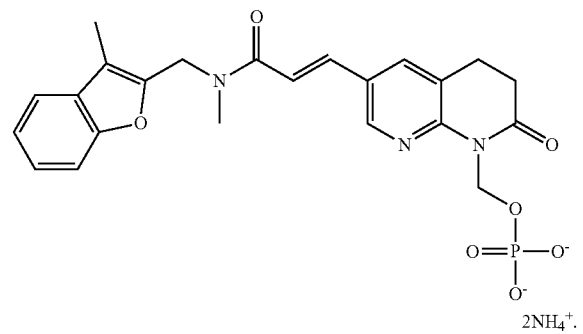 [SMILES: Cc1c(CN(C)C(=O)/C=C/c2cnc3c(c2)CCC(=O)N3COP(=O)([O-])[O-])oc2ccccc12]

18. The compound of claim 7, wherein the compound is represented by:

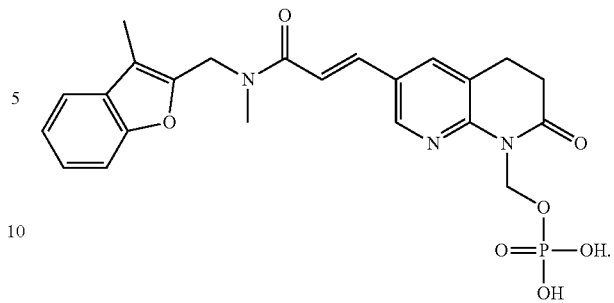

19. A method of treating a *Staphylococcus aureus* bacterial infection, comprising administering to a patient in need thereof a composition of claim 2 to treat the *Staphylococcus aureus* bacterial infection.

20. The method of claim 19, wherein the *Staphylococcus aureus* is methicillin-resistant.

21. The method of claim 19, wherein the patient is a human.

22. The method of claim 19, wherein administering is selected from the group consisting of orally administering, intravenously administering, subcutaneously administering, topically administering, and administration by inhalation.

23. The method of claim 19, wherein administering is orally administering.

24. The method of claim 19, wherein administering is intravenously administering or subcutaneously administering.

25. The method of claim 19, further comprising administering to said patient a compound selected from the group consisting of an oxazolidinone, vancomycin, a glycopeptide, a penicillin, a cephalosporin, a pleuromutilin, a fusidane, a lincosamide, rifamycin, and arbekacin.

26. The method of claim 19, further comprising administering to said patient a compound selected from the group consisting of linezolid, daptomycin, teicoplanin, and telavancin.

27. The method of claim 19, further comprising administering to said patient a compound selected from the group consisting of quinolones, fluoroquinolones, carbapenems, aminoglycosides, tetracyclines, streptogramins, and macrolides.

* * * * *